(12) United States Patent
Hilpert et al.

(10) Patent No.: US 9,221,832 B2
(45) Date of Patent: Dec. 29, 2015

(54) HETEROCYCLIC AMIDE DERIVATIVES AS P2X7 RECEPTOR ANTAGONISTS

(75) Inventors: Kurt Hilpert, Allschwil (CH); Francis Hubler, Allschwil (CH); Thierry Kimmerlin, Allschwil (CH); Dorte Renneberg, Allschwil (CH); Simon Stamm, Allschwil (CH); Mark Murphy, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 14/234,250

(22) PCT Filed: Jul. 20, 2012

(86) PCT No.: PCT/IB2012/053712
§ 371 (c)(1),
(2), (4) Date: Jan. 22, 2014

(87) PCT Pub. No.: WO2013/014587
PCT Pub. Date: Jan. 31, 2013

(65) Prior Publication Data
US 2014/0163035 A1    Jun. 12, 2014

(30) Foreign Application Priority Data
Jul. 22, 2011    (WO) .................. PCT/IB2011/053280

(51) Int. Cl.
*A61K 31/4355* (2006.01)
*C07D 491/052* (2006.01)
*C07D 491/048* (2006.01)
*A61K 31/436* (2006.01)

(52) U.S. Cl.
CPC ........ *C07D 491/052* (2013.01); *C07D 491/048* (2013.01)

(58) Field of Classification Search
CPC ............ A61K 31/4355; A61K 31/436; C07D 491/052; C07D 491/048
USPC .................... 514/248, 302; 544/235; 546/115
See application file for complete search history.

(56) References Cited

U.S. PATENT DOCUMENTS

| | | | |
|---|---|---|---|
| 2006/0052374 A1 | 3/2006 | Carroll et al. | |
| 2007/0049584 A1 | 3/2007 | Carroll et al. | |
| 2007/0281939 A1 | 12/2007 | Dombrowski et al. | |
| 2008/0171733 A1 | 7/2008 | Carroll et al. | |
| 2008/0287415 A1 | 11/2008 | Kelly | |
| 2010/0267762 A1 | 10/2010 | Boes | |
| 2010/0286390 A1* | 11/2010 | Shigeta et al. ................ | 544/114 |
| 2011/0212992 A1 | 9/2011 | Boes | |
| 2012/0157494 A1 | 6/2012 | Harris, III et al. | |
| 2014/0073651 A1 | 3/2014 | Hilpert et al. | |
| 2015/0025075 A1 | 1/2015 | Hilpert et al. | |

FOREIGN PATENT DOCUMENTS

| | | |
|---|---|---|
| EP | 2 243 772 | 10/2010 |
| WO | WO 00/61569 | 10/2000 |
| WO | WO 01/42194 | 6/2001 |
| WO | WO 01/44170 | 6/2001 |
| WO | WO 01/94338 | 12/2001 |
| WO | WO 03/041707 | 5/2003 |
| WO | WO 03/042190 | 5/2003 |
| WO | WO 03/042191 | 5/2003 |
| WO | WO 03/080579 | 10/2003 |
| WO | WO 2004/058270 | 7/2004 |
| WO | WO 2004/058731 | 7/2004 |
| WO | WO 2004/074224 | 9/2004 |
| WO | WO 2004/099146 | 11/2004 |
| WO | WO 2004/106305 | 12/2004 |
| WO | WO 2005/009968 | 2/2005 |
| WO | WO 2005/111003 | 11/2005 |
| WO | WO 2006/025783 | 3/2006 |
| WO | WO 2006/059945 | 6/2006 |
| WO | WO 2006/080884 | 8/2006 |
| WO | WO 2006/102588 | 9/2006 |
| WO | WO 2006/102610 | 9/2006 |
| WO | 2007055374 | 5/2007 |
| WO | WO 2007/109154 | 9/2007 |
| WO | WO 2007/109160 | 9/2007 |
| WO | WO 2007/109172 | 9/2007 |

(Continued)

OTHER PUBLICATIONS

U.S. Appl. No. 14/373,338, filed Jul. 18, 2014 Kurt Hilpert et al.
Abberley, L. et al., "Identification of 2-oxo-N-(phenylmethyl)-4-imidazolidinecarboxamide antagonists of the P2X7 receptor", Bioorg. Med. Chem. Lett., (2010), doi:10.1016/j.bmcl.2010.09.101, vol. 20, pp. 6370-6374.
Abdi, M.H. et al., "Discovery and structure-activity relationships of a series of pyroglutamic acid amide antagonists of the P2X7 receptor", Bioorg. Med. Chem. Lett., (2010), vol. 20, doi:10.1016/j.bmcl.2010.07.033, pp. 5080-5084.
Badarau E., et al., "Synthesis-of 3-Amino-8-azachromans and 3-Amino-7-azabenzofurans via Inverse Electron Demand Dieis-Alder Reaction", Eur. J. Org. Chem. (2009), pp. 3619-3627.
Chen X. et al., "Discovery of 2-chloro-N((4,4-difluoro-1-hydroxycyclohexyl)methl)-5-(5-fluoropyrimidin-2-yl)benzamide as a potent and CNS penetrable P2X7 receptor antagonist", Bioorg. Med. Chem. Lett., (2010), doi:10.1016/j.bmcl.2010.03.094, vol. 20, pp. 3107-3111.

(Continued)

*Primary Examiner* — Janet L Andres
*Assistant Examiner* — Daniel Carcanague
(74) *Attorney, Agent, or Firm* — Hoxie & Associates, LLC

(57) ABSTRACT

The invention relates to heterocyclic amide derivatives of formula (I), wherein $R^1$, $R^2$, $R^3$, $R^4$, $R^5$, X, Y and n are as defined in the description, their preparation and their use as pharmaceutically active compounds.

(I)

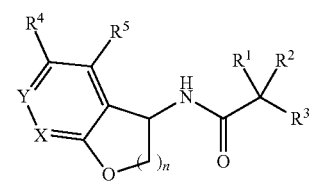

14 Claims, No Drawings

(56) References Cited

FOREIGN PATENT DOCUMENTS

| | | |
|---|---|---|
| WO | WO 2007/109182 | 9/2007 |
| WO | WO 2007/109192 | 9/2007 |
| WO | WO 2007/109201 | 9/2007 |
| WO | WO 2007/141267 | 12/2007 |
| WO | WO 2007/141269 | 12/2007 |
| WO | WO 2008/003697 | 1/2008 |
| WO | WO 2008/013494 | 1/2008 |
| WO | WO 2008/066789 | 6/2008 |
| WO | WO 2008/094473 | 8/2008 |
| WO | WO 2008/094473 A1 | 8/2008 |
| WO | WO 2008/112205 | 9/2008 |
| WO | WO 2008/114002 | 9/2008 |
| WO | WO 2008/116814 | 10/2008 |
| WO | WO 2008/116845 | 10/2008 |
| WO | WO 2008/119685 | 10/2008 |
| WO | WO 2008/119825 | 10/2008 |
| WO | WO 2008/124153 | 10/2008 |
| WO | WO 2008/125600 | 10/2008 |
| WO | WO 2008/138876 | 11/2008 |
| WO | WO 2009/012482 | 1/2009 |
| WO | WO 2009/023623 | 2/2009 |
| WO | WO 2009/070116 | 6/2009 |
| WO | WO 2009/074518 | 6/2009 |
| WO | WO 2009/074519 | 6/2009 |
| WO | WO 2009/077362 | 6/2009 |
| WO | WO 2009/077559 | 6/2009 |
| WO | WO 2009/108551 | 9/2009 |
| WO | WO 2009/118175 | 10/2009 |
| WO | WO 2009/132000 | 10/2009 |
| WO | WO 2010/118921 | 10/2010 |
| WO | WO 2011/027156 | 3/2011 |
| WO | WO 2011/054947 | 5/2011 |
| WO | WO 2012/114268 | 8/2012 |
| WO | WO 2013/108227 | 7/2013 |
| WO | 2014091415 | 6/2014 |
| WO | 2014097140 | 6/2014 |
| WO | 2014115072 | 7/2014 |
| WO | 2014115078 | 7/2014 |

OTHER PUBLICATIONS

Chessell, I.P., et al., "Disruption of the P2X$_7$ purinoceptor gene abolishes chronic inflammatory and neuropathic pain", Pain, doi:10.1016/j.pain/2005.01.002, (2005), vol. 114, pp. 386-396.

Deuchars, S.A. et al., "Neuronal P2X$_7$ Receptors Are Targeted to Presynaptic Terminals in the Central and Peripheral Nervous Systems", J. Neurosci. (2001), vol. 21(18), pp. 7143-7152

Duplantier, A.J. et al., "Optimization of the physicochemical and pharmacokinetic attributes in a 6-azauracil series of P2X$_7$ receptor antagonists leading to the discovery of the clinical candidate CE-224,535", Bioorg. Med. Chem. Lett., (2011), doi:10.1016/j.bmcl.2011.04.077, vol. 21, pp. 3708-3711.

Ferrari, D. et al., "ATP-mediated Cytotoxicity in Microglial Cells", Neuropharmacology (1997), vol. 36(9), pp. 1295-1301.

Furber, J. et al., Discovery of Potent and Selective Adamantane-Based Small-Molecule P2X$_7$ Receptor Antagonists/Interleukin-1β Inhibitors, J. Med. Chem., 2007, doi:10.1021/jm700949w, vol. 50, pp. 5882-5885.

Gould, P., "Salt selection for basic drugs", Int. J. Pharm, (1986), vol. 33, pp. 201-217.

Greene, T.W. et al., "Protective Groups in Organic Synthesis 3$^{rd}$ Edition", (Table of Contents) (1999).

Guile, S.D. et al., "Antagonists of the P2X$_7$ Receptor, From Lead Identification to Drug Development", J. Med. Chem., (2009), vol. 52(10), pp. 3123-3141.

Morita, H. et al., "Furopyridines. VI. Preperation and Reactions of 2- and 3-Substituted Furo[2,3-b]pyridines", J. Heterocyclic Chem., (Sep.-Oct. 1986), vol. 23, pp. 1465-1469.

North, R.A., "Molecular Physiology of P2X Receptors", Physiol. Rev. (2002), vol. 82(4), pp. 1013-1067, doi:10.1152/physrev.00015.2002.

Remington, The Science and Practice of Pharmacy, 21st Edition, (2005), Part 5, (front and back cover of book and Table of Contents).

Solle, M. et al., "Altered Cytokine Production in Mice Lacking P2X7 Receptors", J. Biol. Chem., (2001), vol. 276(1), pp. 125-132.

Sperlagh B. et al., "Involvment of P2X$_7$ receptors in the regulation of neurotransmitter release in the rat hippocampus", J. Neurochem. (2002), vol. 81, pp. 1196-1211.

Subramanyam, C., et al., "Discovery, syntheses and SAR of azinyl- and azolylbenzamides antagonist of the P2X$_7$ receptor", Bioorg. Med. Chem. Lett., (2011), doi:10.1016.j.bmcl.2011.06.117, vol. 21, pp. 5475-5479.

Surprenant, A. et al., The Cytolytic P$_{2Z}$ Receptor for Extracellular ATP Indentified as a P$_{2X}$ Receptor (P2X$_7$), Science (1996), vol. 272, (5262), pp. 735-738.

Tsukada T. et al., "A prodrug approach towards the development of tricyclic-based FBPase inhibitors", Bioorg. Med. Chem. Lett., doi:10.1016/j.bmcl.2010.03.017, (2010), 20(9), pp. 2938-2941.

Virginio, C., et al., "Kinetics of cell lysis, dye uptake and permeability changes in cells expressing the rat P2X$_7$ receptor", J. Physiol., (1999), vol. 519.2, pp. 335-346.

Wiley, J.S. et al., "Transduction mechanisms of P2Z purinoceptors", Ciba Found Symp., P2 PurinoReceptors: Localization, Function and Transduction Mechanisms, 198, pp. 149-160 and 160-165, (1996).

Yu, Y. et al., "Cellular localixation of P2X7 receptor mRNA in the rat brain", Brain. Res. (2008), doi:10.1016/j.brain.res.2007.11.064, vol. 1194, pp. 45-55.

Written Opinion of the International Search Authority mailed Nov. 28, 2012 for International Application PCT/IB2012/053712.

* cited by examiner

HETEROCYCLIC AMIDE DERIVATIVES AS P2X7 RECEPTOR ANTAGONISTS

CROSS REFERENCE TO RELATED APPLICATIONS

This application is a national stage application under 35 U.S.C. §371 of PCT/IB2012/053712, filed on Jul. 20, 2012, which claims the benefit of PCT/IB2011/053280 filed on Jul. 22, 2011, the contents of each of which are incorporated herein by reference.

The present invention relates to heterocyclic amide derivatives of formula (I) and their use as pharmaceuticals. The invention also concerns related aspects including processes for the preparation of the compounds, pharmaceutical compositions containing one or more compounds of formula (I), and especially their use as $P2X_7$ receptor antagonists.

The $P2X_7$ receptors (P2RX7) belong to the family of P2X ionotropic receptors that are activated by extracellular nucleotides, in particular adenosine triphosphate (ATP). P2RX7 is distinguished from other P2X family members by the high concentrations (mM range) of ATP required to activate it and its ability to form a large pore upon prolonged or repeated stimulation (North, R. A., Physiol. Rev. 2002, 82(4), 1013-67; Surprenant, A., Rassendren, F. et al., Science 1996, 272(5262), 735-8; Virginio, C., MacKenzie, A. et al., J. Physiol., 1999, 519, 335-46). P2RX7 is present on many cell types, especially ones known to be involved in inflammatory and immune processes. This is reflected within both the periphery and the CNS as Lipopolysaccharide S (LPS) priming of monocytes and microglia followed by ATP stimulation has been shown to lead to the local release and processing of IL1β and other family members including IL18 through a P2RX7 mediated mechanism. Indeed mice lacking the P2X7 receptor are unable to release IL1β following LPS priming and ATP stimulation providing further evidence of its role in this pathway (Solle, M., Labasi, J. et al., J. Biol. Chem., 2001, 276(1), 125-32). In addition L-selectin shedding from monocytes, macrophages and lymphocytes, degranulation in mast cells and apoptosis in lymphocytes are all associated with P2RX7 stimulation. P2RX7 is also expressed on epithelial and endothelial cells (Ferrari, D., Chiozzi, P. et al., Neuropharmacology 1997, 36(9), 1295-301; Wiley, J. S., Chen, J. R. et al., Ciba Found Symp. 1996, 198, 149-60 and 160-5; North, R. A., Physiol. Rev. 2002, 82(4), 1013-67). In addition to its role in the periphery it may have an important function in neurotransmission within the CNS through its activation on postsynaptic and/or presynaptic central and peripheral neurons and glia (Deuchars, S. A., Atkinson, L. et al., J. Neurosci. 2001, 21(18), 7143-52; Sperlagh, B., Kofalvi, A. et al., J. Neurochem. 2002, 81(6), 1196-211). Recent data that has emerged using in situ hybridization demonstrated that P2X7 receptor mRNA was widely distributed throughout the rat brain. Specifically, among the areas of high P2X7mRNA expression noted were the piriform cortex, hippocampus, pontine nuclei and the anterior horn of the spinal cord (Yu, Y., Ugawa, S. et al., Brain. Res. 2008, 1194, 45-55). Hence there is therapeutic rationale for the use of P2X7 ion channel blockers in the treatment of a variety of disease states. These include but are not limited to diseases associated with the central nervous system such as stroke or injury and diseases associated with neuro-degeneration and neuroinflammation such as Alzheimer's disease, Huntington's disease, epilepsy, Amyotrophic lateral sclerosis, acute spinal cord injury additionally to meningitis, sleep disorders, mood and anxiety disorders as well as chronic and neuropathic and inflammatory pain. Furthermore, peripheral inflammatory disorders and autoimmune diseases including but not limited to rheumatoid arthritis, osteoarthritis, psoriasis, allergic dermatitis, asthma, chronic obstructive pulmonary disease, airways hyper-responsiveness, septic shock, bronchitis, glomerulonephritis, irritable bowel disease, skin injury, lung emphysema, Limb girdle dystrophy type 2B, fibrosis, Syndrome of synovitis Acne Pustulosis, atherosclerosis, burn injury, spinal cord injury, Hyperostosis Osteitis, Crohn's disease, ulcerative colitis, growth and metastases of malignant cells, myoblastic leukaemia, diabetes, trauma, meningitis, osteoporosis, burn injury, ischemic heart disease, and varicose veins and trauma, are all examples where the involvement of P2X7 channels has been implicated. In addition a recent report suggests a link between P2RX7 and chronic, inflammatory and neuropathic pain (Chessell, I. P., Hatcher, J. P. et al., Pain, 2005, 114(3), 386-96). Overall, these findings indicate a role for the P2X7 receptor in the process of neuronal synaptic transmission and therefore a potential role for P2X7 antagonists as novel therapeutic tools to treat neuropathic pain.

In view of the above observations, there is significant requirement for P2X7 antagonists that can be efficiently used in treating neuropathic pain, chronic inflammatory pain, inflammation, and neurodegenerative conditions.

A different 3-amino dihydrofuropyridine derivative, which is also a $P2X_7$ receptor antagonist, has been disclosed in WO 2005/111003.

Various embodiments of the invention are presented hereafter:

1) The present invention relates to heterocyclic amide derivatives of formula (I),

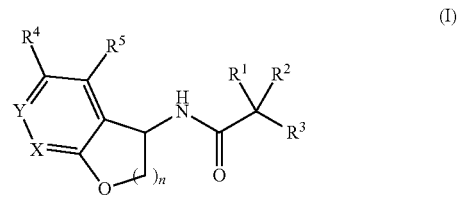

wherein
n represents 1 or 2;
one of X and Y represents —N— or —N(O)— and the other one represents —N— or —C($R^6$)—;
$R^1$ represents hydrogen or methyl and $R^2$ represents hydrogen, ($C_1$-$C_2$)alkyl, ($C_1$-$C_2$)deuteroalkyl, hydroxy-methyl or heterocyclyl-methyl; or
$R^1$ and $R^2$ form, together with the carbon atom to which they are attached, a saturated carbocyclic ring of 3 to 6 members; and
$R^3$ represents an aryl, an aryloxy, an aryl-($C_1$-$C_2$)alkyl, a heteroaryl or a heteroaryloxy group which groups are in the aromatic moiety independently mono-, di-, tri- or tetra-substituted, wherein the substituents are independently selected from the group consisting of ($C_1$-$C_3$)alkyl, ($C_3$-$C_6$)cycloalkyl, ($C_1$-$C_3$)alkoxy, hydroxy-($C_1$-$C_2$)alkyl, ($C_1$-$C_3$)fluoroalkyl, ($C_1$-$C_3$)fluoroalkoxy, ($C_1$-$C_2$)alkylcarbonyl, cyano, —$CONH_2$, halogen and phenoxy;
or
$R^1$ represents hydrogen and $R^2$ and $R^3$ form, together with the carbon atom to which they are attached, an indanyl or a tetrahydronaphthyl group (notably indanyl) which groups are in the aromatic moiety independently mono-, di- or tri-substituted (notably di-substituted), wherein the substituents are independently selected from the group consisting of $(C_1-C_3)$alkyl, $(C_1-C_3)$fluoroalkyl and halogen (notably from halogen); and $R^4$, $R^5$ and $R^6$ represent independently from each other hydrogen, $(C_1-C_3)$alkyl, $(C_3-C_6)$cycloalkyl, $(C_1-C_3)$alkoxy, $(C_1-C_3)$fluoroalkyl or halogen;

and to the salts (in particular pharmaceutically acceptable salts) of such compounds.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

The following paragraphs provide definitions of the various chemical moieties for the compounds according to the invention and are intended to apply uniformly throughout the specification and claims unless an otherwise expressly set out definition provides a broader or narrower definition.

The term "alkyl", used alone or in combination, refers to a straight or branched chain alkyl group containing one to three carbon atoms. The term "$(C_x-C_y)$alkyl" (x and y each being an integer), refers to an alkyl group as defined before containing x to y carbon atoms. For example a $(C_1-C_3)$alkyl group contains from one to three carbon atoms. Representative examples of alkyl groups include methyl, ethyl, n-propyl and iso-propyl.

In case "$R^2$" represents "$(C_1-C_2)$alkyl" the term means $(C_1-C_2)$alkyl groups as defined above. Examples of said groups are methyl and ethyl. Preferred is methyl.

In case "$R^4$" represents "$(C_1-C_3)$alkyl" the term means $(C_1-C_3)$alkyl groups as defined above. Examples of said groups are methyl, ethyl, n-propyl and iso-propyl. Preferred is methyl.

In case "$R^5$" represents "$(C_1-C_3)$alkyl" the term means $(C_1-C_3)$alkyl groups as defined above. Examples of said groups are methyl, ethyl, n-propyl and iso-propyl. Preferred is methyl.

In case "$R^6$" represents "$(C_1-C_3)$alkyl" the term means $(C_1-C_3)$alkyl groups as defined above. Examples of said groups are methyl, ethyl, n-propyl and iso-propyl. Preferred is methyl.

In case a $(C_1-C_3)$alkyl group is a substituent to an aryl, an aryloxy, an aryl-$(C_1-C_2)$alkyl (notably aryl-methyl), a heteroaryl or a heteroaryloxy group, the term "$(C_1-C_3)$alkyl" means $(C_1-C_3)$alkyl groups as defined above. Examples of said groups are methyl, ethyl, n-propyl and iso-propyl. Preferred are methyl and ethyl and most preferred is methyl.

In case a $(C_1-C_3)$alkyl group is a substituent to an indanyl or a tetrahydronaphthyl group formed by $R^2$, $R^3$ and the carbon atom to which they are attached, the term "$(C_1-C_3)$alkyl" means $(C_1-C_3)$alkyl groups as defined above. Examples of said groups are methyl, ethyl, n-propyl and iso-propyl. Preferred are methyl and ethyl and most preferred is methyl.

The term "$(C_1-C_2)$deuteroalkyl" refers to an alkyl group as defined before containing one or two carbon atoms in which between one and five hydrogen atoms have been replaced with deuterium. Examples of said groups are monodeuteromethyl, dideuteromethyl, trideuteromethyl, monodeuteroethyl, dideuteroethyl, trideuteroethyl, tetradeuteroethyl and pentadeuteroethyl. Preferred is trideuteromethyl.

The term "alkoxy", used alone or in combination, refers to an alkyl-O— group wherein the alkyl group is as defined above. The term "$(C_x-C_y)$alkoxy" (x and y each being an integer) refers to an alkoxy group as defined before containing x to y carbon atoms. For example a $(C_1-C_3)$alkoxy group contains from one to three carbon atoms. Representative examples of alkoxy groups include methoxy, ethoxy, n-propoxy and iso-propoxy.

In case "$R^4$" represents "$(C_1-C_3)$alkoxy" the term means $(C_1-C_3)$alkoxy groups as defined above. Examples of said groups are methoxy, ethoxy, n-propoxy and iso-propoxy. Preferred is methoxy.

In case "$R^5$" represents "$(C_1-C_3)$alkoxy" the term means $(C_1-C_3)$alkoxy groups as defined above. Examples of said groups are methoxy, ethoxy, n-propoxy and iso-propoxy. Preferred is methoxy.

In case "$R^6$" represents "$(C_1-C_3)$alkoxy" the term means $(C_1-C_3)$alkoxy groups as defined above. Examples of said groups are methoxy, ethoxy, n-propoxy and iso-propoxy. Preferred is methoxy.

In case a $(C_1-C_3)$alkoxy group is a substituent to an aryl, an aryloxy, an aryl-$(C_1-C_2)$alkyl (notably aryl-methyl), a heteroaryl or a heteroaryloxy group, the term "$(C_1-C_3)$alkoxy" means $(C_1-C_3)$alkoxy groups as defined above. Examples of said groups are methoxy, ethoxy, n-propoxy and iso-propoxy. Preferred is methoxy.

The term "$(C_3-C_6)$cycloalkyl", used alone or in combination, means a cycloalkyl group with 3 to 6 carbon atoms. Examples of $(C_3-C_6)$cycloalkyl groups are cyclopropyl, cyclobutyl, cyclopentyl and cyclohexyl.

In case "$R^4$" represents "$(C_3-C_6)$cycloalkyl" the term means $(C_3-C_6)$cycloalkyl groups as defined above. Examples of said groups are cyclopropyl, cyclobutyl, cyclopentyl and cyclohexyl. Preferred is cyclopropyl.

In case "$R^5$" represents "$(C_3-C_6)$cycloalkyl" the term means $(C_3-C_6)$cycloalkyl groups as defined above. Examples of said groups are cyclopropyl, cyclobutyl, cyclopentyl and cyclohexyl. Preferred is cyclopropyl.

In case "$R^6$" represents "$(C_3-C_6)$cycloalkyl" the term means $(C_3-C_6)$cycloalkyl groups as defined above. Examples of said groups are cyclopropyl, cyclobutyl, cyclopentyl and cyclohexyl. Preferred is cyclopropyl.

In case a $(C_3-C_6)$cycloalkyl group is a substituent to an aryl, an aryloxy, an aryl-$(C_1-C_2)$alkyl (notably aryl-methyl), a heteroaryl or a heteroaryloxy group, the term "$(C_3-C_6)$cycloalkyl" means $(C_3-C_6)$cycloalkyl groups as defined above. Examples of said groups are cyclopropyl, cyclobutyl, cyclopentyl and cyclohexyl. Preferred is cyclopropyl.

The term "saturated carbocyclic ring of 3 to 6 members" refers to a cyclopropyl, cyclobutyl, cyclopentyl and cyclohexyl ring.

The term "hydroxy-$(C_1-C_2)$alkyl", used alone or in combination, refers to an alkyl group as defined before containing one or two carbon atoms in which one hydrogen atom has been replaced with hydroxy. Examples of said groups are hydroxy-methyl, 1-hydroxy-ethyl and 2-hydroxy-ethyl. Preferred is hydroxy-methyl.

The term "$(C_1-C_2)$alkylcarbonyl", used alone or in combination, refers to an alkyl-C(O)— group wherein the alkyl group is as defined before, which is attached to the rest of the molecule via the carbonyl-C-atom. The term "$(C_x-C_y)$alkylcarbonyl" (x and y each being an integer) refers to an alkylcarbonyl group as defined before containing in the alkyl radical x to y carbon atoms. For example a $(C_1-C_2)$alkylcarbonyl group contains in the alkyl radical one or two carbon atoms. Representative examples of alkyl-carbonyl groups include methylcarbonyl and ethylcarbonyl. Preferred is methylcarbonyl.

The term "$(C_x-C_y)$fluoroalkyl" (x and y each being an integer) refers to an alkyl group as defined before containing x to y carbon atoms in which one or more (and possibly all) hydrogen atoms have been replaced with fluoro. For example a ($C_1$-$C_3$)fluoroalkyl group contains from one to three carbon atoms in which one to seven hydrogen atoms have been replaced with fluoro.

In case "$R^4$" represents "($C_1$-$C_3$)fluoroalkyl" the term means ($C_1$-$C_3$)fluoroalkyl groups as defined above. Examples of said groups are difluoromethyl, trifluoromethyl, 2,2-difluoroethyl and 2,2,2-trifluoroethyl. Preferred is trifluoromethyl.

In case "$R^5$" represents "($C_1$-$C_3$)fluoroalkyl" the term means ($C_1$-$C_3$)fluoroalkyl groups as defined above. Examples of said groups are difluoromethyl, trifluoromethyl, 2,2-difluoroethyl and 2,2,2-trifluoroethyl. Preferred is trifluoromethyl.

In case "$R^6$" represents "($C_1$-$C_3$)fluoroalkyl" the term means ($C_1$-$C_3$)fluoroalkyl groups as defined above. Examples of said groups are difluoromethyl, trifluoromethyl, 2,2-difluoroethyl and 2,2,2-trifluoroethyl. Preferred is trifluoromethyl.

In case "($C_1$-$C_3$)fluoroalkyl" is a substituent to an aryl, an aryloxy, an aryl-($C_1$-$C_2$)alkyl (notably aryl-methyl), a heteroaryl or a heteroaryloxy group, the term "($C_1$-$C_3$)fluoroalkyl" means ($C_1$-$C_3$)fluoroalkyl groups as defined above. Examples of said groups are difluoromethyl, trifluoromethyl, 2,2-difluoroethyl and 2,2,2-trifluoroethyl. Preferred are difluoromethyl and trifluoromethyl and most preferred is trifluoromethyl.

In case "($C_1$-$C_3$)fluoroalkyl" is a substituent to an indanyl or a tetrahydronaphthyl group formed by $R^2$, $R^3$ and the carbon atom to which they are attached, the term "($C_1$-$C_3$)fluoroalkyl" means ($C_1$-$C_3$)fluoroalkyl groups as defined above. Examples of said groups are difluoromethyl, trifluoromethyl, 2,2-difluoroethyl and 2,2,2-trifluoroethyl. Preferred are difluoromethyl and trifluoromethyl and most preferred is trifluoromethyl.

The term "($C_x$-$C_y$)fluoroalkoxy" (x and y each being an integer) refers to an alkoxy group as defined before containing x to y carbon atoms in which one or more (and possibly all) hydrogen atoms have been replaced with fluoro. For example a ($C_1$-$C_3$)fluoroalkoxy group contains from one to three carbon atoms in which one to seven hydrogen atoms have been replaced with fluoro.

In case "($C_1$-$C_3$)fluoroalkoxy" is a substituent to an aryl, an aryloxy, an aryl-($C_1$-$C_2$)alkyl (notably aryl-methyl), a heteroaryl or a heteroaryloxy group, the term "($C_1$-$C_3$)fluoroalkoxy" means ($C_1$-$C_3$)fluoroalkoxy groups as defined above. Examples of said groups are difluoromethoxy, trifluoromethoxy, 2,2-difluoroethoxy and 2,2,2-trifluoroethoxy. Preferred is trifluoromethoxy.

The term halogen means fluoro, chloro, bromo or iodo, preferably fluoro or chloro and most preferably chloro.

In case "$R^4$" represents "halogen" the term means fluoro, chloro, bromo or iodo, preferably fluoro or chloro and most preferably chloro.

In case "$R^5$" represents "halogen" the term means fluoro, chloro, bromo or iodo, preferably fluoro or chloro and most preferably chloro.

In case "$R^6$" represents "halogen" the term means fluoro, chloro, bromo or iodo, preferably fluoro or chloro and most preferably chloro.

In case "halogen" is a substituent to an aryl, an aryloxy, an aryl-($C_1$-$C_2$)alkyl (notably aryl-methyl), a heteroaryl or a heteroaryloxy group, the term "halogen" means fluoro, chloro, bromo or iodo, preferably fluoro or chloro and most preferably chloro.

In case "halogen" is a substituent to an indanyl or a tetrahydronaphthyl group formed by $R^2$, $R^3$ and the carbon atom to which they are attached, the term "halogen" means fluoro, chloro, bromo or iodo, preferably fluoro or chloro and most preferably chloro.

The term "aryl", used alone or in any combination, means a phenyl or a naphthyl group. Preferred is a phenyl group. The aryl group is mono-, di-, tri- or tetra-substituted (preferably di- or tri-substituted), wherein the substituents are independently selected from the group consisting of ($C_1$-$C_3$)alkyl, ($C_3$-$C_6$)cycloalkyl, ($C_1$-$C_3$)alkoxy, hydroxy-($C_1$-$C_2$)alkyl, ($C_1$-$C_3$)fluoroalkyl, ($C_1$-$C_3$)fluoroalkoxy, ($C_1$-$C_2$)alkylcarbonyl, cyano, —$CONH_2$, halogen and phenoxy (notably from ($C_1$-$C_3$)alkyl, ($C_3$-$C_6$)cycloalkyl, ($C_1$-$C_3$)alkoxy, ($C_1$-$C_3$)fluoroalkyl, ($C_1$-$C_3$)fluoroalkoxy, cyano, halogen and phenoxy); preferably the substituents are independently selected from the group consisting of ($C_1$-$C_3$)alkyl, ($C_3$-$C_6$)cycloalkyl, ($C_1$-$C_3$)fluoroalkyl, cyano and halogen (most preferably from methyl, ethyl, cyclopropyl, trifluoromethyl, cyano, chloro and fluoro). Examples are 2,4-difluoro-phenyl, 2,4,6-trifluoro-phenyl, 2-chloro-phenyl, 4-chloro-phenyl, 2-chloro-4-fluoro-phenyl, 2-chloro-6-fluoro-phenyl, 2,3-dichloro-phenyl, 2,4-dichloro-phenyl, 3,4-dichloro-phenyl, 2,3-dichloro-6-fluoro-phenyl, 2,4-dichloro-5-fluoro-phenyl, 2,4-dichloro-6-fluoro-phenyl, 2,4-dichloro-6-methyl-phenyl, 2,4-dichloro-6-ethyl-phenyl, 2-chloro-6-fluoro-3-methyl-phenyl, 2,4-dichloro-6-cyclopropyl-phenyl, 2-fluoro-4-methoxy-phenyl, 2-fluoro-6-trifluoromethyl-phenyl, 4-chloro-2-fluoro-3-methyl-6-trifluoromethyl-phenyl, 4-fluoro-2-trifluoromethyl-phenyl, 2-chloro-3-trifluoromethyl-phenyl, 4-chloro-2-trifluoromethyl-phenyl, 5-chloro-2-trifluoromethyl-phenyl, 2,3-dichloro-6-trifluoromethyl-phenyl, 2,4-dichloro-6-trifluoromethyl-phenyl, 2,6-dichloro-3-trifluoromethyl-phenyl, 3-fluoro-4-trifluoromethoxy-phenyl, 2-chloro-3-cyano-phenyl, 2,4-dichloro-6-cyano-phenyl, 2-methyl-phenyl, 4-methyl-phenyl, 2-methoxy-phenyl, 2,4-dimethoxy-phenyl, 3-trifluoromethyl-phenyl, 4-trifluoromethyl-phenyl, 2-cyano-phenyl, 4-cyano-phenyl and 4-phenoxy-phenyl. Further examples are 2-chloro-3,6-difluoro-phenyl, 3,6-dichloro-2-fluoro-phenyl, 2-fluoro-3-trifluoromethyl-phenyl, 2-chloro-3-difluoromethyl-phenyl, 2-chloro-4-trifluoromethyl-phenyl, 3-chloro-2-trifluoromethyl-phenyl, 2-chloro-3-trifluoromethoxy-phenyl, 2,4-dichloro-6-hydroxymethyl-phenyl, 2-chloro-4-cyano-phenyl, 2,4-dichloro-3-cyano-phenyl, 2-chloro-3-cyano-4-fluoro-phenyl, 3-cyano-2-trifluoromethyl-phenyl, 2-chloro-3-carbamoyl-phenyl and 2-chloro-3-acetyl-phenyl. Preferred examples are 2-chloro-4-fluoro-phenyl, 2,3-dichloro-phenyl, 2,4-dichloro-phenyl, 3,4-dichloro-phenyl, 2,3-dichloro-6-fluoro-phenyl, 2,4-dichloro-5-fluoro-phenyl, 2,4-dichloro-6-fluoro-phenyl, 2,4-dichloro-6-methyl-phenyl, 2,4-dichloro-6-ethyl-phenyl, 2,4-dichloro-6-cyclopropyl-phenyl, 4-fluoro-2-trifluoromethyl-phenyl, 2-chloro-3-trifluoromethyl-phenyl, 4-chloro-2-trifluoromethyl-phenyl, 2,4-dichloro-6-trifluoromethyl-phenyl, 2-chloro-3-cyano-phenyl and 2,4-dichloro-6-cyano-phenyl. In another embodiment the most preferred examples are 2-chloro-4-fluoro-phenyl, 2,3-dichloro-phenyl, 2,4-dichloro-phenyl, 2,4-dichloro-6-fluoro-phenyl, 2,4-dichloro-6-methyl-phenyl, 2,4-dichloro-6-ethyl-phenyl, 2,4-dichloro-6-cyclopropyl-phenyl, 2-chloro-3-trifluoromethyl-phenyl, 4-chloro-2-trifluoromethyl-phenyl, 2-chloro-3-cyano-phenyl, 2-fluoro-3-trifluoromethyl-phenyl, 2-chloro-3-difluoromethyl-phenyl, 2-chloro-4-trifluoromethyl-phenyl, 3-chloro-2-trifluoromethyl-phenyl, 2-chloro-3-trifluoromethoxy-phenyl, 2,4-dichloro-6-hydroxymethyl-phenyl, 2-chloro-4-cyano-phenyl, 2-chloro-3-cyano-4-fluoro-phenyl and 3-cyano-2-trifluoromethyl-phenyl.

The term "aryloxy", used alone or in combination, refers to an aryl-O— group wherein the aryl group is as defined above. Preferred is a phenoxy group. The aryloxy group is mono-, di-, tri- or tetra-substituted, wherein the substituents are independently selected from the group consisting of $(C_1-C_3)$alkyl, $(C_3-C_6)$cycloalkyl, $(C_1-C_3)$alkoxy, hydroxy-$(C_1-C_2)$alkyl, $(C_1-C_3)$fluoroalkyl, $(C_1-C_3)$fluoroalkoxy, $(C_1-C_2)$alkylcarbonyl, cyano, —$CONH_2$, halogen and phenoxy (notably from $(C_1-C_3)$alkyl, $(C_3-C_6)$cycloalkyl, $(C_1-C_3)$alkoxy, $(C_1-C_3)$fluoroalkyl, $(C_1-C_3)$fluoroalkoxy, cyano, halogen and phenoxy); preferably the aryloxy group is di- or tri-substituted, wherein the substituents are independently selected from the group consisting of $(C_1-C_3)$alkyl and halogen. Examples are 2,4-dichloro-phenoxy, 3,4-dichloro-phenoxy and 2,4-dimethyl-phenoxy.

The term "aryl-$(C_1-C_2)$alkyl" refers to a methyl or ethyl group in which groups one hydrogen atom has been replaced with aryl as defined before. Preferred is a benzyl group. The aryl moiety of the aryl-$(C_1-C_2)$alkyl group is mono-, di-, tri- or tetra-substituted (preferably mono-, di- or tri-substituted and most preferably di-substituted), wherein the substituents are independently selected from the group consisting of $(C_1-C_3)$alkyl, $(C_3-C_6)$cycloalkyl, $(C_1-C_3)$alkoxy, hydroxy-$(C_1-C_2)$alkyl, $(C_1-C_3)$fluoroalkyl, $(C_1-C_3)$fluoro-alkoxy, $(C_1-C_2)$alkylcarbonyl, cyano, —$CONH_2$, halogen and phenoxy (most preferably from halogen). Examples are 2-(4-fluorophenyl)-ethyl and 2,4-dichloro-benzyl.

The term "aryl-methyl" refers to a methyl group in which one hydrogen atom has been replaced with aryl as defined before. Preferred is a benzyl group. The aryl moiety of the aryl-methyl group is mono-, di-, tri- or tetra-substituted (preferably di- or tri-substituted and most preferably di-substituted), wherein the substituents are independently selected from the group consisting of $(C_1-C_3)$alkyl, $(C_3-C_6)$cycloalkyl, $(C_1-C_3)$alkoxy, $(C_1-C_3)$fluoroalkyl, $(C_1-C_3)$fluoroalkoxy, cyano, halogen and phenoxy; preferably the substituents are independently selected from the group consisting of $(C_1-C_3)$alkyl, $(C_1-C_3)$fluoroalkyl and halogen (most preferably from halogen). An example is 2,4-dichloro-benzyl.

The term "heteroaryl", used alone or in combination, means a 5- to 10-membered monocyclic or bicyclic aromatic ring containing 1, 2 or 3 heteroatoms independently selected from oxygen, nitrogen and sulfur. Preferred is a 5- or 6-membered monocyclic aromatic ring containing 1, 2 or 3 heteroatoms (preferably 1 or 2 heteroatoms) independently selected from oxygen, nitrogen and sulphur (preferably from oxygen and nitrogen). Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, cinnolinyl, quinazolinyl, quinoxalinyl and phthalazinyl. Preferred examples are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl and pyrazinyl. Most preferred are isoxazolyl, pyrazolyl and pyridyl. The heteroaryl groups are independently mono-, di-, tri- or tetra-substituted (preferably mono- or di-substituted and most preferably mono-substituted), wherein the substituents are independently selected from the group consisting of $(C_1-C_3)$alkyl, $(C_3-C_6)$cycloalkyl, $(C_1-C_3)$alkoxy, hydroxy-$(C_1-C_2)$alkyl, $(C_1-C_3)$fluoroalkyl, $(C_1-C_3)$fluoroalkoxy, $(C_1-C_2)$alkylcarbonyl, cyano, —$CONH_2$, halogen and phenoxy (notably from $(C_1-C_3)$alkyl, $(C_3-C_6)$cycloalkyl, $(C_1-C_3)$alkoxy, $(C_1-C_3)$fluoroalkyl, $(C_1-C_3)$fluoroalkoxy, cyano, halogen and phenoxy); preferably the substituents are independently selected from the group consisting of $(C_1-C_3)$alkyl and halogen (most preferably from methyl and chloro). Examples of such substituted heteroaryl groups are 3-methyl-isoxazolyl (notably 3-methyl-isoxazol-5-yl), 5-methyl-pyrazolyl (notably 5-methyl-1H-pyrazol-1-yl) and 2-chloro-pyridyl (notably 2-chloro-pyridin-3-yl). Preferred examples are 3-methyl-isoxazolyl (notably 3-methyl-isoxazol-5-yl) and 2-chloro-pyridyl (notably 2-chloro-pyridin-3-yl).

The term "heteroaryloxy", used alone or in combination, refers to an heteroaryl-O— group wherein the heteroaryl group is as defined above. A preferred meaning of the term "heteroaryl" as used in "heteroaryloxy" is a 5- or 6-membered monocyclic aromatic ring containing 1, 2 or 3 heteroatoms (preferably 1 or 2 heteroatoms) independently selected from oxygen, nitrogen and sulphur (preferably from oxygen and nitrogen). Examples of such heteroaryloxy groups are furanyloxy, oxazolyloxy, isoxazolyloxy, oxadiazolyloxy, thienyloxy, thiazolyloxy, isothiazolyloxy, thiadiazolyloxy, pyrrolyloxy, imidazolyloxy, pyrazolyloxy, triazolyloxy, pyridyloxy, pyrimidyloxy, pyridazinyloxy, pyrazinyloxy, indolyloxy, isoindolyloxy, benzofuranyloxy, isobenzofuranyloxy, benzothiophenyloxy, indazolyloxy, benzimidazolyloxy, benzoxazolyloxy, benzisoxazolyloxy, benzothiazolyloxy, benzoisothiazolyloxy, benzotriazolyloxy, benzo[2,1,3]oxadiazolyloxy, benzo[2,1,3]thiadiazolyloxy, benzo[1,2,3]thiadiazolyloxy, quinolinyloxy, isoquinolinyloxy, cinnolinyloxy, quinazolinyloxy, quinoxalinyloxy and phthalazinyloxy. Preferred examples are furanyloxy, oxazolyloxy, isoxazolyloxy, oxadiazolyloxy, thienyloxy, thiazolyloxy, isothiazolyloxy, thiadiazolyloxy, pyrrolyloxy, imidazolyloxy, pyrazolyloxy, triazolyloxy, pyridyloxy, pyrimidyloxy, pyridazinyloxy and pyrazinyloxy. Most preferred is pyridyloxy. The heteroaryloxy groups are independently mono-, di-, tri- or tetra-substituted (preferably mono- or di-substituted and most preferably di-substituted), wherein the substituents are independently selected from the group consisting of $(C_1-C_3)$alkyl, $(C_3-C_6)$cycloalkyl, $(C_1-C_3)$alkoxy, hydroxy-$(C_1-C_2)$alkyl, $(C_1-C_3)$fluoroalkyl, $(C_1-C_3)$fluoroalkoxy, $(C_1-C_2)$alkylcarbonyl, cyano, —$CONH_2$, halogen and phenoxy (notably from $(C_1-C_3)$alkyl, $(C_3-C_6)$cycloalkyl, $(C_1-C_3)$alkoxy, $(C_1-C_3)$fluoroalkyl, $(C_1-C_3)$fluoroalkoxy, cyano, halogen and phenoxy); preferably the substituents are independently selected from the group consisting of $(C_1-C_3)$alkyl and halogen (most preferably methyl). An example of such a substituted heteroaryl group is 2,6-dimethyl-pyridyloxy (notably 2,6-dimethyl-pyridin-3-yloxy).

The term "heterocyclyl-methyl", used alone or in combination, refers to a methyl group in which one hydrogen atom has been replaced with heterocyclyl; the term "heterocyclyl", used alone or in combination, refers to a saturated monocyclic moiety of 5 to 7 ring members (preferably 5 or 6 ring members) containing 1 or 2 heteroatoms (preferably 1 heteroatom) selected from nitrogen (preferred), oxygen and sulfur, it being understood that a heterocyclyl group does not contain 2 sulfur atoms. The sulfur atom of a heterocyclyl group may be in an oxidised form, i.e. as a sulfoxide or sulfonyl. Examples of such heterocyclyl groups are pyrrolidinyl (preferred), imidazolidinyl, oxazolidinyl, thiazolidinyl, piperidinyl, piperazinyl, morpholinyl, thiomorpholinyl and dioxanyl. Preferred examples of heterocyclyl-methyl groups are pyrrolidinyl-methyl (notably pyrrolidin-1-yl-methyl) and piperidinyl-methyl (notably piperidin-1-yl-methyl); most preferred is pyrrolidinyl-methyl (notably pyrrolidin-1-yl-methyl).

2) A further embodiment of the invention relates to compounds according to embodiment 1), wherein n represents 1 or 2;

one of X and Y represents —N— or —N(O)— (notably —N—) and the other one represents —N— or —C(R$^6$)—;

R$^1$ represents hydrogen and R$^2$ represents hydrogen, (C$_1$-C$_2$)alkyl, (C$_1$-C$_2$)deuteroalkyl or hydroxy-methyl; or R$^1$ and R$^2$ form, together with the carbon atom to which they are attached, a saturated carbocyclic ring of 3 to 6 members (notably 3 to 5 members); and R$^3$ represents an aryl group which is di- or tri-substituted, wherein the substituents are independently selected from the group consisting of (C$_1$-C$_3$)alkyl, (C$_3$-C$_6$)cycloalkyl, hydroxy-(C$_1$-C$_2$)alkyl, (C$_1$-C$_3$)fluoroalkyl, (C$_1$-C$_3$)fluoroalkoxy, (C$_1$-C$_2$)alkylcarbonyl, cyano, —CONH$_2$ and halogen; or an aryl-(C$_1$-C$_2$)alkyl group which is in the aromatic moiety mono- or di-substituted with halogen;

or

R$^1$ represents hydrogen and R$^2$ and R$^3$ form, together with the carbon atom to which they are attached, an indanyl group which is in the aromatic moiety mono- or di-substituted (notably di-substituted) with halogen; and R$^4$, R$^5$ and R$^6$ represent independently from each other hydrogen, (C$_1$-C$_3$)alkyl, (C$_3$-C$_6$)cycloalkyl, methoxy, trifluoromethyl or halogen;

and to the salts (in particular pharmaceutically acceptable salts) of such compounds.

3) A further embodiment of the invention relates to compounds according to embodiment 1), wherein n represents 1 or 2;

one of X and Y represents —N— or —N(O)— (notably —N—) and the other one represents —N— or —C(R$^6$)—;

R$^1$ represents hydrogen and R$^2$ represents hydrogen, (C$_1$-C$_2$)alkyl, (C$_1$-C$_2$)deuteroalkyl or hydroxy-methyl; or R$^1$ and R$^2$ form, together with the carbon atom to which they are attached, a saturated carbocyclic ring of 3 to 5 members; and R$^3$ represents an aryl group which is di- or tri-substituted, wherein the substituents are independently selected from the group consisting of (C$_1$-C$_3$)alkyl, (C$_3$-C$_6$)cycloalkyl, hydroxy-(C$_1$-C$_2$)alkyl, (C$_1$-C$_3$)fluoroalkyl, (C$_1$-C$_3$)fluoroalkoxy, cyano and halogen;

or

R$^1$ represents hydrogen and R$^2$ and R$^3$ form, together with the carbon atom to which they are attached, an indanyl group which is in the aromatic moiety mono- or di-substituted (notably di-substituted) with halogen;

R$^4$ represents hydrogen, (C$_1$-C$_3$)alkyl or halogen;

R$^5$ represents hydrogen, (C$_1$-C$_3$)alkyl, (C$_3$-C$_6$)cycloalkyl, methoxy or trifluoromethyl; and R$^6$ represents hydrogen, (C$_1$-C$_3$)alkyl, (C$_3$-C$_6$)cycloalkyl, methoxy or halogen; and to the salts (in particular pharmaceutically acceptable salts) of such compounds.

4) A further embodiment of the invention relates to compounds according to embodiment 1), wherein n represents 1 or 2;

one of X and Y represents —N— or —N(O)— (notably —N—) and the other one represents —N— or —C(R$^6$)—;

R$^1$ represents hydrogen;

R$^2$ represents hydrogen, methyl or hydroxy-methyl (notably hydrogen);

R$^3$ represents an aryl group which is di- or tri-substituted, wherein the substituents are independently selected from the group consisting of (C$_1$-C$_3$)alkyl, (C$_1$-C$_3$)fluoroalkyl and halogen;

R$^4$ represents hydrogen, (C$_1$-C$_3$)alkyl or halogen;

R$^5$ represents hydrogen, (C$_1$-C$_3$)alkyl, (C$_3$-C$_6$)cycloalkyl, methoxy or trifluoromethyl (notably hydrogen, (C$_1$-C$_3$)alkyl or (C$_3$-C$_6$)cycloalkyl); and R$^6$ represents hydrogen, (C$_1$-C$_3$)alkyl, (C$_3$-C$_6$)cycloalkyl, methoxy or halogen;

and to the salts (in particular pharmaceutically acceptable salts) of such compounds.

5) A further embodiment of the invention relates to compounds according to embodiment 1), wherein n represents 1 or 2;

X represents —N— or —N(O)—;

Y represents —C(R$^6$)— or —N— (notably —C(R$^6$)—);

R$^1$ represents hydrogen or methyl and R$^2$ represents hydrogen, (C$_1$-C$_2$)alkyl, (C$_1$-C$_2$)deuteroalkyl, hydroxy-methyl or heterocyclyl-methyl; or R$^1$ and R$^2$ form, together with the carbon atom to which they are attached, a saturated carbocyclic ring of 3 to 6 members; and R$^3$ represents an aryl, an aryl-(C$_1$-C$_2$)alkyl, a heteroaryl or a heteroaryloxy group which groups are in the aromatic moiety independently mono-, di-, tri- or tetra-substituted, wherein the substituents are independently selected from the group consisting of (C$_1$-C$_3$)alkyl, (C$_3$-C$_6$)cycloalkyl, (C$_1$-C$_3$)alkoxy, hydroxy-(C$_1$-C$_2$)alkyl, (C$_1$-C$_3$)fluoroalkyl, (C$_1$-C$_3$)fluoroalkoxy, (C$_1$-C$_2$)alkylcarbonyl, cyano, —CONH$_2$, halogen and phenoxy;

or

R$^1$ represents hydrogen and R$^2$ and R$^3$ form, together with the carbon atom to which they are attached, an indanyl or a tetrahydronaphthyl group (notably indanyl) which groups are in the aromatic moiety independently mono-, di- or tri-substituted (notably di-substituted), wherein the substituents are independently selected from the group consisting of (C$_1$-C$_3$)alkyl, (C$_1$-C$_3$)fluoroalkyl and halogen (notably from halogen); and R$^4$, R$^5$ and R$^6$ represent independently from each other hydrogen, (C$_1$-C$_3$)alkyl, (C$_1$-C$_3$)alkoxy, (C$_1$-C$_3$)fluoroalkyl or halogen;

and to the salts (in particular pharmaceutically acceptable salts) of such compounds.

6) A further embodiment of the invention relates to compounds according to embodiment 1) that are also compounds of formula (I$_P$)

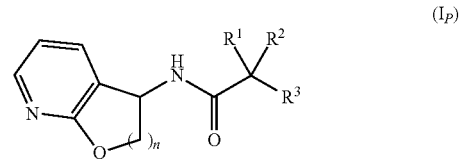

(I$_P$)

wherein n represents 1 or 2;

R$^1$ and R$^2$ independently represent hydrogen or methyl; or

R$^1$ and R$^2$ form, together with the carbon atom to which they are attached, a saturated carbocyclic ring of 3 to 6 members; and R$^3$ represents an aryl, an aryloxy, an aryl-methyl, a heteroaryl or a heteroaryloxy group which groups are in the aromatic moiety independently mono-, di-, tri- or tetra-substituted, wherein the substituents are independently selected from the group consisting of $(C_1-C_3)$alkyl, $(C_3-C_6)$cycloalkyl, $(C_1-C_3)$alkoxy, $(C_1-C_3)$fluoroalkyl, $(C_1-C_3)$fluoroalkoxy, cyano, halogen and phenoxy;
and to the salts (in particular pharmaceutically acceptable salts) of such compounds.

7) A further embodiment of the invention relates to compounds according to embodiment 1), wherein
n represents 1 or 2;
X represents —N— or —N(O)—;
Y represents —C($R^6$)— or —N— (notably —C($R^6$)—);
$R^1$ represents hydrogen and $R^2$ represents hydrogen, $(C_1-C_2)$alkyl or hydroxy-methyl; or
$R^1$ and $R^2$ form, together with the carbon atom to which they are attached, a saturated carbocyclic ring of 3 to 5 members; and
$R^3$ represents an aryl group which is di- or tri-substituted, wherein the substituents are independently selected from the group consisting of $(C_1-C_3)$alkyl, $(C_3-C_6)$cycloalkyl, hydroxy-$(C_1-C_2)$alkyl, $(C_1-C_3)$fluoroalkyl, $(C_1-C_3)$fluoroalkoxy, $(C_1-C_2)$alkylcarbonyl, cyano, —$CONH_2$ and halogen; or an aryl-$(C_1-C_2)$alkyl group which is in the aromatic moiety mono- or di-substituted with halogen;
or
$R^1$ represents hydrogen and $R^2$ and $R^3$ form, together with the carbon atom to which they are attached, an indanyl group which is in the aromatic moiety mono- or di-substituted (notably di-substituted) with halogen; and
$R^4$, $R^5$ and $R^6$ represent independently from each other hydrogen, $(C_1-C_3)$alkyl, $(C_1-C_3)$alkoxy, $(C_1-C_3)$fluoroalkyl or halogen;
and to the salts (in particular pharmaceutically acceptable salts) of such compounds.

8) A further embodiment of the invention relates to compounds according to embodiment 1), wherein
n represents 1 or 2;
X represents —N—;
Y represents —C($R^6$)— or —N—;
$R^1$ represents hydrogen and $R^2$ represents hydrogen, $(C_1-C_2)$alkyl or hydroxy-methyl; or
$R^1$ and $R^2$ form, together with the carbon atom to which they are attached, a saturated carbocyclic ring of 3 to 5 members; and
$R^3$ represents an aryl group which is di- or tri-substituted, wherein the substituents are independently selected from the group consisting of methyl, ethyl, cyclopropyl, hydroxy-methyl, difluoromethyl, trifluoromethyl, trifluoromethoxy, cyano, fluoro and chloro;
or
$R^1$ represents hydrogen and $R^2$ and $R^3$ form, together with the carbon atom to which they are attached, an indanyl group which is in the aromatic moiety di-substituted with chloro;
$R^4$ represents hydrogen;
$R^5$ represents hydrogen or methyl; and
$R^6$ represents hydrogen, methyl or chloro; and to the salts (in particular pharmaceutically acceptable salts) of such compounds.

9) A further embodiment of the invention relates to compounds according to embodiment 1), wherein
n represents 1 or 2;
X represents —C($R^6$)—;
Y represents —N— or —N(O)—;
$R^1$ represents hydrogen;
$R^2$ represents hydrogen or methyl;
$R^3$ represents an aryl group which is di- or tri-substituted, wherein the substituents are independently selected from the group consisting of $(C_1-C_3)$alkyl, cyclopropyl, hydroxy-methyl, $(C_1-C_3)$fluoroalkyl and halogen (notably $(C_1-C_3)$alkyl, $(C_1-C_3)$fluoroalkyl and halogen);
$R^4$, $R^5$ and $R^6$ represent independently from each other hydrogen, $(C_1-C_3)$alkyl, $(C_3-C_6)$cycloalkyl, $(C_1-C_3)$alkoxy or halogen;
and to the salts (in particular pharmaceutically acceptable salts) of such compounds.

10) A further embodiment of the invention relates to compounds according to embodiment 1), wherein
n represents 1 or 2 (notably 1);
X represents —C($R^6$)—;
Y represents —N— or —N(O)—;
$R^1$ represents hydrogen;
$R^2$ represents hydrogen;
$R^3$ represents an aryl group which is di- or tri-substituted, wherein the substituents are independently selected from the group consisting of $(C_1-C_3)$alkyl, $(C_1-C_3)$fluoroalkyl and halogen (notably methyl, trifluoromethyl and chloro);
$R^4$ represents hydrogen, $(C_1-C_3)$alkyl or halogen;
$R^5$ represents hydrogen, $(C_1-C_3)$alkyl or $(C_3-C_6)$cycloalkyl;
$R^6$ represents hydrogen, $(C_1-C_3)$alkyl, $(C_3-C_6)$cycloalkyl, $(C_1-C_3)$alkoxy or halogen;
and to the salts (in particular pharmaceutically acceptable salts) of such compounds.

11) A further embodiment of the invention relates to compounds according to any one of embodiments 1), 5) or 6), wherein
n represents 1 or 2;
$R^1$ and $R^2$ independently represent hydrogen or methyl; or
$R^1$ and $R^2$ form, together with the carbon atom to which they are attached, a saturated carbocyclic ring of 3 to 5 members; and
$R^3$ represents an aryl, an aryl-methyl, a heteroaryl or a heteroaryloxy group which groups are in the aromatic moiety independently mono-, di-, tri- or tetra-substituted, wherein the substituents are independently selected from the group consisting of $(C_1-C_3)$alkyl, $(C_3-C_6)$cycloalkyl, $(C_1-C_3)$alkoxy, $(C_1-C_3)$fluoroalkyl, $(C_1-C_3)$fluoroalkoxy, cyano, halogen and phenoxy;
and to the salts (in particular pharmaceutically acceptable salts) of such compounds.

12) A further embodiment of the invention relates to compounds according to any one of embodiments 1), 5) or 6), wherein
n represents 1 or 2;
$R^1$ and $R^2$ represent hydrogen; or
$R^1$ and $R^2$ form, together with the carbon atom to which they are attached, a saturated carbocyclic ring of 3 to 5 members; and
$R^3$ represents an aryl group which is mono-, di-, tri- or tetra-substituted, wherein the substituents are independently selected from the group consisting of $(C_1-C_3)$alkyl, $(C_3-C_6)$cycloalkyl (notably cyclopropyl), $(C_1-C_3)$fluoroalkyl (notably trifluoromethyl), cyano and halogen;
and to the salts (in particular pharmaceutically acceptable salts) of such compounds.

13) A further embodiment of the invention relates to compounds according to any one of embodiments 1) to 3) or 5) to 7), wherein
n represents 1 or 2;
$R^1$ and $R^2$ represent hydrogen; and
$R^3$ represents an aryl group (notably phenyl) which is di- or tri-substituted, wherein the substituents are independently selected from the group consisting of $(C_1-C_3)$alkyl, cyclopropyl, trifluoromethyl, cyano and halogen;
and to the salts (in particular pharmaceutically acceptable salts) of such compounds.

14) A further embodiment of the invention relates to compounds according to any one of embodiments 1) to 13), wherein
n represents 1;
and to the salts (in particular pharmaceutically acceptable salts) of such compounds.

15) A further embodiment of the invention relates to compounds according to any one of embodiments 1) to 13), wherein
n represents 2;
and to the salts (in particular pharmaceutically acceptable salts) of such compounds.

16) A further embodiment of the invention relates to compounds according to any one of embodiments 1) to 5), 7), 8), 14) or 15), wherein
X represents —N— and Y represents —C($R^6$)— or —N—;
and to the salts (in particular pharmaceutically acceptable salts) of such compounds.

17) A further embodiment of the invention relates to compounds according to any one of embodiments 1) to 5), 7), 8), 14) or 15), wherein
X represents —N— and Y represents —C($R^6$)—;
and to the salts (in particular pharmaceutically acceptable salts) of such compounds.

18) A further embodiment of the invention relates to compounds according to any one of embodiments 1) to 5), 7), 8), 14) or 15), wherein
X represents —N— and Y represents —N—;
and to the salts (in particular pharmaceutically acceptable salts) of such compounds.

19) A further embodiment of the invention relates to compounds according to any one of embodiments 1) to 4), 14) or 15), wherein
X represents —C($R^6$)— or —N— and Y represents —N—;
and to the salts (in particular pharmaceutically acceptable salts) of such compounds.

20) A further embodiment of the invention relates to compounds according to any one of embodiments 1) to 4), 9), 10), 14) or 15), wherein
X represents —C($R^6$)— and Y represents —N—;
and to the salts (in particular pharmaceutically acceptable salts) of such compounds.

21) A further embodiment of the invention relates to compounds according to any one of embodiments 1) to 4), 14) or 15), wherein
one of X and Y represents —N— or —N(O)— and the other one represents —C($R^6$)—;
and to the salts (in particular pharmaceutically acceptable salts) of such compounds.

22) A further embodiment of the invention relates to compounds according to any one of embodiments 1) to 3), 5), 7), 8) or 14) to 21), wherein
$R^1$ represents hydrogen and $R^2$ represents hydrogen, methyl, ethyl or hydroxy-methyl; or
$R^1$ and $R^2$ form, together with the carbon atom to which they are attached, a saturated carbocyclic ring of 3 to 5 members; and
$R^3$ represents a phenyl group which is di- or tri-substituted, wherein the substituents are independently selected from the group consisting of methyl, ethyl, cyclopropyl, hydroxy-methyl, difluoromethyl, trifluoromethyl, trifluoromethoxy, cyano, fluoro and chloro;
or
$R^1$ represents hydrogen and $R^2$ and $R^3$ form, together with the carbon atom to which they are attached, an indanyl group which is in the aromatic moiety di-substituted with chloro;
and to the salts (in particular pharmaceutically acceptable salts) of such compounds.

23) A further embodiment of the invention relates to compounds according to any one of embodiments 1), 5) or 14) to 21), wherein
$R^1$ represents hydrogen or methyl and $R^2$ represents hydrogen, ($C_1$-$C_2$)alkyl, ($C_1$-$C_2$)deuteroalkyl, hydroxy-methyl or heterocyclyl-methyl; or
$R^1$ and $R^2$ form, together with the carbon atom to which they are attached, a saturated carbocyclic ring of 3 to 5 members; and
$R^3$ represents an aryl, an aryl-($C_1$-$C_2$)alkyl, a heteroaryl or a heteroaryloxy group which groups are in the aromatic moiety independently di-, tri- or tetra-substituted, wherein the substituents are independently selected from the group consisting of ($C_1$-$C_3$)alkyl, ($C_3$-$C_6$)cycloalkyl, ($C_1$-$C_3$)alkoxy, hydroxy-($C_1$-$C_2$)alkyl, ($C_1$-$C_3$)fluoroalkyl, ($C_1$-$C_3$)fluoroalkoxy, ($C_1$-$C_2$)alkylcarbonyl, cyano, —CONH$_2$ and halogen;
and to the salts (in particular pharmaceutically acceptable salts) of such compounds.

24) A further embodiment of the invention relates to compounds according to any one of embodiments 1) to 3), 5), 7), 8) or 14) to 21), wherein
$R^1$ represents hydrogen and $R^2$ represents hydrogen, methyl, ethyl or hydroxy-methyl; or
$R^1$ and $R^2$ form, together with the carbon atom to which they are attached, a saturated carbocyclic ring of 3 to 5 members; and
$R^3$ represents a phenyl group which is di- or tri-substituted, wherein the substituents are independently selected from the group consisting of methyl, ethyl, cyclopropyl, hydroxy-methyl, difluoromethyl, trifluoromethyl, trifluoromethoxy, cyano, fluoro and chloro; and to the salts (in particular pharmaceutically acceptable salts) of such compounds.

25) A further embodiment of the invention relates to compounds according to any one of embodiments 1), 5) or 14) to 21), wherein
$R^1$ represents hydrogen and $R^2$ and $R^3$ form, together with the carbon atom to which they are attached, an indanyl or a tetrahydronaphthyl group (notably indanyl) which groups are in the aromatic moiety independently mono-, di- or tri-substituted (notably di-substituted), wherein the substituents are independently selected from the group consisting of ($C_1$-$C_3$)alkyl, ($C_1$-$C_3$)fluoroalkyl and halogen (notably from halogen);
and to the salts (in particular pharmaceutically acceptable salts) of such compounds.

26) A further embodiment of the invention relates to compounds according to any one of embodiments 1) to 3), 5), 7) or 14) to 21), wherein
$R^1$ represents hydrogen and $R^2$ and $R^3$ form, together with the carbon atom to which they are attached, an indanyl group which is in the aromatic moiety mono- or di-substituted (notably di-substituted) with halogen;
and to the salts (in particular pharmaceutically acceptable salts) of such compounds.

27) A further embodiment of the invention relates to compounds according to any one of embodiments 1), 5), 6), 11), 14) to 21) or 23), wherein
$R^1$ and $R^2$ independently represent hydrogen or methyl; and to the salts (in particular pharmaceutically acceptable salts) of such compounds.

28) A further embodiment of the invention relates to compounds according to any one of embodiments 1) to 24), wherein $R^1$ and $R^2$ represent hydrogen;
and to the salts (in particular pharmaceutically acceptable salts) of such compounds.

29) A further embodiment of the invention relates to compounds according to any one of embodiments 1) to 3), 5) to 8), 11), 12) or 14) to 24), wherein
$R^1$ and $R^2$ represent hydrogen; or
$R^1$ and $R^2$ form, together with the carbon atom to which they are attached, a saturated carbocyclic ring of 3 to 5 members;
and to the salts (in particular pharmaceutically acceptable salts) of such compounds.

30) A further embodiment of the invention relates to compounds according to any one of embodiments 1) to 3), 5) to 8), 11), 12) or 14) to 24), wherein
$R^1$ and $R^2$ form, together with the carbon atom to which they are attached, a saturated carbocyclic ring of 3 to 5 members;
and to the salts (in particular pharmaceutically acceptable salts) of such compounds.

31) A further embodiment of the invention relates to compounds according to any one of embodiments 1) to 26), wherein
$R^1$ represents hydrogen;
and to the salts (in particular pharmaceutically acceptable salts) of such compounds.

32) A further embodiment of the invention relates to compounds according to any one of embodiments 1) to 3), 5), 7), 8) or 14) to 24), wherein
$R^2$ represents hydrogen, methyl, ethyl, trideuteromethyl or hydroxy-methyl (notably hydrogen, methyl, ethyl or hydroxy-methyl);
and to the salts (in particular pharmaceutically acceptable salts) of such compounds.

33) A further embodiment of the invention relates to compounds according to any one of embodiments 1) to 9), 11) or 14) to 24), wherein
$R^2$ represents hydrogen or methyl;
and to the salts (in particular pharmaceutically acceptable salts) of such compounds.

34) A further embodiment of the invention relates to compounds according to any one of embodiments 1) to 3), 5), 14) to 21) or 23), wherein
$R^2$ represents trideuteromethyl;
and to the salts (in particular pharmaceutically acceptable salts) of such compounds.

35) A further embodiment of the invention relates to compounds according to any one of embodiments 1), 5), 14) to 21) or 27) to 34), wherein
$R^3$ represents an aryl, an aryl-$(C_1$-$C_2)$alkyl, a heteroaryl or a heteroaryloxy group which groups are in the aromatic moiety independently mono-, di-, tri- or tetra-substituted, wherein the substituents are independently selected from the group consisting of $(C_1$-$C_3)$alkyl, $(C_3$-$C_6)$cycloalkyl, $(C_1$-$C_3)$alkoxy, hydroxy-$(C_1$-$C_2)$alkyl, $(C_1$-$C_3)$fluoroalkyl, $(C_1$-$C_3)$fluoroalkoxy, $(C_1$-$C_2)$alkylcarbonyl, cyano, —$CONH_2$, halogen and phenoxy;
and to the salts (in particular pharmaceutically acceptable salts) of such compounds.

36) A further embodiment of the invention relates to compounds according to any one of embodiments 1), 5), 14) to 21) or 27) to 34), wherein
$R^3$ represents a phenyl group which is di-, tri- or tetra-substituted, wherein the substituents are independently selected from the group consisting of $(C_1$-$C_3)$alkyl, $(C_3$-$C_6)$cycloalkyl, $(C_1$-$C_3)$alkoxy, hydroxy-$(C_1$-$C_2)$alkyl, $(C_1$-$C_3)$fluoroalkyl, $(C_1$-$C_3)$fluoroalkoxy, $(C_1$-$C_2)$alkylcarbonyl, cyano, —$CONH_2$ and halogen; a phenyl-methyl or phenyl-ethyl group which groups are in the aromatic moiety independently mono- or di-substituted with halogen; a heteroaryl group which is mono- or di-substituted, wherein the substituents are independently selected from the group consisting of $(C_1$-$C_3)$alkyl and halogen; or a heteroaryloxy group which is mono- or di-substituted with $(C_1$-$C_3)$alkyl;
and to the salts (in particular pharmaceutically acceptable salts) of such compounds.

37) A further embodiment of the invention relates to compounds according to any one of embodiments 1), 5), 6), 11), 14) to 21) or 27) to 34), wherein
$R^3$ represents an aryl or a heteroaryl group which groups are independently mono-, di- or tri-substituted (notably di- or tri-substituted), wherein the substituents are independently selected from the group consisting of $(C_1$-$C_3)$alkyl, $(C_3$-$C_6)$cycloalkyl (notably cyclopropyl), $(C_1$-$C_3)$fluoroalkyl (notably trifluoromethyl), cyano and halogen;
and to the salts (in particular pharmaceutically acceptable salts) of such compounds.

38) A further embodiment of the invention relates to compounds according to any one of embodiments 1), 5), 6), 11), 12), 14) to 21) or 27) to 34), wherein
$R^3$ represents an aryl group which is mono-, di- or tri-substituted (notably di- or tri-substituted), wherein the substituents are independently selected from the group consisting of $(C_1$-$C_3)$alkyl, $(C_3$-$C_6)$cycloalkyl (notably cyclopropyl), $(C_1$-$C_3)$fluoroalkyl (notably trifluoromethyl), cyano and halogen;
and to the salts (in particular pharmaceutically acceptable salts) of such compounds.

39) A further embodiment of the invention relates to compounds according to any one of embodiments 1) to 3), 5) to 7), 11) to 21), 23) or 27) to 34), wherein
$R^3$ represents an aryl group (notably phenyl) which is di- or tri-substituted, wherein the substituents are independently selected from the group consisting of $(C_1$-$C_3)$alkyl, cyclopropyl, trifluoromethyl, cyano and halogen;
and to the salts (in particular pharmaceutically acceptable salts) of such compounds.

40) A further embodiment of the invention relates to compounds according to any one of embodiments 1) to 3), 5) to 8), 11) to 24) or 27) to 34), wherein
$R^3$ represents 2-chloro-phenyl which is additionally mono- or di-substituted, wherein the substituents are independently selected from the group consisting of $(C_1$-$C_3)$alkyl, cyclopropyl, trifluoromethyl, cyano and halogen (and notably from methyl, ethyl, cyclopropyl, trifluoromethyl, chloro and fluoro);
and to the salts (in particular pharmaceutically acceptable salts) of such compounds.

41) A further embodiment of the invention relates to compounds according to any one of embodiments 1) to 3), 5), 7), 8), 14) to 24) or 27) to 34), wherein
$R^3$ represents a phenyl group which is di- or tri-substituted, wherein the substituents are independently selected from the group consisting of methyl, ethyl, cyclopropyl, hydroxy-methyl, difluoromethyl, trifluoromethyl, trifluoromethoxy, cyano, fluoro and chloro;
and to the salts (in particular pharmaceutically acceptable salts) of such compounds.

42) A further embodiment of the invention relates to compounds according to any one of embodiments 1) to 5), 7) or 9) to 41), wherein
$R^4$ represents hydrogen, $(C_1$-$C_3)$alkyl or halogen (notably hydrogen, methyl or chloro);
and to the salts (in particular pharmaceutically acceptable salts) of such compounds.

43) A further embodiment of the invention relates to compounds according to any one of embodiments 1) to 5) or 7) to 41), wherein
$R^4$ represents hydrogen;
and to the salts (in particular pharmaceutically acceptable salts) of such compounds.

44) A further embodiment of the invention relates to compounds according to any one of embodiments 1) to 4) or 11) to 43), wherein
$R^5$ represents hydrogen, $(C_1-C_3)$alkyl, $(C_3-C_6)$cycloalkyl, methoxy or trifluoromethyl;
and to the salts (in particular pharmaceutically acceptable salts) of such compounds.

45) A further embodiment of the invention relates to compounds according to any one of embodiments 1) to 5) or 7) to 43), wherein
$R^5$ represents hydrogen or methyl;
and to the salts (in particular pharmaceutically acceptable salts) of such compounds.

46) A further embodiment of the invention relates to compounds according to any one of embodiments 1) to 4) or 9) to 45), wherein
$R^6$ represents hydrogen, $(C_1-C_3)$alkyl, $(C_3-C_6)$cycloalkyl or halogen;
and to the salts (in particular pharmaceutically acceptable salts) of such compounds.

47) A further embodiment of the invention relates to compounds according to any one of embodiments 1) to 5) or 7) to 45), wherein
$R^6$ represents hydrogen, methyl or chloro;
and to the salts (in particular pharmaceutically acceptable salts) of such compounds.

48) A further embodiment of the invention relates to compounds according to any one of embodiments 1) to 47), wherein the absolute configuration of the stereogenic center is as depicted in formula ($I_{St1}$)

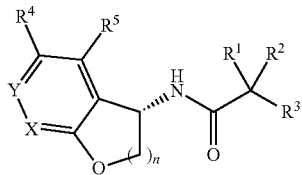

(I$_{St1}$)

and to the salts (in particular pharmaceutically acceptable salts) of such compounds.

49) A further embodiment of the invention relates to compounds according to any one of embodiments 6), 11) to 15), 27) to 30) or 37) to 40), wherein the absolute configuration of the stereogenic center is as depicted in formula ($I_{St1-P}$)

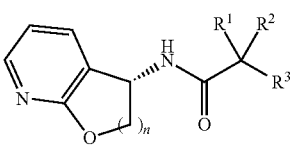

(I$_{St1-P}$)

and to the salts (in particular pharmaceutically acceptable salts) of such compounds.

50) A further embodiment of the invention relates to compounds according to any one of embodiments 1) to 47), wherein the absolute configuration of the stereogenic center is as depicted in formula ($I_{St2}$)

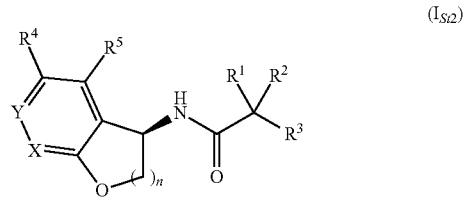

(I$_{St2}$)

and to the salts (in particular pharmaceutically acceptable salts) of such compounds.

51) A further embodiment of the invention relates to compounds according to any one of embodiments 6), 11) to 15), 27) to 30) or 37) to 40), wherein the absolute configuration of the stereogenic center is as depicted in formula ($I_{St2-P}$)

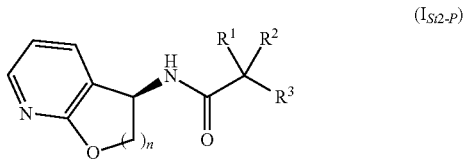

(I$_{St2-P}$)

and to the salts (in particular pharmaceutically acceptable salts) of such compounds.

52) Preferred compounds of formula (I) as defined in embodiment 1) are selected from the group consisting of:
2-(2,4-Dichloro-phenyl)-N-(2,3-dihydro-furo[2,3-b]pyridin-3-yl)-acetamide;
2-(2-Chloro-4-fluoro-phenyl)-N-(2,3-dihydro-furo[2,3-b]pyridin-3-yl)-acetamide;
2-(2,4-Dichloro-phenyl)-N—(S)-(2,3-dihydro-furo[2,3-b]pyridin-3-yl)-acetamide;
2-(2,4-Dichloro-phenyl)-N—(R)-(2,3-dihydro-furo[2,3-b]pyridin-3-yl)-acetamide;
2-(2,4-Dichloro-6-methyl-phenyl)-N-(2,3-dihydro-furo[2,3-b]pyridin-3-yl)-acetamide;
2-(2,4-Dichloro-6-methyl-phenyl)-N—(S)-(2,3-dihydro-furo[2,3-b]pyridin-3-yl)-acetamide;
2-(2,4-Dichloro-6-methyl-phenyl)-N—(R)-(2,3-dihydro-furo[2,3-b]pyridin-3-yl)-acetamide;
2-(2,4-Dichloro-6-methyl-phenyl)-N-(3,4-dihydro-2H-pyrano[2,3-b]pyridin-4-yl)-acetamide;
2-(2,4-Dichloro-phenyl)-N-(3,4-dihydro-2H-pyrano[2,3-b]pyridin-4-yl)-acetamide;
2-(2-Cyano-phenyl)-N-(2,3-dihydro-furo[2,3-b]pyridin-3-yl)-acetamide;
N-(2,3-Dihydro-furo[2,3-b]pyridin-3-yl)-2-o-tolyl-acetamide;
N-(2,3-Dihydro-furo[2,3-b]pyridin-3-yl)-2-(2-methoxyphenyl)-acetamide;
2-(4-Cyano-phenyl)-N-(2,3-dihydro-furo[2,3-b]pyridin-3-yl)-acetamide;
N-(2,3-Dihydro-furo[2,3-b]pyridin-3-yl)-2-p-tolyl-acetamide;
2-(4-Chloro-phenyl)-N-(2,3-dihydro-furo[2,3-b]pyridin-3-yl)-acetamide;
N-(2,3-Dihydro-furo[2,3-b]pyridin-3-yl)-2-(4-trifluoromethyl-phenyl)-acetamide;
2-(2,4-Difluoro-phenyl)-N-(2,3-dihydro-furo[2,3-b]pyridin-3-yl)-acetamide;

N-(2,3-Dihydro-furo[2,3-b]pyridin-3-yl)-2-(4-fluoro-2-trifluoromethyl-phenyl)-acetamide;
N-(2,3-Dihydro-furo[2,3-b]pyridin-3-yl)-2-(2,4-dimethoxyphenyl)-acetamide;
N-(2,3-Dihydro-furo[2,3-b]pyridin-3-yl)-2-(2-fluoro-4-methoxy-phenyl)-acetamide;
2-(3,4-Dichloro-phenyl)-N-(2,3-dihydro-furo[2,3-b]pyridin-3-yl)-acetamide;
N-(2,3-Dihydro-furo[2,3-b]pyridin-3-yl)-2-(2,4,6-trifluorophenyl)-acetamide;
2-(4-Chloro-phenyl)-N-(2,3-dihydro-furo[2,3-b]pyridin-3-yl)-propionamide;
1-(2,4-Dichloro-phenyl)-cyclopropanecarboxylic acid (2,3-dihydro-furo[2,3-b]pyridin-3-yl)-amide;
1-(2-Chloro-4-fluoro-phenyl)-cyclopentanecarboxylic acid (2,3-dihydro-furo[2,3-b]pyridin-3-yl)-amide;
2-(4-Chloro-phenyl)-N-(2,3-dihydro-furo[2,3-b]pyridin-3-yl)-isobutyramide;
3-(2,4-Dichloro-phenyl)-N-(2,3-dihydro-furo[2,3-b]pyridin-3-yl)-propionamide;
2-(2,4-Dichloro-6-methyl-phenyl)-N—(S)-(3,4-dihydro-2H-pyrano[2,3-b]pyridin-4-yl)-acetamide;
2-(2,4-Dichloro-6-methyl-phenyl)-N—(R)-(3,4-dihydro-2H-pyrano[2,3-b]pyridin-4-yl)-acetamide;
2-(2,4-Dichloro-phenyl)-N—(S)-(3,4-dihydro-2H-pyrano[2,3-b]pyridin-4-yl)-acetamide;
2-(2,4-Dichloro-phenyl)-N—(R)-(3,4-dihydro-2H-pyrano[2,3-b]pyridin-4-yl)-acetamide;
2-(2,4-Dichloro-6-ethyl-phenyl)-N-(2,3-dihydro-furo[2,3-b]pyridin-3-yl)-acetamide;
2-(2,4-Dichloro-6-trifluoromethyl-phenyl)-N-(2,3-dihydro-furo[2,3-b]pyridin-3-yl)-acetamide;
2-(2-Chloro-3-trifluoromethyl-phenyl)-N-(2,3-dihydro-furo[2,3-b]pyridin-3-yl)-acetamide;
2-(4-Chloro-2-trifluoromethyl-phenyl)-N-(2,3-dihydro-furo[2,3-b]pyridin-3-yl)-acetamide;
N-(2,3-Dihydro-furo[2,3-b]pyridin-3-yl)-2-(4-phenoxyphenyl)-acetamide;
2-(2,4-Dichloro-6-cyano-phenyl)-N-(2,3-dihydro-furo[2,3-b]pyridin-3-yl)-acetamide;
2-(2-Chloro-4-fluoro-phenyl)-N-(3,4-dihydro-2H-pyrano[2,3-b]pyridin-4-yl)-acetamide;
2-(2,4-Dichloro-6-cyclopropyl-phenyl)-N-(2,3-dihydro-furo[2,3-b]pyridin-3-yl)-acetamide;
2-(4-Chloro-2-fluoro-3-methyl-6-trifluoromethyl-phenyl)-N-(2,3-dihydro-furo[2,3-b]pyridin-3-yl)-acetamide;
2-(2,4-Dichloro-5-fluoro-phenyl)-N-(2,3-dihydro-furo[2,3-b]pyridin-3-yl)-acetamide;
2-(2-Chloro-6-fluoro-3-methyl-phenyl)-N-(2,3-dihydrofuro[2,3-b]pyridin-3-yl)-acetamide;
2-(5-Chloro-2-trifluoromethyl-phenyl)-N-(2,3-dihydro-furo[2,3-b]pyridin-3-yl)-acetamide;
2-(2-Chloro-phenyl)-N-(3,4-dihydro-2H-pyrano[2,3-b]pyridin-4-yl)-acetamide;
2-(4-Cyano-phenyl)-N-(3,4-dihydro-2H-pyrano[2,3-b]pyridin-4-yl)-acetamide;
N-(3,4-Dihydro-2H-pyrano[2,3-b]pyridin-4-yl)-2-(4-trifluoromethyl-phenyl)-acetamide;
N-(3,4-Dihydro-2H-pyrano[2,3-b]pyridin-4-yl)-2-(3-trifluoromethyl-phenyl)-acetamide;
N-(3,4-Dihydro-2H-pyrano[2,3-b]pyridin-4-yl)-2-(4-phenoxy-phenyl)-acetamide;
2-(2-Chloro-3-trifluoromethyl-phenyl)-N-(3,4-dihydro-2H-pyrano[2,3-b]pyridin-4-yl)-acetamide;
2-(2-Chloro-6-fluoro-phenyl)-N-(3,4-dihydro-2H-pyrano[2,3-b]pyridin-4-yl)-acetamide;
2-(2,4-Difluoro-phenyl)-N-(3,4-dihydro-2H-pyrano[2,3-b]pyridin-4-yl)-acetamide;
N-(3,4-Dihydro-2H-pyrano[2,3-b]pyridin-4-yl)-2-(4-fluoro-2-trifluoromethyl-phenyl)-acetamide;
2-(4-Chloro-2-trifluoromethyl-phenyl)-N-(3,4-dihydro-2H-pyrano[2,3-b]pyridin-4-yl)-acetamide;
2-(2,3-Dichloro-phenyl)-N-(3,4-dihydro-2H-pyrano[2,3-b]pyridin-4-yl)-acetamide;
2-(3,4-Dichloro-phenyl)-N-(3,4-dihydro-2H-pyrano[2,3-b]pyridin-4-yl)-acetamide;
2-(2,4-Dichloro-6-trifluoromethyl-phenyl)-N-(3,4-dihydro-2H-pyrano[2,3-b]pyridin-4-yl)-acetamide;
2-(2,4-Dichloro-5-fluoro-phenyl)-N-(3,4-dihydro-2H-pyrano[2,3-b]pyridin-4-yl)-acetamide;
1-(2,4-Dichloro-phenyl)-cyclopropanecarboxylic acid (3,4-dihydro-2H-pyrano[2,3-b]pyridin-4-yl)-amide;
1-(2-Chloro-4-fluoro-phenyl)-cyclopentanecarboxylic acid (3,4-dihydro-2H-pyrano[2,3-b]pyridin-4-yl)-amide;
2-(2-Chloro-pyridin-3-yl)-N-(3,4-dihydro-2H-pyrano[2,3-b]pyridin-4-yl)-acetamide;
N-(3,4-Dihydro-2H-pyrano[2,3-b]pyridin-4-yl)-2-(2,6-dimethyl-pyridin-3-yloxy)-acetamide;
N-(3,4-Dihydro-2H-pyrano[2,3-b]pyridin-4-yl)-2-(3-methyl-isoxazol-5-yl)-acetamide;
N-(3,4-Dihydro-2H-pyrano[2,3-b]pyridin-4-yl)-2-(5-methyl-pyrazol-1-yl)-acetamide;
2-(4-Chloro-phenyl)-N-(3,4-dihydro-2H-pyrano[2,3-b]pyridin-4-yl)-propionamide;
3-(2,4-Dichloro-phenyl)-N-(3,4-dihydro-2H-pyrano[2,3-b]pyridin-4-yl)-propionamide;
2-(2,3-Dichloro-phenyl)-N-(2,3-dihydro-furo[2,3-b]pyridin-3-yl)-acetamide;
2-(2,3-Dichloro-6-fluoro-phenyl)-N-(2,3-dihydro-furo[2,3-b]pyridin-3-yl)-acetamide;
N-(2,3-Dihydro-furo[2,3-b]pyridin-3-yl)-2-(2-fluoro-6-trifluoromethyl-phenyl)-acetamide;
N-(2,3-Dihydro-furo[2,3-b]pyridin-3-yl)-2-(3-fluoro-4-trifluoromethoxy-phenyl)-acetamide;
2-(2,4-Dichloro-6-fluoro-phenyl)-N-(3,4-dihydro-2H-pyrano[2,3-b]pyridin-4-yl)-acetamide;
2-(2,3-Dichloro-6-trifluoromethyl-phenyl)-N-(2,3-dihydrofuro[2,3-b]pyridin-3-yl)-acetamide;
2-(2,6-Dichloro-3-trifluoromethyl-phenyl)-N-(2,3-dihydrofuro[2,3-b]pyridin-3-yl)-acetamide;
2-(2-Chloro-3-trifluoromethyl-phenyl)-N—(S)-(2,3-dihydro-furo[2,3-b]pyridin-3-yl)-acetamide;
2-(2-Chloro-3-trifluoromethyl-phenyl)-N—(R)-(2,3-dihydro-furo[2,3-b]pyridin-3-yl)-acetamide; and
2-(2-Chloro-3-cyano-phenyl)-N-(2,3-dihydro-furo[2,3-b]pyridin-3-yl)-acetamide;
or salts (in particular pharmaceutically acceptable salts) of such compounds;

it is to be understood for any of the above listed compounds, that a stereogenic center, which is not specifically assigned, may be in absolute (R)- or absolute (S)-configuration; for example, the stereogenic center at the 3-position of the 2,3-dihydro-furo[2,3-b]pyridine core structure or at the 4-position of the 3,4-dihydro-2H-pyrano[2,3-b]pyridine core structure may be in absolute (R)-configuration or absolute (S)-configuration. Notably, compounds containing more than one stereogenic center may be at each stereogenic center, which is not specifically assigned, in absolute (R)- or absolute (S)-configuration;

for example a compound listed as 2-(4-Chloro-phenyl)-N-(2,3-dihydro-furo[2,3-b]pyridin-3-yl)-propionamide may be (S)-2-(4-Chloro-phenyl)-N—((S)-2,3-dihydro-furo[2,3-b]pyridin-3-yl)-propionamide, (S)-2-(4-Chloro-phenyl)-N—

((R)-2,3-dihydro-furo[2,3-b]pyridin-3-yl)-propionamide, (R)-2-(4-Chloro-phenyl)-N—((S)-2,3-dihydro-furo[2,3-b]pyridin-3-yl)-propionamide, (R)-2-(4-Chloro-phenyl)-N—((R)-2,3-dihydro-furo[2,3-b]pyridin-3-yl)-propionamide or any mixture thereof.

53) Further preferred compounds of formula (I) as defined in embodiment 1) are selected from the group consisting of:
2-(2,4-Dichloro-6-fluoro-phenyl)-N-(2,3-dihydro-furo[2,3-b]pyridin-3-yl)-acetamide;
2-(3,6-Dichloro-2-fluoro-phenyl)-N-(2,3-dihydro-furo[2,3-b]pyridin-3-yl)-acetamide;
2-(2-Chloro-3,6-difluoro-phenyl)-N-(2,3-dihydro-furo[2,3-b]pyridin-3-yl)-acetamide;
2-(2,4-Dichloro-phenyl)-N-2,3-dihydro-furo[2,3-b]pyridin-3-yl-3-hydroxy-propionamide;
2-Chloro-3-[(2,3-dihydro-furo[2,3-b]pyridin-3-ylcarbamoyl)-methyl]-benzamide;
2-(2,4-Dichloro-phenyl)-N-2,3-dihydro-furo[2,3-b]pyridin-3-yl-3-pyrrolidin-1-yl-propionamide;
N-(2,3-Dihydro-furo[2,3-b]pyridin-3-yl)-4-(4-fluoro-phenyl)-butyramide;
2-(2,4-Dichloro-phenyl)-N-(2,3-dihydro-furo[2,3-c]pyridin-3-yl)-acetamide;
2-(2,4-Dichloro-phenyl)-N-2,3-dihydro-furo[2,3-b]pyridin-3-yl-butyramide;
2-(2,4-Dichloro-phenyl)-N-2,3-dihydro-furo[2,3-b]pyridin-3-yl-propionamide;
2-(2,4-Dichloro-phenyl)-2-trideuteromethyl-N-2,3-dihydro-furo[2,3-b]pyridin-3-yl-acetamide;
2-(2-Chloro-3-trifluoromethyl-phenyl)-N-(2,3-dihydro-furo[2,3-c]pyridin-3-yl)-acetamide;
2-(2-Chloro-4-trifluoromethyl-phenyl)-N-(2,3-dihydro-furo[2,3-b]pyridin-3-yl)-acetamide;
2-(2,4-Dichloro-6-methyl-phenyl)-N-(2,3-dihydro-furo[2,3-c]pyridin-3-yl)-acetamide;
N-(2,3-Dihydro-furo[2,3-b]pyridin-3-yl)-2-(2-fluoro-3-trifluoromethyl-phenyl)-acetamide;
2-(2-Chloro-3-trifluoromethyl-phenyl)-N-2,3-dihydro-furo[2,3-b]pyridin-3-yl-propionamide;
(S)-2-(2,4-Dichloro-phenyl)-N—((S)-2,3-dihydro-furo[2,3-b]pyridin-3-yl)-propionamide;
(S)-2-(2,4-Dichloro-phenyl)-N—((R)-2,3-dihydro-furo[2,3-b]pyridin-3-yl)-propionamide;
(R)-2-(2,4-Dichloro-phenyl)-N—((S)-2,3-dihydro-furo[2,3-b]pyridin-3-yl)-propionamide;
(R)-2-(2,4-Dichloro-phenyl)-N—((R)-2,3-dihydro-furo[2,3-b]pyridin-3-yl)-propionamide;
2-(2-Chloro-4-cyano-phenyl)-N-(2,3-dihydro-furo[2,3-b]pyridin-3-yl)-acetamide;
2-(3-Chloro-2-trifluoromethyl-phenyl)-N-(2,3-dihydro-furo[2,3-b]pyridin-3-yl)-acetamide;
2-(2-Chloro-3-cyano-phenyl)-N—((R)-2,3-dihydro-furo[2,3-b]pyridin-3-yl)-acetamide;
2-(2-Chloro-3-cyano-phenyl)-N—((S)-2,3-dihydro-furo[2,3-b]pyridin-3-yl)-acetamide;
2-(2,4-Dichloro-phenyl)-N-(7-methyl-2,3-dihydro-furo[2,3-c]pyridin-3-yl)-acetamide;
2-(2,4-Dichloro-6-methyl-phenyl)-N—((R)-2,3-dihydro-furo[2,3-c]pyridin-3-yl)-acetamide;
2-(2,4-Dichloro-6-methyl-phenyl)-N—((S)-2,3-dihydro-furo[2,3-c]pyridin-3-yl)-acetamide;
2-(2,4-Dichloro-6-hydroxymethyl-phenyl)-N-(2,3-dihydro-furo[2,3-b]pyridin-3-yl)-acetamide;
N-(7-Cyclopropyl-2,3-dihydro-furo[2,3-c]pyridin-3-yl)-2-(2,4-dichloro-phenyl)-acetamide;
2-(2,4-Dichloro-phenyl)-N-(7-methoxy-2,3-dihydro-furo[2,3-c]pyridin-3-yl)-acetamide;
N-(7-Chloro-2,3-dihydro-furo[2,3-c]pyridin-3-yl)-2-(2,4-dichloro-phenyl)-acetamide;
2-(2-Chloro-3-cyano-4-fluoro-phenyl)-N-(2,3-dihydro-furo[2,3-b]pyridin-3-yl)-acetamide;
2-(2-Chloro-3-trifluoromethoxy-phenyl)-N-(2,3-dihydro-furo[2,3-b]pyridin-3-yl)-acetamide;
2-(2-Chloro-3-trifluoromethyl-phenyl)-N-(5,6-dihydro-furo[2,3-c]pyridazin-5-yl)-acetamide;
2-(2,4-Dichloro-6-methyl-phenyl)-N-(5,6-dihydro-furo[2,3-c]pyridazin-5-yl)-acetamide;
2-(3-Acetyl-2-chloro-phenyl)-N-(2,3-dihydro-furo[2,3-b]pyridin-3-yl)-acetamide;
2-(2,4-Dichloro-3-cyano-phenyl)-N-(2,3-dihydro-furo[2,3-b]pyridin-3-yl)-acetamide;
2-(3-Cyano-2-trifluoromethyl-phenyl)-N-(2,3-dihydro-furo[2,3-b]pyridin-3-yl)-acetamide;
2-(2-Chloro-3-difluoromethyl-phenyl)-N-(2,3-dihydro-furo[2,3-b]pyridin-3-yl)-acetamide;
N-(5-Chloro-2,3-dihydro-furo[2,3-c]pyridin-3-yl)-2-(2-chloro-3-trifluoromethyl-phenyl)-acetamide;
N-(5-Chloro-2,3-dihydro-furo[2,3-c]pyridin-3-yl)-2-(2,4-dichloro-phenyl)-acetamide;
2-(2-Chloro-3-trifluoromethyl-phenyl)-N-(5-methyl-2,3-dihydro-furo[2,3-c]pyridin-3-yl)-acetamide;
(S)-2-(2-Chloro-3-trifluoromethyl-phenyl)-N—((S)-2,3-dihydro-furo[2,3-b]pyridin-3-yl)-propionamide;
(S)-2-(2-Chloro-3-trifluoromethyl-phenyl)-2-trideuteromethyl-N—((S)-2,3-dihydro-furo[2,3-b]pyridin-3-yl)-acetamide;
(S)-2-(2-Chloro-3-trifluoromethyl-phenyl)-N—((R)-2,3-dihydro-furo[2,3-b]pyridin-3-yl)-propionamide;
(S)-2-(2-Chloro-3-trifluoromethyl-phenyl)-2-trideuteromethyl-N—((R)-2,3-dihydro-furo[2,3-b]pyridin-3-yl)-acetamide;
(R)-2-(2-Chloro-3-trifluoromethyl-phenyl)-N—((S)-2,3-dihydro-furo[2,3-b]pyridin-3-yl)-propionamide;
(R)-2-(2-Chloro-3-trifluoromethyl-phenyl)-2-trideuteromethyl-N—((S)-2,3-dihydro-furo[2,3-b]pyridin-3-yl)-acetamide;
(R)-2-(2-Chloro-3-trifluoromethyl-phenyl)-N—((R)-2,3-dihydro-furo[2,3-b]pyridin-3-yl)-propionamide;
(R)-2-(2-Chloro-3-trifluoromethyl-phenyl)-2-trideuteromethyl-N—((R)-2,3-dihydro-furo[2,3-b]pyridin-3-yl)-acetamide;
2-(2-Chloro-3-trifluoromethyl-phenyl)-2-trideuteromethyl-N—((R)-2,3-dihydro-furo[2,3-b]pyridin-3-yl)-acetamide;
2-(2-Chloro-3-trifluoromethyl-phenyl)-2-trideuteromethyl-N—((S)-2,3-dihydro-furo[2,3-b]pyridin-3-yl)-acetamide;
2-(2-Chloro-3-trifluoromethyl-phenyl)-N-(4-methyl-2,3-dihydro-furo[2,3-c]pyridin-3-yl)-acetamide;
2-(2-Chloro-3-trifluoromethyl-phenyl)-N-(7-oxy-2,3-dihydro-furo[2,3-b]pyridin-3-yl)-acetamide;
5,7-dichloro-N-(2,3-dihydrofuro[2,3-b]pyridin-3-yl)-2,3-dihydro-1H-indene-1-carboxamide;
2-(2,4-Dichloro-6-methyl-phenyl)-N-(4-methyl-2,3-dihydro-furo[2,3-c]pyridin-3-yl)-acetamide;
2-(2-Chloro-3-trifluoromethyl-phenyl)-N-(4-cyclopropyl-2,3-dihydro-furo[2,3-c]pyridin-3-yl)-acetamide;
2-(2,4-Dichloro-6-methyl-phenyl)-N-(6-methyl-2,3-dihydro-furo[2,3-b]pyridin-3-yl)-acetamide;
2-(2-Chloro-3-trifluoromethyl-phenyl)-N-(6-methyl-2,3-dihydro-furo[2,3-b]pyridin-3-yl)-acetamide;
2-(2-Chloro-3-trifluoromethyl-phenyl)-N-(4-methoxy-6-methyl-2,3-dihydro-furo[2,3-b]pyridin-3-yl)-acetamide;
2-(2-Chloro-3-trifluoromethyl-phenyl)-N-(4-ethoxy-6-methyl-2,3-dihydro-furo[2,3-b]pyridin-3-yl)-acetamide;

2-(2-Chloro-3-trifluoromethyl-phenyl)-N-(4-methyl-2,3-dihydro-furo[2,3-b]pyridin-3-yl)-acetamide;
2-(2,4-Dichloro-6-methyl-phenyl)-N-(4-methyl-2,3-dihydro-furo[2,3-b]pyridin-3-yl)-acetamide;
2-(2-Chloro-3-trifluoromethyl-phenyl)-N-(4-methoxy-2,3-dihydro-furo[2,3-b]pyridin-3-yl)-acetamide;
2-(2,4-Dichloro-phenoxy)-N-(2,3-di hydro-furo[2,3-b]pyridin-3-yl)-acetamide;
2-(3,4-Dichloro-phenoxy)-N-(2,3-di hydro-furo[2,3-b]pyridin-3-yl)-acetamide;
N-(2,3-Dihydro-furo[2,3-b]pyridin-3-yl)-2-(2,4-dimethyl-phenoxy)-acetamide;
N-(6-Chloro-2,3-dihydro-furo[2,3-b]pyridin-3-yl)-2-(2-chloro-3-trifluoromethyl-phenyl)-acetamide;
N-(6-Chloro-2,3-dihydro-furo[2,3-b]pyridin-3-yl)-2-(2,4-dichloro-6-methyl-phenyl)-acetamide;
5-chloro-N-(2,3-dihydrofuro[2,3-b]pyridin-3-yl)-2,3-dihydro-1H-indene-1-carboxamide;
2-(2-Chloro-3-trifluoromethyl-phenyl)-N-(6-oxy-2,3-dihydro-furo[2,3-c]pyridin-3-yl)-acetamide;
5-chloro-N—((R)-2,3-dihydrofuro[2,3-b]pyridin-3-yl)-2,3-dihydro-1H-indene-2-carboxamide;
5-chloro-N—((S)-2,3-dihydrofuro[2,3-b]pyridin-3-yl)-2,3-dihydro-1H-indene-2-carboxamide;
2-(2,4-Dichloro-6-methyl-phenyl)-N-(4-trifluoromethyl-2,3-dihydro-furo[2,3-b]pyridin-3-yl)-acetamide; and
2-(2-Chloro-3-trifluoromethyl-phenyl)-N-(4-trifluoromethyl-2,3-dihydro-furo[2,3-b]pyridin-3-yl)-acetamide;
or salts (in particular pharmaceutically acceptable salts) of such compounds;
it is to be understood for any of the above listed compounds, that a stereogenic center, which is not specifically assigned, may be in absolute (R)- or absolute (S)-configuration;
for example, the stereogenic center at the 3-position of the 2,3-dihydro-furo[2,3-b]pyridine or of the 2,3-dihydro-furo[2,3-c]pyridine core structure or of the 5-position of the 5,6-dihydro-furo[2,3-c]pyridazine core structure may be in absolute (R)-configuration or absolute (S)-configuration. Notably, compounds containing more than one stereogenic center may be at each stereogenic center, which is not specifically assigned, in absolute (R)- or absolute (S)-configuration; for example a compound listed as 2-(2,4-Dichloro-phenyl)-N-2,3-dihydro-furo[2,3-b]pyridin-3-yl-3-hydroxy-propionamide may be (S)-2-(2,4-Dichloro-phenyl)-N—((S)-2,3-dihydro-furo[2,3-b]pyridin-3-yl)-3-hydroxy-propionamide, (S)-2-(2,4-Dichloro-phenyl)-N—((R)-2,3-dihydro-furo[2,3-b]pyridin-3-yl)-3-hydroxy-propionamide, (R)-2-(2,4-Dichloro-phenyl)-N—((S)-2,3-dihydro-furo[2,3-b]pyridin-3-yl)-3-hydroxy-propionamide, (R)-2-(2,4-Dichloro-phenyl)-N—((R)-2,3-dihydro-furo[2,3-b]pyridin-3-yl)-3-hydroxy-propionamide or any mixture thereof.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

Where the plural form is used for compounds, salts, pharmaceutical compositions, diseases and the like, this is intended to mean also a single compound, salt, or the like.

The compounds of formula (I) according to any one of embodiments 1) to 53), or pharmaceutically acceptable salts thereof, are suitable for use as medicaments. In particular, compounds of formula (I) modulate the P2X$_7$ receptor, i.e. they act as P2X$_7$ receptor antagonists, and are useful for the prevention or treatment of diseases which are associated with the activation of the P2X$_7$ receptor such as pain; neurodegenerative and neuroinflammatory diseases; bone and joint diseases; obstructive diseases of the airways; cardiovascular diseases; eye diseases; skin diseases; abdominal and gastrointestinal tract diseases; genitourinary diseases; cancer; other auto-immune and allergic disorders; and other disorders with an inflammatory or immunological component.

In particular, the compounds of formula (I) according to any one of embodiments 1) to 53), or pharmaceutically acceptable salts thereof, are suitable for the prevention or treatment of pain. Pain refers to acute pain; chronic pain; pain associated with sprains and strains; chronic articular pain; pain associated with rheumatic fever; musculoskeletal pain; lower back and neck pain; inflammatory pain; neuropathic pain; visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain.

Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Chronic articular pain conditions include especially rheumatoid arthritis, osteoarthritis, rheumatoid spondylitis, gouty arthritis and juvenile arthritis.

Pain associated with functional bowel disorders includes especially non-ulcer dyspepsia, non-cardiac chest pain and irritable bowel syndrome.

Further, the compounds of formula (I) according to any one of embodiments 1) to 53), or pharmaceutically acceptable salts thereof, are suitable for the prevention or treatment of neurodegenerative and neuroinflammatory diseases. Neurodegenerative and neuro-inflammatory diseases include Alzheimer's disease and other dementing disorders including, but not limited to, Creutzfeldt-Jakob disease (CJD) and new variant Creutzfeldt-Jakob disease (nvCJD); Amyotrophic lateral sclerosis, amyloidosis; multiple sclerosis and other demyelinating syndromes; cerebral atherosclerosis and vasculitis; temporal arteritis; myasthenia gravis; Huntington's disease; Lewy Body dementia; and Parkinson's disease.

Further, the compounds of formula (I) according to any one of embodiments 1) to 53), or pharmaceutically acceptable salts thereof, are suitable for the prevention or treatment of bone and joint diseases. Bone and joint diseases include arthritides such as rheumatoid arthritis, osteoarthritis, gout or crystal arthropathy; intervertebral disc degeneration; temporomandibular joint degeneration; bone remodelling disease such as osteoporosis, Paget's disease or osteonecrosis; polychondritis; scleroderma; mixed connective tissue disorder; spondyloarthropathies; periodontal disease such as periodontitis; arthritides associated with or including osteoarthritis/osteoarthrosis, both primary and secondary to, for example, congenital hip dysplasia; cervical and lumbar spondylitis; Still's disease; seronegative spondyloarthropathies including ankylosing spondylitis, psoriatic arthritis, reactive arthritis and undifferentiated spondyloarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; Familial Mediterranean fever, Muckle-Wells syndrome, and Familial Hibernian Fever, Kikuchi disease; and drug-induced arthalgias, tendonitis, and myopathies including dystrophies and other inflammatory myopathies.

Further, the compounds of formula (I) according to any one of embodiments 1) to 53), or pharmaceutically acceptable salts thereof, are suitable for the prevention or treatment of obstructive diseases of the airways. Obstructive diseases of the airways include asthma, including bronchial, allergic, intrinsic, and extrinsic asthma, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; and acute viral infection including the common cold, and infection due to respiratory syncytial virus, influenza, coronavirus (including SARS) and adenovirus.

Further, the compounds of formula (I) according to any one of embodiments 1) to 53), or pharmaceutically acceptable salts thereof, are suitable for the prevention or treatment of cardiovascular diseases. Cardiovascular diseases include atherosclerosis, affecting the coronary and peripheral circulation; pericarditis; myocarditis; inflammatory and auto-immune cardiomyopathies including myocardial sarcoid; ischaemic reperfusion injuries; endocarditis, valvulitis, and aortitis including infective (for example syphilitic); vasculitides; and disorders of the proximal and peripheral veins including phlebitis and thrombosis, including deep vein thrombosis and complications of varicose veins.

Further, the compounds of formula (I) according to any one of embodiments 1) to 53), or pharmaceutically acceptable salts thereof, are suitable for the prevention or treatment of eye diseases. Eye diseases include blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; and infections of the eyes including viral, fungal, and bacterial infections.

Further, the compounds of formula (I) according to any one of embodiments 1) to 53), or pharmaceutically acceptable salts thereof, are suitable for the prevention or treatment of skin diseases. Skin diseases include psoriasis, skin burn, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; and drug-induced disorders including fixed drug eruptions.

Further, the compounds of formula (I) according to any one of embodiments 1) to 53), or pharmaceutically acceptable salts thereof, are suitable for the prevention or treatment of abdominal and gastrointestinal tract diseases. Abdominal and gastrointestinal tract diseases include hepatitis, including autoimmune, alcoholic and viral hepatitis; fibrosis and cirrhosis of the liver; cholecystitis; pancreatitis, both acute and chronic; non-inflammatory diarrhea; glossitis, gingivitis, periodontitis; oesophagitis, including reflux; eosinophilic gastro-enteritis, mastocytosis, Crohn's disease, colitis including ulcerative colitis, proctitis, pruritis ani; Coeliac disease, irritable bowel disease/syndrome, and food-related allergies which may have effects remote from the gut, for example migraine, rhinitis or eczema; allograft rejection including acute and chronic allograft rejection following, for example, transplantation of kidney, heart, liver, lung, bone marrow, skin or cornea or following blood transfusion; and chronic graft versus host disease;

Further, the compounds of formula (I) according to any one of embodiments 1) to 53), or pharmaceutically acceptable salts thereof, are suitable for the prevention or treatment of genitourinary diseases. Genitourinary diseases include nephritis including interstitial and Jo glomerulonephritis; nephrotic syndrome; cystitis including acute and chronic (interstitial) cystitis and Hunner's ulcer; acute and chronic urethritis, hemorrhagic cystitis, prostatitis, epididymitis, oophoritis and salpingitis; vulvovaginitis; Peyronie's disease; and erectile dysfunction, both male and female.

Further, the compounds of formula (I) according to any one of embodiments 1) to 53), or pharmaceutically acceptable salts thereof, are suitable for the prevention or treatment of cancer. The treatment of cancer includes the treatment of brain tumors, prostate, lung, breast, ovarian, bowel and colon, stomach, pancreatic, skin and bone marrow (including leukaemias) and lymphoproliferative systems, such as non-Hodgkin's and Hodgkin's lymphoma; including the prevention and treatment of metastatic disease and tumor recurrences, and paraneoplastic syndromes.

Further, the compounds of formula (I) according to any one of embodiments 1) to 53), or pharmaceutically acceptable salts thereof, are suitable for the prevention or treatment of other auto-immune and allergic disorders. Other auto-immune and allergic disorders include Hashimoto's thyroiditis, Graves' disease, Addison's disease, diabetes mellitus, idiopathic thrombocytopaenic purpura, eosinophilic fasciitis, hyper-IgE syndrome, and antiphospholipid syndrome.

Further, the compounds of formula (I) according to any one of embodiments 1) to 53), or pharmaceutically acceptable salts thereof, are suitable for the prevention or treatment of other disorders with an inflammatory or immunological component. Other disorders with an inflammatory or immunological component include acquired immune deficiency syndrome (AIDS), leprosy, Sezary syndrome, and paraneoplastic syndromes.

Further, the compounds of formula (I) according to any one of embodiments 1) to 53), or pharmaceutically acceptable salts thereof, are suitable for the prevention or treatment of mood, depression, sleep and anxiety disorders.

Further, the compounds of formula (I) according to any one of embodiments 1) to 53), or pharmaceutically acceptable salts thereof, are suitable for the prevention or treatment of injury induced trauma and spinal cord injury.

Especially, compounds of formula (I) according to any one of embodiments 1) to 53), or pharmaceutically acceptable salts thereof, are suitable for the prevention or treatment of diseases selected from one, several or all of the following groups of diseases and disorders:

1) Pain, wherein pain refers to acute pain; chronic pain; pain associated with sprains and strains; chronic articular pain; pain associated with rheumatic fever; musculoskeletal pain; lower back and neck pain; inflammatory pain; neuropathic pain; visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain;

Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia);

Chronic articular pain conditions include especially rheumatoid arthritis, osteoarthritis, rheumatoid spondylitis, gouty arthritis and juvenile arthritis; Pain associated with functional bowel disorders includes especially non-ulcer dyspepsia, non-cardiac chest pain and irritable bowel syndrome;

2) Neurodegenerative and neuro-inflammatory diseases such as Alzheimer's disease and other dementing disorders including, but not limited to, Creutzfeldt-Jakob disease (CJD) and new variant Creutzfeldt-Jakob disease (nvCJD); amyloidosis; Amyotrophic lateral sclerosis, multiple sclerosis and other demyelinating syndromes; cerebral atherosclerosis and vasculitis; temporal arteritis; myasthenia gravis; Huntington's disease; Lewy Body dementia; and Parkinson's disease;

3) Bone and joint diseases such as arthritides such as rheumatoid arthritis, osteoarthritis, gout or crystal arthropathy; intervertebral disc degeneration; temporomandibular joint degeneration; bone remodelling disease such as osteoporosis, Paget's disease or osteonecrosis; polychondritis; scleroderma; mixed connective tissue disorder; spondyloarthropathies; periodontal disease such as periodontitis; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; Muckle-Wells syndrome, and Familial Hibernian Fever, Kikuchi disease; and drug-induced arthalgias, tendonitis, and myopathies;

4) Obstructive diseases of the airways such as chronic obstructive pulmonary disease (COPD); cystic fibrosis; lung emphysema; sarcoidosis; farmer's lung and related diseases; lung fibrosis, including fibrosis complicating tuberculosis; and chronic cough associated with inflammatory and secretory conditions of the airways;

5) Cardiovascular diseases such as inflammatory and auto-immune cardiomyopathies;

6) Eye diseases such as degenerative or inflammatory disorders affecting the retina;

7) Skin diseases such as psoriasis, skin burn, atopic dermatitis, contact dermatitis or other eczematous dermatoses; and discoid lupus erythematosus;

8) Abdominal and gastrointestinal tract diseases such as fibrosis and cirrhosis of the liver; cholecystitis; pancreatitis, both acute and chronic; Crohn's disease; colitis including ulcerative colitis; and irritable bowel disease/syndrome;

9) Genitourinary diseases such as nephritis including interstitial and glomerulonephritis; nephrotic syndrome; and cystitis including acute and chronic (interstitial) cystitis; and
10) Other auto-immune and allergic disorders such as Hashimoto's thyroiditis, Graves' disease, Addison's disease, diabetes mellitus, idiopathic thrombocytopaenic purpura, eosinophilic fasciitis, hyper-IgE syndrome, and antiphospholipid syndrome.

Most preferably, compounds of formula (I) according to any one of embodiments 1) to 53), or pharmaceutically acceptable salts thereof, are suitable for the prevention or treatment of diseases selected from one, several or all of the following groups of diseases and disorders:
1) Pain, wherein pain refers to acute pain; chronic pain; pain associated with sprains and strains; chronic articular pain; pain associated with rheumatic fever; musculoskeletal pain (preferred); lower back and neck pain; inflammatory pain; neuropathic pain (preferred); visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain;
Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia);
Chronic articular pain conditions include especially rheumatoid arthritis, osteoarthritis, rheumatoid spondylitis, gouty arthritis and juvenile arthritis; Pain associated with functional bowel disorders includes especially non-ulcer dyspepsia, non-cardiac chest pain and irritable bowel syndrome;
2) Rheumatoid arthritis and osteoarthritis;
3) Chronic obstructive pulmonary disease (COPD); and
4) Crohn's disease.

The invention also relates to the use of a compound of formula (I) according to any one of embodiments 1) to 53) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 53).

A pharmaceutical composition according to the present invention contains at least one compound of formula (I) according to any one of embodiments 1) to 53) (or a pharmaceutically acceptable salt thereof) as the active agent and optionally carriers and/or diluents and/or adjuvants.

The compounds of formula (I) according to any one of embodiments 1) to 53) and their pharmaceutically acceptable salts can be used as medicaments, e.g. in the form of pharmaceutical compositions for enteral (such as especially oral) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 53), or a pharmaceutically acceptable salt thereof.

Any reference to a compound of formula (I), $(I_P)$, $(I_{St1})$, $(I_{St2})$, $(I_{St1-P})$ or $(I_{St2-P})$ in this text is to be understood as referring also to the salts (and especially the pharmaceutically acceptable salts) of such compounds, as appropriate and expedient. The preferences indicated for the compounds of formula (I) of course apply mutatis mutandis to the compounds of formula $(I_P)$, of formula $(I_{St1})$, of formula $(I_{St2})$, of formula $(I_{St1-P})$ and of formula $(I_{St2-P})$ as well as to the salts and pharmaceutically acceptable salts of the compounds of formula (I), of formula $(I_P)$, of formula $(I_{St1})$, of formula $(I_{St2})$, of formula $(I_{St1-P})$ and of formula $(I_{St2-P})$. The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (RT) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

If not indicated otherwise, the generic groups $R^1$, $R^2$, $R^3$, $R^4$, $R^5$, $R^6$, X, Y and n are as defined for formula (I). Other abbreviations used are defined in the experimental section.

In some instances the generic groups $R^1$, $R^2$, $R^3$, $R^4$, $R^5$, $R^6$, X, Y and n might be incompatible with the assembly illustrated in the schemes below and will therefore require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups are as necessary in place.

Preparation of Compounds of Formula (I):

Compounds of formula (Ia) can be prepared by reaction of an amine (II) with an acid (III) using standard amide coupling reagents such as HOBt/EDC.HCl, TBTU or HOAt and a base like DIPEA in a solvent like DCM, THF or DMF preferably at temperatures between RT and 45° C. (scheme 1).

Scheme 1: Synthesis of compounds of formula (Ia)

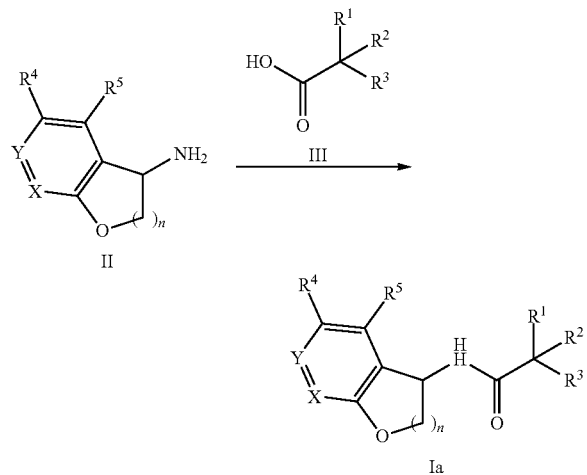

Compounds of formula (Ib) and (Ic), wherein X or Y represents N(O) and the other one represents $C(R^6)$ can be prepared from compounds of formula (Ia), wherein X or Y represent N and the other one represents $C(R^6)$ by oxidation with a suitable oxidating reagent such as 3-chloroperbenzoic acid in a solvent such as DCM or THF at temperatures between 0° C. and 45° C. (scheme 2).

Scheme 2: Synthesis of compounds of formula (Ib) and (Ic)

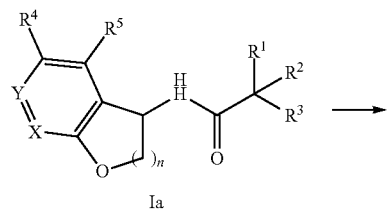

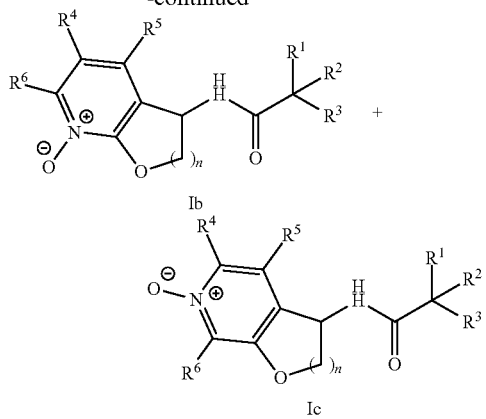

Compounds of formula (II), if not commercially available, can be prepared following the procedures outlined in the Schemes below.

Compounds of formula (IIa), wherein n represents 1, can be prepared starting from carboxylic ester derivatives (IV), wherein Z is bromide or chloride, by an alkylation/condensation reaction sequence with ethyl glycolate in a solvent like dimethoxyethane or DMF in the presence of a suitable base such as NaH preferably at temperatures between 45° C. and 80° C. The respective β-hydroxy esters (V) can be decarboxylated to form ketones (VI) by heating in a suitable solvent like water or THF in the presence of an acid such as HCl. Ketoximes (VII) can be prepared via condensation using standard conditions such as O-methylhydroxylamine in a suitable solvent like MeOH or EtOH optionally in the presence of a base such as NaOAc preferably at temperatures between RT and 60° C. The reduction to form amines of formula (IIa) can be carried out for instance via catalytic hydrogenation in the presence of a suitable catalyst such as Pd/C or Raney Nickel in a solvent like EtOH or a $NH_3$/MeOH solution. Alternatively, the reduction can be done in the presence of a reducing agent such as $BH_3$ in a solvent like THF at temperatures between RT and 60° C. (scheme 3).

Alternatively, compounds of formula (IIa), wherein $R^4$ and/or $R^5$ represent ($C_1$-$C_3$)alkyl or ($C_3$-$C_6$)cycloalkyl, can be synthesized in two steps from ketoximes (VII), wherein $R^4$ and/or $R^5$ represent halogen, via (1) a Suzuki type coupling reaction with the respective boronic acid derivatives such as ethylboronic acid or cyclopropylboronic acid in the presence of a suitable base such as $K_2CO_3$ and a palladium catalyst like tetrakis(triphenylphosphine)palladium in a solvent such as EtOH or dioxane preferably at temperatures between RT and 100° C. and (2) reduction of the obtained ketoxime moiety (VIIa) under the conditions mentioned above (scheme 3).

Alternatively, compounds of formula (IIa), wherein $R^4$ and/or $R^5$ represent ($C_1$-$C_3$)alkoxy, can be synthesized in two steps from ketoximes (VII), wherein $R^4$ and/or $R^5$ represent halogen, via (1) aromatic nucleophilic substitution using for instance NaOMe or NaOEt and heating in a suitable solvent such MeOH or EtOH at temperatures between 40° C. and 90° C. and (2) reduction of the obtained ketoxime moiety (VIIa) under the conditions mentioned above (scheme 3).

Compounds of formula (IV), if not commercially available, can be prepared according to procedures known to the one skilled in the art. For instance, when $R^4$, $R^5$ and/or $R^6$ represent ($C_1$-$C_3$)alkyl or ($C_3$-$C_6$)cycloalkyl, such compounds can be prepared via a Suzuki type coupling of an appropriate halide of formula (VIII), wherein Z is preferably chloride and $R^a$ represents halogen, preferably bromide. In case $R^4$, $R^5$ and/or $R^6$ represent $(C_1-C_3)$alkoxy, compounds of formula (IV) can be obtained from compounds of formula (VIII), wherein Z is preferably chloride and $R^a$ represents halogen, preferably bromide or chloride, via aromatic nucleophilic substitution under the conditions mentioned above.

Compounds of formula (IV), wherein $R^4$, $R^5$ and/or $R^6$ represent $(C_1-C_3)$fluoroalkyl are commercially available or can be prepared from an appropriate halide of formula (VIII), wherein Z is preferably chloride and $R^a$ represents halogen, preferably iodide or bromide via aromatic trifluoromethylation using trifluoromethyltrimethylsilane or 2,2-difluoro-2-fluorosulfonylacetic acid methyl ester in the presence of a suitable catalyst system like CuI/KF in a solvent such as NMP or DMF preferably at temperatures between RT and 90° C.

between 0° C. and 45° C. The reduction of ketoximes (VIIc) to the corresponding amines (IIb) can be carried out with a reducing agent such as $BH_3$ in a solvent like THF at temperatures between RT and 60° C. (scheme 4).

Compounds of formula (IIc), wherein Y represents N and X represents $C(R^6)$ wherein $R^6$ represents $(C_1-C_3)$alkoxy, can be prepared by aromatic nucleophilic substitution of a compound of formula (VIIc) with an alkoxide such as NaOMe or NaOEt and heating in a suitable solvent such MeOH or EtOH at temperatures between 40° C. and 90° C. The reduction of ketoximes (VIId), wherein $R^b$ represents $(C_1-C_3)$alkyl, to form the corresponding amines (IIc) can be carried out as previously described in scheme 3 for the synthesis of compounds of formula (IIa) (scheme 4).

Scheme 3: Synthesis of compounds of formula (IIa) wherein n represents 1

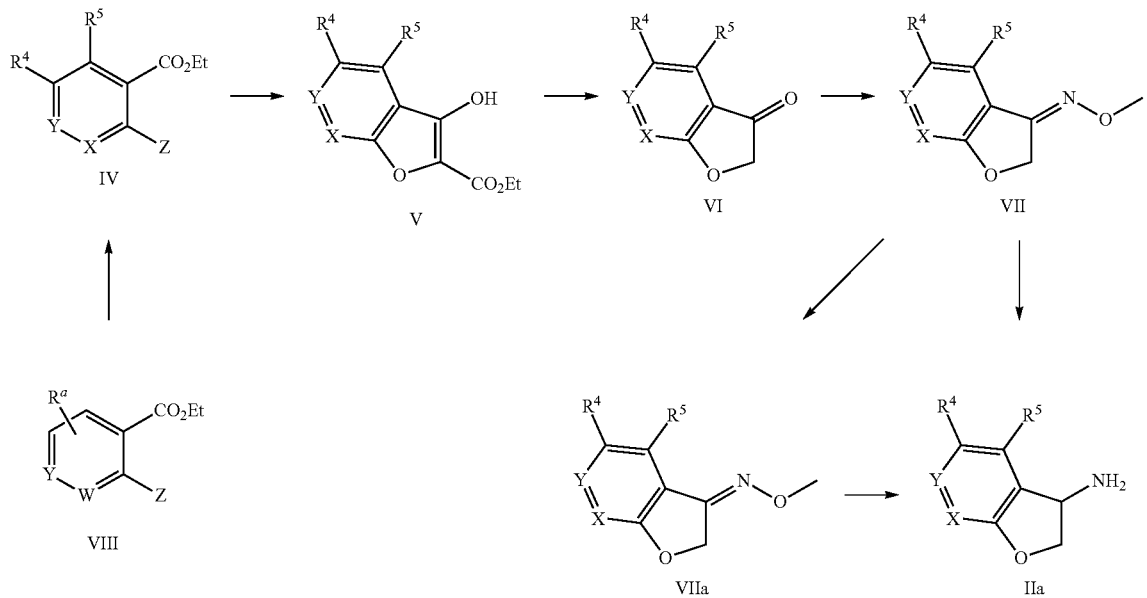

Compounds of formula (IIb), wherein Y represents N and X represents $C(R^6)$ wherein $R^6$ represents chloride, can be prepared in two steps from ketoximes (VIIb) via an oxidation/chlorination reaction sequence. The oxidation can be carried out with a suitable oxidating reagent such as 3-chloroperbenzoic acid in a solvent such as DCM or THF at temperatures between 0° C. and 45° C. The intermediate N-oxide can then be chlorinated using standard conditions such as phosphoryl chloride in a solvent such as DCM preferably at temperatures Compounds of formula (IId), wherein Y represents N and X represents $C(R^6)$ wherein $R^6$ represents $(C_1-C_3)$alkyl or $(C_3-C_6)$cycloalkyl, can be prepared via Suzuki type coupling of compounds of formula (VIIc) to form compounds of formula (VIIe), wherein $R^c$ represents $(C_1-C_3)$alkyl or $(C_3-C_6)$cycloalkyl under the conditions mentioned above. The final reduction to form amines (IId) can be carried out as previously described in scheme 3 for the synthesis of compounds of formula (IIa) (scheme 4).

Scheme 4: Synthesis of compounds of formula (IIb), (IIc) and (IId)

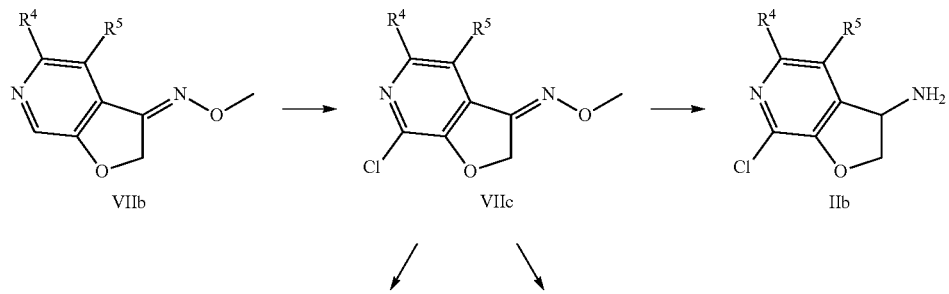

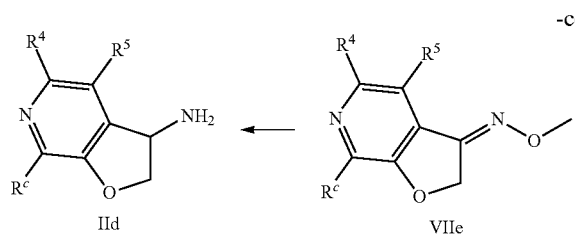

IId ← VIIe

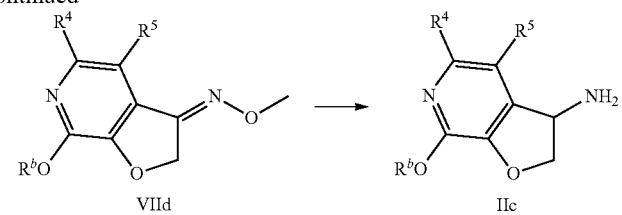

VIId → IIc

In analogy, compounds of formula (II), wherein X represents N and Y represents C(R⁶) with R⁶ representing (C₁-C₃) alkyl, (C₃-C₆)cycloalkyl, (C₁-C₃)alkoxy or halogen can be prepared starting from compounds of formula (VII), wherein X represents N and Y represents C(R⁶) with R⁶ representing hydrogen, using the same synthetic strategy as presented in scheme 4.

Compounds of formula (IIe), wherein n represents 2, can be prepared from aldehydes (IX), wherein Z is bromide or chloride, by an alkylation using EtOAc in the presence of a base such as LDA in a solvent like THF preferably at temperatures between −78° C. and RT to form β-hydroxy esters (X). Reduction of the ester moiety to form the corresponding diols (XI) can be carried out using a reducing agent like LiAlH₄, LiBH₄, diisobutylaluminum hydride or BH₃ in a solvent such as THF or Et₂O preferably at temperatures between −78° C. and 45° C. Diols (XI) can be transformed into hydroxy derivatives of formula (XII) by treatment with a base like tBuOK in a solvent such as tBuOH preferably at temperatures between RT and 80° C. Azides (XIII) can be prepared from compounds of formula (XII) via an azidation using conditions such as DPPA in the presence of DBU in a solvent like toluene or THF preferably at temperatures between 0° C. and RT. Reduction of azides (XIII) to form the corresponding amines (IIe) can be carried out for instance via catalytic hydrogenation in the presence of a suitable catalyst such as Pd/C in a solvent such as EtOH. Alternatively, the azide moiety can be transformed into the amine via a Staudinger type reaction using PPh₃ in a solvent such as THF/H₂O preferably at temperatures around RT (scheme 5).

Compounds of formula (IX), if not commercially available, can be prepared according to procedures known to the one skilled in the art. For instance, aldehydes (IX) wherein R⁴, R⁵ and/or R⁶ represent (C₁-C₃)alkyl, (C₃-C₆)cycloalkyl, (C₁-C₃)fluoroalkyl or (C₁-C₃)alkoxy can be prepared from carboxylic ester derivatives (IV) (described above in scheme 3) via (1) reduction using a suitable reducing reagent such as diisobutylaluminum hydride in a solvent such as THF or DCM at temperatures between −78° C. and RT. And if necessary followed by (2) oxidation of the respective alcohol using a suitable oxidating reagent such as dipyridinium dichromate or Dess Martin's reagent in a solvent such as DCM preferably at temperatures around RT. (scheme 6)

Alternatively, compounds of formula (IX) can be prepared using the conditions mentioned above for Suzuki type couplings, aromatic trifluoromethylation and aromatic nucleophilic substitutions from compounds of formula (XIV) wherein Rᵃ represents halogen, Z is preferably chloride and Rᶜ represents a protected aldehyde moiety bearing a suitable protecting group such as an acetal. (scheme 6)

Scheme 6: Synthesis of compounds of formula (IX)

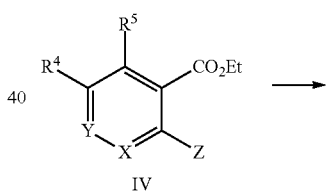

IV →

Scheme 5: Synthesis of compounds of formula (IIe), wherein n represents 2

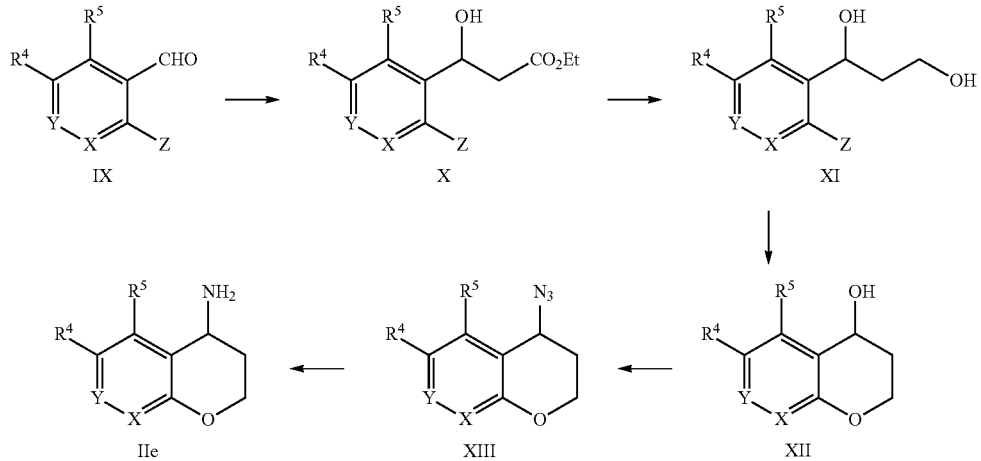

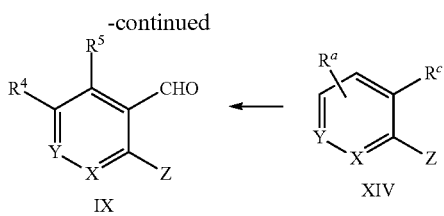

Compounds of formula (III), if not commercially available, can be prepared following the procedures outlined in Scheme 7 below or as described in the experimental part.

If not commercially available, anilines (XV), wherein $R^3$ represents aryl, can be prepared according to procedures known to the one skilled in the art.

Compounds of formula (XVI) wherein $R^3$ represents aryl and R represents methyl, ethyl or tert.-butyl can be prepared from aniline derivatives (XV) by a Meerwein arylation type reaction using a Cu(II) salt like $CuCl_2$, tBu-nitrite and 1,1-dichloroethylene in a solvent like $CH_3CN$ followed by refluxing in MeOH in the presence of sodium methoxide and subsequent treatment with concentrated $H_2SO_4$, preferably at temperatures between RT and 90° C.

Compounds of formula (XVI), wherein $R^3$ contains a nitrile substituent, can be prepared from compounds of formula (XVI), wherein $R^3$ contains an iodide or bromide substituent, by a palladium catalyzed cyanation reaction using $Zn(CN)_2$ in the presence of a suitable catalyst like tetrakis(triphenylphosphine)palladium in a solvent such as NMP preferably at temperatures between RT and 100° C.

Alternatively, compounds of formula (XVI), wherein $R^3$ contains a nitrile substituent, can be prepared from compounds of formula (XVI), wherein $R^3$ contains a carboxamide substituent, by a dehydration reaction using trifluoromethanesulfonic anhydride as dehydrating agent in the presence of $Et_3N$ in a solvent such as DCM preferably at temperatures between 0° C. and RT.

Alternatively, compounds of formula (XVI) can be prepared starting from the corresponding carboxylic acids of formula (XVII), like for instance benzoic acids or pyridinecarboxylic acids, via an Arndt-Eistert homologation. The respective α-diazoketones can be prepared using oxalylchloride in DCM followed by treatment with (trimethylsilyl)diazomethane in a solvent such as THF or diethylether preferably at temperatures between −5° C. and RT. A Wolff rearrangement using a silver(I)catalyst such as silver benzoate in the presence of an alcohol such as MeOH preferably at temperatures between 0° C. and RT leads to the desired ester derivatives (XVI) (scheme 7).

Alternatively, compounds of formula (XVI) can be prepared starting from the corresponding halides $R^3$—Z of formula (XVIII), wherein Z is chloride or iodide and $R^3$ represents aryl or heteroaryl, via a palladium catalyzed Negishi type coupling using a zinc reagent such as (2-tert.-butoxy-2-oxoethyl)zinc chloride in the presence of a suitable catalyst like tetrakis(triphenylphosphine)palladium in a solvent such as THF or dioxane preferably at temperatures between RT and 100° C.

Alternatively, halides $R^3$—Z of formula (XVIII), wherein the halide Z can be preferably bromide or fluoride and $R^3$ represents heteroaryl, can be transformed into compounds of formula (XVI) via a malonate addition/decarboxylation sequence. The malonate addition can be done using a malonate such as methyl malonate in the presence of a suitable base such as NaH in a solvent such as DMF or NMP preferably at temperatures between 0° C. and RT. The decarboxylation can be carried out by heating the diester in DCM or dichloroethane in the presence of an acid such as TFA or HCl.

Compounds of formula (XVI), wherein $R^3$ is aryl-methyl, can be prepared in two steps starting from halides $R^3$—Z (XVIII), wherein Z is preferably bromide or iodide and $R^3$ is aryl, via (1) a Heck or Suzuki type coupling reaction using standard conditions and (2) a hydrogenation reaction of the obtained cinnamate derivatives in the presence of a catalyst such as palladium in a suitable solvent such as EtOH or EtOAc at temperatures around RT. The Suzuki reaction can be carried out for instance with vinylboronic acid derivatives such as 2-ethoxycarbonylvinylboronic acid pinacol ester in the presence of a suitable base such as $K_2CO_3$ and a palladium catalyst like tetrakis(triphenylphosphine)palladium in a solvent such as EtOH or dioxane preferably at temperatures between RT and 100° C. The Heck coupling reaction can be carried out for instance with methylacrylate in the presence of a base such as $Et_3N$ and a suitable palladium catalyst like tetrakis(triphenylphosphine)palladium in a solvent such as DMF preferably at temperatures between RT and 100° C.

Compounds of formula (XVI), wherein $R^3$ is aryl-ethyl, can be prepared in two steps starting from halides $R^3$—Z (XVIII), wherein Z is preferably bromide or iodide and $R^3$ is aryl, via (1) a Heck type coupling reaction using standard conditions and (2) a hydrogenation reaction of the obtained unsaturated carboxylic ester derivatives in the presence of a catalyst such as palladium in a suitable solvent such as EtOH or EtOAc at temperatures around RT. The Heck coupling reaction can be carried out for instance with methyl 3-butenoate in the presence of a base such as $Et_3N$ and a suitable palladium catalyst like tetrakis(triphenylphosphine)palladium in a solvent such as DMF or $CH_3CN$ preferably at temperatures between RT and 100° C.

Alternatively, compounds of formula (XVI), wherein $R^3$ is aryl-ethyl, can be prepared starting from halides $R^3$—Z (XVIII), wherein Z is preferably bromide or iodide and $R^3$ is aryl, via a Suzuki cross-coupling procedure using the respective trialkylborane such as 9-borabicyclo[3.3.1]nonane-9-butanoic acid methyl ester in the presence of a base like $K_3PO_4$ and a suitable palladium catalyst like dichloro(diphenylphosphinoferrocene)-palladium in a solvent such as THF or DMF preferably at temperatures between RT and 100° C.

Compounds of formula (XVI), wherein $R^3$ is aryloxy or heteroaryloxy, can be prepared by alkylation of the respective hydroxyaryl or hydroxyheteroaryl derivatives with a bromoacetic acid ester derivative in the presence of a base like $K_2CO_3$ in a suitable solvent such as acetone or DMF preferably at temperatures between 0° C. and 90° C.

Hydrolysis of esters (XVI), wherein R represents methyl or ethyl, using standard conditions such as NaOH or LiOH in a mixture of water and a suitable organic solvent system such as MeOH, EtOH or THF gives the respective compounds of formula (III), wherein $R^1$ and $R^2$ represent hydrogen (scheme 7).

Hydrolysis of esters (XVI), wherein R represents tBu can be done using TFA in a suitable solvent like DCM preferably at temperatures around RT.

Alternatively, compounds of formula (III), wherein $R^1$ and $R^2$ represent hydrogen and $R^3$ is aryl-methyl, can be prepared starting from benzaldehydes (XIX), wherein $R^3$ is aryl, via a Knoevenagel type condensation reaction using a malonic acid derivative like malonic acid in the presence of an amine like piperidine/pyridine preferably at temperatures between RT and 100° C. The formed cinnamate derivative can then be hydrogenated under the conditions mentioned above.

Compounds of formula (III), wherein $R^3$ contains a ($C_1$-$C_2$)alkylcarbonyl substituent, can be prepared for instance from compounds of formula (XVIII), wherein R³ contains a carboxylic acid substituent, by formation of the corresponding Weinreb amide using N,O-dimethylhydroxylamine and subsequent treatment with a Grignard reagent like methylmagnesium bromide or ethylmagnesium bromide in a suitable solvent such as THF preferably at temperatures between −78° C. and RT.

Compounds of formula (III), wherein at least one of R¹ and R² is different from hydrogen, can be synthesized starting from compounds of formula (III), wherein R¹ and R² are hydrogen, or of formula (XVI) by alkylation with methyl iodide or ethyl iodide or dihaloalkanes such as 1,2-dibromoethane, 1,3-dibromopropane 1,4-dibromobutane or 1,5-dibromopentane in the presence of a base like NaH, tBuOK or LDA in a suitable organic solvent such as THF or DMF preferably at temperatures between −78° C. and RT (scheme 7).

Compounds of formula (III), wherein R¹ is hydrogen and R² is hydroxy-methyl, can be synthesized starting from compounds of formula (XVI) via a hydroxymethylation reaction using paraformaldehyde being catalyzed by a base such as DBU or NaHCO₃ in a solvent like DMSO or dioxane preferably at temperatures around RT.

Compounds of formula (III), wherein R¹ is hydrogen and R² is heterocyclyl-methyl, can be synthesized starting from compounds of formula (XVI) via (1) a condensation reaction using paraformaldehyde in the presence of a base such as K₂CO₃, NaOMe or NaH in a suitable solvent like DMSO or DMF preferably at temperatures between RT and 100° C. and (2) a Michael addition reaction of the obtained acrylate derivatives with the respective heterocycle such as pyrrolidine in a suitable solvent like THF at temperatures between 0° C. and RT (scheme 7).

Scheme 7: Synthesis of compounds of formula (III)

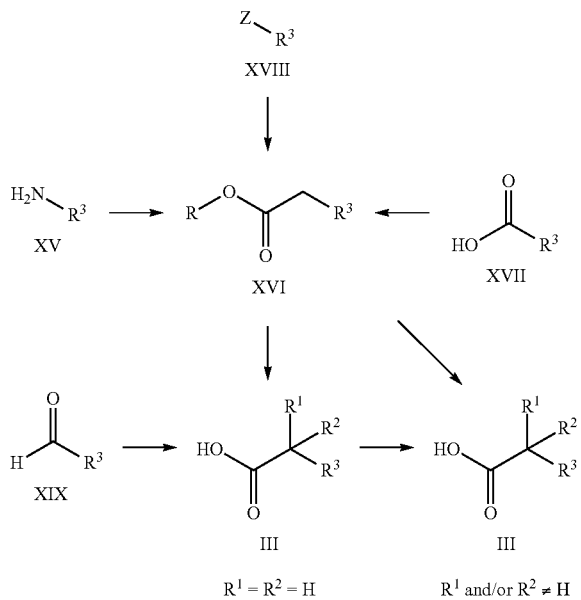

Compounds of formula (IIIa), wherein R¹ is hydrogen and R² and R³ form, together with the carbon atom to which they are attached, an indanyl or a tetrahydronaphthyl group can be prepared in two steps from ketones (XX), wherein R represents a substituent such as halogen and m represents 1, 2 or 3 via (1) reductive cyanation using TosMIC in the presence of a base such as tBuOK in a suitable solvent like dimethoxyethane or EtOH preferably at temperatures between 0° C. and RT to form compounds of formula (XXI) and (2) hydrolysis by heating the nitrile in the presence of an acid such as HCl and/or AcOH preferably at temperatures between 40° C. and 100° C. (scheme 8).

Scheme 8: Synthesis of compounds of formula (IIIa)

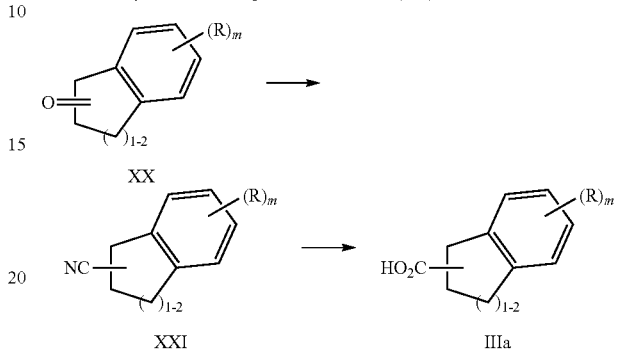

EXPERIMENTAL PART

Abbreviations

As Used Herein and in the Description Above

Ac acetyl
anh. anhydrous
aq aqueous
CC column chromatography
dba dibenzylideneacetone
DBU 1,8-diazabicyclo[5.4.0]undec-7-ene
DCM dichloromethane
DEA diethylamine
Deoxo-Fluor™ bis(2-methoxyethyl)aminosulfur trifluoride
DIPEA diisopropylethylamine
DMF dimethylformamide
DMSO dimethylsulfoxide
DPPA diphenylphosphoryl azide
Et ethyl
EDC.HCl N-(3-dimethylaminopropyl)-N'-ethylcarbodiimide hydrochloride
h hour(s)
Hept heptanes
HOAT 1-hydroxy-7-azabenzotriazole
HOBT 1-hydroxybenzotriazole hydrate
HV high vacuum
ID inner diameter
LC-MS liquid chromatography-mass spectrometry
LDA lithium diisopropylamide
M molar
Me methyl
min minute(s)
N normal
NCS N-chlorosuccinimide
NMP N-methyl-2-pyrrolidone
NMR nuclear magnetic resonance
PG protecting group
Q-Phos 1,2,3,4,5-pentaphenyl-1'-(di-tBu-phosphino)ferrocene
RT room temperature
sat. saturated TBTU O-(benzotriazol-1-yl)-N,N,N',N'-tetramethyluronium tetrafluoroborate
tBu tert.-butyl
TFA trifluoroacetic acid
THF tetrahydrofuran
TMS trimethylsilyl
TosMIC 1-(isocyanomethylsulfonyl)-4-methylbenzene
$t_R$ retention time
UV ultra-violet
Vis visible
Characterization Methods Used NMR: Brucker Avance 400, 400 MHz; chemical shifts are given in ppm relative to the solvent used; multiplicities: s=singlet, d=doublet, t=triplet, q=quadruplet, m=multiplet, br=broad, coupling constants are given in Hz.

LC-MS: Thermo Finnigan MSQ Surveyor MS with Agilent 1100 Binary Pump and DAD. Conditions: eluents: A: $H_2O+0.04\%$ TFA; B: $CH_3CN$; gradient: 5% B→95% B; runtime: 1.5 min; flow: 4.5 mL/min; detection: UV/Vis+MS, $t_R$ is given in min;

LC-MS (A): column Waters XBridge C18, 2.5 μm, 4.6×30 mm

LC-MS (B): column Waters Atlantis T3, 5 μm, 4.6×30 mm

LC-MS (C): column Zorbax SB-aq, 3.5 μm, 4.6×50 mm

Conditions: LC-MS (D): eluents: A: $H_2O+13$ mmol/L $NH_4OH$; B: $CH_3CN$; gradient: 5% B→95% B; runtime: 1.5 min; flow: 4.5 mL/min; detection: UV/Vis+MS, $t_R$ is given in min; column Waters XBridge C18, 2.5 μm, 4.6×50 mm.

LC-MS: Waters Acquity UPLC (ACQ-CM, -ACQ-BSM-ACD-SM)

Conditions: LC-MS (E): eluents: A: $H_2O+0.05\%$ v/v formic acid; B: $CH_3CN+0.045\%$ v/v formic acid; gradient: 2% B→98% B; runtime: 2 min; flow: 1.2 mL/min; detection: UV 214 nm+ELSD and MS; column Acquity UPLC CSH C18 1.7 μm, 2.1×50 mm.

Conditions: LC-MS (F): eluents: A: $H_2O+0.05\%$ v/v TFA; B: $CH_3CN+0.045\%$ v/v TFA; gradient: 2% B→98% B; runtime: 2 min; flow: 1.2 mL/min; detection: UV 214 nm+ELSD and MS; column Acquity UPLC CSH C18 1.7 μm, 2.1×50 mm.

Purification Methods Used

Column chromatography (CC) (method G) was performed using silica gel 60 Merck (0.063-0.200 mm) or using pre-packed cartridges (SNAP KP-SIL™, SNAP KP-NH™, Isolute™) from Biotage.

Preparative LC-MS (normal phase): flow: 40 mL/min. Detection: UV-Vis and/or MS.

Column: Macherey-Nagel Nucleosil SiOH, 10 μM, 21×100 mm

Eluents: A=Hept, B=EtOAc, C=MeOH

| | t (min) | | | | | | | | | |
|---|---|---|---|---|---|---|---|---|---|---|
| | 0 | 0.4 | 0.5 | 6.0 | 6.2 | 7.8 | 7.9 | 8.8 | 8.9 | 9.0 |
| | Conditions (H): | | | | | | | | | |
| % A | 90 | 90 | 70 | 40 | 25 | 25 | 0 | 0 | 90 | 90 |
| % B | 10 | 10 | 30 | 55 | 70 | 70 | 30 | 30 | 10 | 10 |
| % C | 0 | 0 | 0 | 5 | 5 | 5 | 70 | 70 | 0 | 0 |
| | Conditions (I): | | | | | | | | | |
| % A | 90 | 90 | 50 | 20 | 10 | 10 | 0 | 0 | 90 | 90 |
| % B | 10 | 10 | 50 | 65 | 70 | 70 | 30 | 30 | 10 | 10 |
| % C | 0 | 0 | 0 | 15 | 20 | 20 | 70 | 70 | 0 | 0 |

Preparative LC-MS (reverse phase): flow: 75 mL/min. Detection: UV-Vis and/or MS.

XBridge: column Waters XBridge C18, 10 μm, 30×75 mm
Acidic: eluent: A=$H_2O$ with 0.5% formic acid, B=$CH_3CN$
Basic: eluent: A=$H_2O$ with 0.125% $NH_4OH$, B=$CH_3CN$
Apolar gradient: 30% B→95% B over 3.5 min then 95% B over 2.5 min
Normal gradient: 20% B→95% B over 4 min then 95% B over 2 min
Polar gradient: 10% B→95% B over 4 min then 95% B over 2 min
Very polar gradient: 5% B→50% B over 3 min then 50% B→95% B over 1 min and finally 95% B over 2 min
Extremely polar gradient: 0% B over 1 min then 0% B→20% B over 2.5 min then 20% B→95% B over 0.5 min and finally 95% B over 2 min
Methods Used for the Purification of Examples:

| | acidic | basic |
|---|---|---|
| apolar gradient | (J) | (K) |
| normal gradient | (L) | (M) |
| polar gradient | (N) | (P) |

Racemates can be separated into their enantiomeres by preparative chiral HPLC.

The following examples illustrate the invention but do not at all limit the scope thereof.

A. Preparation of Precursors and Intermediates

A.1 Synthesis of Carboxylic Acid Derivatives (III)

A.1.1 Synthesis of 2,4-dichloroanilines (General Procedure)

To a solution of the respective aniline (11.3 mmol) in 50 mL $CH_3CN$ was added NCS (22.6 mmol) at 0° C. After 15 min the cooling bath was removed and the reaction stirred at RT for 2 h and then heated to 40° C. overnight. A solution of 10% aq $Na_2S_2O_3$ was added and the mixture was extracted with EtOAc twice. The combined organic layers were dried over $MgSO_4$ and concentrated in vacuo. The crude was purified by CC using Hept/EtOAc to obtain the desired 2,4-dichloroaniline derivatives.

2,4-Dichloro-6-ethylaniline prepared from 2-ethylaniline;
LC-MS (A): $t_R$=0.89 min; [M+$CH_3CN$+H]+: 231.10.

2,4-Dichloro-6-cyclopropylaniline prepared from 2-cyclopropylaniline;
LC-MS (A): $t_R$=0.92 min; [M+H]+: 202.13.

A.1.2 Synthesis of 3-amino-2-chlorobenzamide

To a solution of 3-amino-2-chlorobenzoic acid (5.8 mmol) in 12 mL DCM were added 3.0 mL DIPEA, HOBT (7.0 mmol) and EDC.HCl (7.0 mmol) followed by the addition of 0.67 mL of a solution of $NH_3$ in water (13M). The mixture was stirred at RT overnight, EtOAc was then added and the mixture was extracted with water, sat. aq. $NaHCO_3$ solution and brine. The organic layer was dried over $MgSO_4$ and concentrated in vacuo to obtain the desired compound as yellow solid.
LC-MS (A): $t_R$=0.17 min; [M+H]+: 170.96.

A.1.3 Synthesis of 3,5-dichloro-2-iodobenzyl acetate

A mixture of 1-(bromomethyl)-3,5-dichloro-2-iodobenzene (1.29 mmol) [WO2011/027156] and sodium acetate (9.91 mmol) in 4 mL AcOH was heated to 100° C. for 1 h and then to 80° C. for 20 h. The mixture was diluted with DCM and extracted with water and brine. The organic layer was dried over $MgSO_4$ and concentrated in vacuo. Purification by CC (KP-SIL™ from Biotage) using Hept to Hept/EtOAc (9/1) gives the desired compound as white solid.

LC-MS (A): $t_R$=0.97 min; $^1$H NMR ($(CD_3)_2SO$) δ: 7.77 (d, 1H), 7.44 (d, 1H), 5.08 (s, 2H), 2.13 (s, 3H).

A.1.4 Synthesis of 3-bromo-2-chloro-6-fluorobenzonitrile

A.1.4.1 Synthesis of 3-bromo-2-chloro-6-fluorobenzamide

This compound was prepared using a method analogous to that of 3-amino-2-chlorobenzamide (A.1.2), 3-bromo-2-chloro-6-fluorobenzoic acid replacing 3-amino-2-chlorobenzoic acid;

LC-MS (A): $t_R$=0.52 min; [M+H]+: 253.81.

A.1.4.2 Synthesis of 3-bromo-2-chloro-6-fluorobenzonitrile

To a solution of 3-bromo-2-chloro-6-fluorobenzamide (3.56 mmol) in 50 mL DCM were added 1.5 mL $Et_3N$ followed by trifluoromethanesulfonic acid anhydride (7.11 mmol) at 0° C. The ice bath was removed and the reaction mixture was stirred at RT. After 30 min, water was added and the mixture was extracted with DCM (3×). The combined organic layers were dried over $MgSO_4$ and concentrated in vacuo to obtain the desired compound as brown solid.

LC-MS (A): $t_R$=0.80 min; $^1$H NMR ($(CD_3)_2SO$) δ: 8.23 (dd, 1H), 7.56 (t, 1H).

A.1.5 Synthesis of 2-chloro-1-iodo-3-(trifluoromethoxy)benzene

To a solution of 1-chloro-2-(trifluoromethoxy)benzene (2.54 mmol) in 10 mL THF were added 1.42 mL n-BuLi (2.5 M solution in hexane) at −78° C. After 40 min, a solution of iodine (2.8 mmol) in 2.5 mL THF was added and stirring was continued at RT overnight.

The reaction was quenched with water under cooling and extracted with EtOAc (3×). The combined organic layers were dried over $MgSO_4$ and concentrated in vacuo. Purification by CC (KP-SIL™ from Biotage) using Hept to Hept/EtOAc (4/1) gives the desired compound (in a regioisomeric mixture as the major product) as colorless oil.

LC-MS (A): $t_R$=0.99 min; $^1$H NMR ($(CD_3)_2SO$) δ: 7.98 (dd, 1H), 7.70 (dd, 1H), 7.21 (t, 1H).

A.1.6 Synthesis of 1-(3-bromo-2-chlorophenyl)ethanone

A.1.6.1 Synthesis of 3-bromo-2-chloro-N-methoxy-N-methylbenzamide

To a solution of 3-bromo-2-chlorobenzoic acid (1.79 mmol) in 12 mL THF were added N,O-dimethylhydroxylamine HCl (2.32 mmol), EDC.HCl (4.29 mmol) and pyridine (2.68 mmol) at 0° C. The cooling bath was removed and stirring was continued at RT overnight. The reaction was diluted with DCM and extracted with water, sat. aq. $NH_4Cl$ solution, sat. aq. $NaHCO_3$ solution, dried over $MgSO_4$ and concentrated in vacuo. Purification by CC (KP-SIL™ from Biotage) using Hept to EtOAc gives the desired compound as colorless oil.

LC-MS (C): $t_R$=0.76 min; [M+H]+: 277.90.

A.1.6.2 Synthesis of 1-(3-bromo-2-chlorophenyl)ethanone

To a solution of 3-bromo-2-chloro-N-methoxy-N-methylbenzamide (0.71 mmol) in 7 mL THF was added a solution of MeMgBr (4.31 mmol, 3M solution in $Et_2O$) at 0° C. The cooling bath was removed after 1 h and stirring was continued at RT overnight. The reaction was quenched with water and sat. aq. $NH_4Cl$ solution under cooling. The mixture was extracted with EtOAc (3×), the combined organic layers were washed with brine, dried over $MgSO_4$ and concentrated in vacuo. Purification by CC (KP-SIL™ from Biotage) using Hept to Hept/EtOAc (85/15) gives the desired compound as colorless oil;

LC-MS (C): $t_R$=0.84 min; $^1$H NMR ($(CD_3)_2SO$) δ: 7.91 (d, 1H), 7.65 (d, 1H), 7.39 (t, 1H), 2.58 (s, 3H).

A.1.7 Synthesis of 3-bromo-2,6-dichlorobenzonitrile

A.1.7.1 Synthesis of 3-amino-2,6-dichlorobenzonitrile

A solution of 2,6-dichloro-3-nitrobenzonitrile (1.38 mmol) and $SnCl_2$ dihydrate (4.15 mmol) in 3 mL DMF was heated to 100° C. for 10 min under microwave conditions. The reaction mixture was diluted with water, basified with 1M NaOH solution to pH 11-12 and extracted with EtOAc (3×). The combined organic layers were washed with brine, dried over $MgSO_4$ and concentrated in vacuo to give the desired product as brown solid;

LC-MS (C): $t_R$=0.78 min; $^1$H NMR ($(CD_3)_2SO$) δ: 7.36 (d, 1H), 7.07 (d, 1H).

A.1.7.2 Synthesis of 3-bromo-2,6-dichlorobenzonitrile

To 1 mL of conc. $H_2SO_4$ was portionwise added sodium nitrite (1.38 mmol). After complete dissolution, a solution of 3-amino-2,6-dichlorobenzonitrile (1.24 mmol) in 2.5 mL glacial acetic acid was added at 0° C. After 30 min at 0° C., a precooled solution of CuBr (2.76 mmol) in 0.5 mL HBr (48% in $H_2O$) was slowly added. The reaction was stirred at 0° C. for 45 min and then at RT for 45 min. The mixture was quenched with water and extracted with EtOAc (3×). The combined organic layers were washed with brine, dried over $MgSO_4$ and concentrated in vacuo to give the desired product as brown solid.

LC-MS (C): $t_R$=0.90 min; $^1$H NMR ($(CD_3)_2SO$) δ: 8.15 (d, 1H), 7.70 (d, 1H).

A.1.8 Synthesis of 3-bromo-2-(trifluoromethyl)benzonitrile

A solution of 2-bromo-6-fluorobenzonitrile (2.06 mmol) and KCN (4.12 mmol) in 2.5 mL DMSO was heated to 85° C. for 5 h, then stirred at RT overnight and heated again to 90° C. for another 5 h. The mixture was cooled to RT, quenched with 10% aq. $Na_2CO_3$ solution and extracted with EtOAc (3×). The combined organic layers were washed with brine, dried over $MgSO_4$ and concentrated in vacuo. Purification by CC (KP-SIL™ from Biotage) using Hept to Hept/EtOAc (5/1) gives the desired compound as white solid;
LC-MS (C): $t_R$=0.87 min; $^1$H NMR ((CD$_3$)$_2$SO) δ: 8.27 (d, 1H), 8.16 (d, 1H), 7.79 (t, 1H).

A.1.9 Synthesis of 1-bromo-2-chloro-3-(difluoromethyl)benzene

A.1.9.1 Synthesis of 2-chloro-1-(difluoromethyl)-3-nitrobenzene

A solution of 2-chloro-3-nitrobenzaldehyde (1.08 mmol) and Deoxo-Fluor™ (3.23 mmol) in 1 mL DCM was stirred at RT overnight. The reaction mixture was diluted with DCM, extracted with sat. aq. NaHCO$_3$ solution (2×) and brine. The organic layer was dried over MgSO$_4$ and concentrated in vacuo. Purification by CC (KP-SIL™ from Biotage) using Hept to Hept/EtOAc (85/15) gives the desired compound as yellow oil;
LC-MS (C): $t_R$=0.85 min; $^1$H NMR ((CD$_3$)$_2$SO) δ: 8.25 (d, 1H), 8.02 (d, 1H), 7.78 (t, 1H), 7.35 (t, 1H).

A.1.9.2 Synthesis of 2-chloro-3-(difluoromethyl)aniline

A solution of 2-chloro-1-(difluoromethyl)-3-nitrobenzene (0.43 mmol) and SnCl$_2$ dihydrate (0.86 mmol) in 1 mL EtOH was heated to 110° C. for 6 min in a closed vial. At RT, the mixture was diluted with water, basified with 1M NaOH solution to pH 13-14 and extracted with EtOAc (3×). The combined organic layers were washed with brine, dried over MgSO$_4$ and concentrated in vacuo to give the desired product as brown oil;
LC-MS (C): $t_R$=0.77 min; [M+CH$_3$CN+H]+: 219.13.

A.1.9.3 Synthesis of 1-bromo-2-chloro-3-(difluoromethyl)benzene

To a solution of CuBr$_2$ (0.557 mmol) in 1 mL CH$_3$CN was added tBu-nitrite (0.669 mmol) at 0° C. before a solution of 2-chloro-3-(difluoromethyl)aniline (0.372 mmol) in 1 mL CH$_3$CN was added. The reaction mixture was stirred at 0° C. for 70 min. The mixture was then quenched with 1M HCl solution and extracted with EtOAc (3×). The combined organic layers were washed with brine, dried over MgSO$_4$ and concentrated in vacuo to give the desired product as orange oil;
LC-MS (C): $t_R$=0.91 min; [M+CH$_3$CN+H]+: 282.25.

A.1.10 Synthesis of Esters (General Procedure A)

To a suspension of CuCl$_2$ (11 mmol) in 90 mL CH$_3$CN was added tBuONO (15 mmol) followed by dropwise addition of 1,1-dichloroethylene (146 mmol). A solution of the respective aniline (8 mmol) in 10 mL CH$_3$CN was slowly added. After stirring for 5 h at RT the reaction was quenched with 20% aq HCl solution and extracted with EtOAc 3 times. The combined organic layers were dried over MgSO$_4$. After removal of the solvent the crude was redissolved in 50 mL MeOH. After addition of 9 mL of a 30% solution of NaOMe in MeOH the mixture was refluxed for 5 h. Then, 1.8 mL concentrated H$_2$SO$_4$ were added and the mixture was heated to reflux for another 1 h. After concentration in vacuo the resulting solid was partitioned between water and DCM. The water phase was extracted with DCM twice. The combined organic layers were dried over MgSO$_4$. Purification by CC using Hept/EtOAc gives the desired ester derivatives.

2,4-Dichloro-6-methylphenylacetic acid methyl ester prepared from 2,4-dichloro-6-methylaniline;
LC-MS (A): $t_R$=0.90 min; $^1$H NMR (CDCl$_3$) δ: 7.28 (s, 1H), 7.12 (s, 1H), 3.83 (s, 2H), 3.72 (s, 3H), 2.32 (s, 3H).

2,4-Dichloro-6-ethylphenylacetic acid methyl ester prepared from 2,4-dichloro-6-ethylaniline;
LC-MS (A): $t_R$=0.95 min; $^1$H NMR (CDCl$_3$) δ: 7.29 (s, 1H), 7.14 (s, 1H), 3.85 (s, 2H), 3.72 (s, 3H), 2.64 (q, 2H), 1.22 (t, 3H).

2,4-Dichloro-6-cyclopropylphenylacetic acid methyl ester prepared from 2,4-dichloro-6-cyclopropylaniline;
LC-MS (A): $t_R$=0.96 min; $^1$H NMR (CDCl$_3$) δ: 7.28 (s, 1H), 7.02 (s, 1H), 4.05 (s, 2H), 3.73 (s, 3H), 1.89 (m, 1H), 0.98 (m, 2H), 0.68 (m, 2H).

2,4-Dichloro-6-trifluoromethylphenylacetic acid methyl ester prepared from 2,4-dichloro-6-trifluoromethylaniline;
LC-MS (A): $t_R$=0.93 min; $^1$H NMR ((CD$_3$)$_2$SO) δ: 8.11 (s, 1H), 7.88 (s, 1H), 3.97 (s, 2H), 3.65 (s, 3H).

2,4-Dichloro-6-iodophenylacetic acid methyl ester prepared from 2,4-dichloro-6-iodoaniline;
LC-MS (A): $t_R$=0.95 min; $^1$H NMR ((CD$_3$)$_2$SO) δ: 7.99 (s, 1H), 7.75 (s, 1H), 4.04 (s, 2H), 3.66 (s, 3H).

2-Chloro-3-carbamoylphenylacetic acid methyl ester prepared from 3-amino-2-chlorobenzamide;
LC-MS (A): $t_R$=0.42 min; $^1$H NMR ((CD$_3$)$_2$SO) δ: 7.90 (brs, 1H), 7.57 (brs, 1H), 7.45 (m, 1H), 7.35 (m, 2H), 3.86 (s, 2H), 3.36 (s, 3H).

A.1.11 Synthesis of Esters (General Procedure B)

To a mixture of the carboxylic acid (7.66 mmol) in 25 mL DCM was added oxalylchloride (11.5 mL) followed by a few drops of DMF at −5° C. After stirring for 2 h at RT the solvent was removed in vacuo and the residue was redissolved in 42 mL THF. The mixture was cooled to −5° C. when trimethylsilyldiazomethane (17.2 mmol, 2M solution in hexanes) was added and the reaction mixture was allowed to warm to RT over 2 h. After evaporation of the solvent in vacuo the crude was purified by CC using Hept/EtOAc. The isolated α-diazoketone was dissolved in 39 mL MeOH, silver benzoate (3.3 mmol) was added followed by dropwise addition of 11 mL Et$_3$N while cooling in an ice bath. The black solution was stirred at RT for 1 day, concentrated in vacuo and purified by CC using Hept/EtOAc to give the desired ester derivatives.

2,4-Dichloro-6-fluorophenylacetic acid methyl ester prepared from 2,4-dichloro-6-fluorobenzoic acid;
LC-MS (A): $t_R$=0.85 min; $^1$H NMR (CDCl$_3$) δ: 7.07 (s, 1H), 7.04 (s, 1H), 3.80 (s, 2H), 3.72 (s, 3H).

A.1.12 Synthesis of Esters (General Procedure C)

To a mixture of the respective halide (0.979 mmol), Pd(dba)$_2$ (0.049 mmol) and Q-Phos (0.049 mmol) in 2.5 mL THF were added 2.15 mL of 2-tBu-oxy-2-oxoethylzinc chloride (0.5M solution in Et$_2$O). The reaction mixture was flushed with argon and then heated to 70° C. for 6 h. After concentration of the solvent in vacuo the residue was dissolved in EtOAc and extracted with water and brine. The organic layer was dried over MgSO$_4$, concentrated in vacuo and purified by CC using Hept/EtOAc to give the desired ester derivatives.

2-Chloro-4-(trifluoromethyl)phenylacetic acid tBu-ester prepared from 3-chloro-4-iodobenzotrifluoride;
LC-MS (A): t$_R$=1.02 min; $^1$H NMR ((CD$_3$)$_2$SO) δ: 7.87 (s, 1H), 7.71 (d, 1H), 7.65 (d, 1H), 3.83 (s, 2H), 1.41 (s, 9H).

2-Chloro-4-cyanophenylacetic acid tBu-ester prepared from 4-bromo-3-chlorobenzonitrile;
LC-MS (A): t$_R$=0.89 min; $^1$H NMR ((CD$_3$)$_2$SO) δ: 8.06 (d, 1H), 7.82 (dd, 1H), 7.62 (d, 1H), 3.83 (s, 2H), 1.40 (s, 9H).

3-Chloro-2-(trifluoromethyl)phenylacetic acid tBu-ester prepared from 2-bromo-6-chlorobenzotrifluoride;
LC-MS (A): t$_R$=0.98 min; $^1$H NMR ((CD$_3$)$_2$SO) δ: 7.62 (m, 2H), 7.43 (d, 1H), 3.89 (m, 2H), 1.38 (s, 9H).

2-(2-Acetoxymethyl)-4,6-dichlorophenylacetic acid tBu-ester prepared from 3,5-dichloro-2-iodobenzyl acetate;
LC-MS (A): t$_R$=0.99 min; $^1$H NMR ((CD$_3$)$_2$SO) δ: 7.66 (d, 1H), 7.48 (dd, 1H), 5.11 (s, 2H), 3.77 (s, 2H), 2.03 (s, 3H), 1.39 (s, 9H).

2-Chloro-3-cyano-4-fluorophenylacetic acid tBu-ester prepared from 3-bromo-2-chloro-6-fluorobenzonitrile;
LC-MS (A): t$_R$=0.89 min; $^1$H NMR ((CD$_3$)$_2$SO) δ: 7.85 (dd, 1H), 7.56 (t, 1H), 3.82 (s, 2H), 1.40 (s, 9H).

2-Chloro-3-(trifluoromethoxy)phenylacetic acid tBu-ester prepared from 2-chloro-1-iodo-3-(trifluoromethoxy)benzene;
LC-MS (A): t$_R$=1.02 min; $^1$H NMR ((CD$_3$)$_2$SO) δ: 7.61 (dd, 1H), 7.43 (m, 2H), 3.73 (s, 2H), 1.39 (s, 9H).

3-Acetyl-2-chlorophenylacetic acid tBu-ester prepared from 1-(3-bromo-2-chlorophenyl)ethanone;
LC-MS (C): t$_R$=0.91 min; $^1$H NMR ((CD$_3$)$_2$SO) δ: 7.54 (m, 2H), 7.40 (t, 1H), 3.77 (s, 2H), 2.56 (s, 3H), 1.41 (s, 9H).

2,4-Dichloro-3-cyanophenylacetic acid tBu-ester prepared from 3-bromo-2,6-dichlorobenzonitrile;
LC-MS (C): t$_R$=0.96 min; $^1$H NMR ((CD$_3$)$_2$SO) δ: 7.77 (d, 1H), 7.47 (d, 1H), 3.83 (s, 2H), 1.40 (s, 9H).

3-Cyano-2-(trifluoromethyl)phenylacetic acid tBu-ester prepared from 3-bromo-2-(trifluoromethyl)benzonitrile;
LC-MS (C): t$_R$=0.94 min; [M+H]+: 286.27.

2-Chloro-3-(difluoromethyl)phenylacetic acid tBu-ester prepared from 1-bromo-2-chloro-3-(difluoromethyl)benzene;
LC-MS (C): t$_R$=0.96 min; [M+H]+: 276.18.

A.1.13 Synthesis of 2,4-dichloro-6-cyanophenylacetic acid methyl ester

A mixture of 2,4-dichloro-6-iodophenylacetic acid methyl ester (0.95 mmol), Zn(CN)$_2$ (0.95 mmol) and tetrakis(triphenylphosphine)palladium (0.05 mmol) in 1.5 mL anhydrous NMP was degassed and heated under argon in a closed vial to 110° C. for 2.5 h. The reaction mixture was cooled to RT, quenched with 10% aq Na$_2$CO$_3$ solution and extracted with EtOAc (3×). The combined organic layers were dried over MgSO$_4$ and concentrated in vacuo. Purification by CC using Hept/EtOAc (9/1) gives the desired product as yellow oil.
LC-MS (A): t$_R$=0.80 min; $^1$H NMR ((CD$_3$)$_2$SO) δ: 8.15 (s, 1H), 8.12 (s, 1H), 4.03 (s, 2H), 3.68 (s, 3H).

A.1.14 Synthesis of 2-chloro-3-cyanophenylacetic acid methyl ester

To a solution of 2-chloro-3-carbamoylphenylacetic acid methyl ester (0.35 mmol) in 5 mL DCM were added 0.15 mL Et$_3$N followed by trifluoromethanesulfonic acid anhydride (0.70 mmol) at 0° C. The ice bath was removed and the reaction mixture was stirred at RT. After 30 min, water was added and the mixture was extracted with DCM (3×). The combined organic layers were dried over MgSO$_4$ and concentrated in vacuo to obtain the desired compound as brown oil.
LC-MS (A): t$_R$=0.68 min; $^1$H NMR ((CD$_3$)$_2$SO) δ: 7.94 (m, 1H), 7.79 (m, 1H), 7.55 (t, 1H), 3.95 (s, 2H), 3.65 (s, 3H).

A.1.15 Synthesis of 2-(2,4-dichlorophenyl)-3-hydroxypropanoic acid methyl ester To a suspension of 2,4-dichlorophenylacetic acid methyl ester (1.38 mmol) and paraformaldehyde (1.45 mmol) in 2.7 mL DMSO was added NaHCO$_3$ (0.07 mmol). The reaction mixture was stirred at RT for 2 h and then quenched with water. The mixture was neutralized with 1M HCl solution and extracted with EtOAc (2×). The combined organic layers were dried over MgSO$_4$ and concentrated in vacuo. Purification by CC (KP-SIL™ from Biotage) using Hept to Hept/EtOAc (1/1) gives the desired compound as colorless oil;
LC-MS (B): t$_R$=0.77 min; $^1$H NMR ((CD$_3$)$_2$SO) δ: 7.64 (d, 1H), 7.46 (m, 2H), 5.14 (t, 1H), 4.18 (m, 1H), 3.92 (m, 1H), 3.72 (m, 1H), 3.62 (s, 3H).

A.1.16 Synthesis of 2-(2,4-dichlorophenyl)-3-(pyrrolidin-1-yl)propanoic acid methyl ester

A.1.16.1 Synthesis of 2-(2,4-dichlorophenyl)acrylic acid methyl ester

To a solution of 2,4-dichlorophenylacetic acid methyl ester (4.62 mmol) in 9 mL DMSO were added paraformaldehyde (4.85 mmol) and NaOMe (0.23 mmol). The reaction mixture was stirred at RT for 1 h and then poured into ice cold water. The mixture was neutralized with 1M HCl solution and extracted with toluol (3×). The combined organic layers were washed with aq. NaCl solution, dried over MgSO$_4$ and concentrated in vacuo. Purification by CC (KP-SIL™ from Biotage) using Hept/EtOAc (9/1 to 8/2) gives the desired compound as colorless oil;

LC-MS (A): $t_R$=0.89 min; $^1$H NMR (CDCl$_3$) δ: 7.43 (d, 1H), 7.27 (d, 1H), 7.22 (s, 1H), 6.56 (d, 1H), 5.81 (d, 1H), 3.80 (s, 3H).

A.1.16.2 Synthesis of 2-(2,4-dichlorophenyl)-3-(pyrrolidin-1-yl)propanoic acid methyl ester To a solution of 2-(2,4-dichlorophenyl)acrylic acid methyl ester (0.70 mmol) in 2 mL THF was added pyrrolidine (0.77 mmol) at 0° C. The reaction mixture was stirred at 0° C. for 50 min, diluted with DCM and washed with water. The organic layer was dried over MgSO$_4$ and concentrated in the vacuo to give the desired compound as pinkish oil;

LC-MS (B): $t_R$=0.56 min; [M+H]+: 302.28.

A.1.17 Synthesis of Carboxylic Acid Derivatives (General Procedure A)

To a solution of the respective ester (4.9 mmol) in 15 mL MeOH was added LiOH (14.7 mmol), dissolved in 1 mL H$_2$O. After stirring at RT overnight the MeOH was removed and the residue dissolved in water. The pH was adjusted to pH1, the precipitate was filtrated off and dried in vacuo to give the desired derivatives.

2,4-Dichloro-6-methylphenylacetic acid prepared from 2,4-dichloro-6-methylphenylacetic acid methyl ester;

LC-MS (A): $t_R$=0.74 min; $^1$H NMR ((CD$_3$)$_2$SO) δ: 12.6 (brs, 1H), 7.45 (s, 1H), 7.32 (s, 1H), 3.74 (s, 2H), 2.29 (s, 3H).

2,4-Dichloro-6-ethylphenylacetic acid prepared from 2,4-dichloro-6-ethylphenylacetic acid methyl ester;

LC-MS (A): $t_R$=0.79 min; $^1$H NMR ((CD$_3$)$_2$SO) δ: 12.5 (brs, 1H), 7.46 (s, 1H), 7.29 (s, 1H), 3.75 (s, 2H), 2.63 (q, 2H), 1.12 (t, 3H).

2,4-Dichloro-6-cyclopropylphenylacetic acid prepared from 2,4-dichloro-6-cyclopropylphenylacetic acid methyl ester;

LC-MS (A): $t_R$=0.81 min; $^1$H NMR ((CD$_3$)$_2$SO) δ: 12.5 (brs, 1H), 7.45 (s, 1H), 7.08 (s, 1H), 3.92 (s, 2H), 1.95 (m, 1H), 0.94 (m, 2H), 0.68 (m, 2H).

2,4-Dichloro-6-trifluoromethylphenylacetic acid prepared from 2,4-dichloro-6-trifluoromethylphenylacetic acid methyl ester;

LC-MS (A): $t_R$=0.78 min; $^1$H NMR ((CD$_3$)$_2$SO) δ: 12.8 (brs, 1H), 8.08 (s, 1H), 7.86 (s, 1H), 3.86 (s, 2H).

2,4-Dichloro-6-cyanophenylacetic acid prepared from 2,4-dichloro-6-cyanophenylacetic acid methyl ester;

LC-MS (A): $t_R$=0.65 min; $^1$H NMR ((CD$_3$)$_2$SO) δ: 13.0 (brs, 1H), 8.12 (s, 1H), 8.10 (s, 1H), 3.92 (s, 2H).

2,4-Dichloro-6-fluorophenylacetic acid prepared from 2,4-dichloro-6-fluorophenylacetic acid methyl ester;

LC-MS (A): $t_R$=0.70 min; $^1$H NMR (CDCl$_3$) δ: 7.11 (s, 1H), 7.08 (s, 1H), 3.87 (s, 2H).

2-Chloro-3-cyanophenylacetic acid prepared from 2-chloro-3-cyanophenylacetic acid methyl ester;

LC-MS (A): $t_R$=0.53 min; $^1$H NMR ((CD$_3$)$_2$SO) δ: 12.6 (brs, 1H), 7.91 (m, 1H), 7.77 (m, 1H), 7.53 (t, 1H), 3.84 (s, 2H).

2-Chloro-3-carbamoylphenylacetic acid prepared from 2-chloro-3-carbamoylphenylacetic acid methyl ester;

LC-MS (A): $t_R$=0.30 min; [M+H]+: 214.01.

2-(2,4-Dichlorophenyl)-3-hydroxypropanoic acid prepared from 2-(2,4-dichlorophenyl)-3-hydroxypropanoic acid methyl ester;

LC-MS (B): $t_R$=0.64 min; $^1$H NMR ((CD$_3$)$_2$SO) δ: 12.6 (brs, 1H), 7.62 (d, 1H), 7.45 (m, 2H), 5.04 (brs, 1H), 4.09 (t, 1H), 3.89 (m, 1H), 3.71 (m, 1H).

2-(2,4-dichlorophenyl)-3-(pyrrolidin-1-yl)propanoic acid prepared from 2-(2,4-dichlorophenyl)-3-(pyrrolidin-1-yl) propanoic acid methyl ester;

LC-MS (B): $t_R$=0.50 min; [M+H]+: 288.28.

A.1.18 Synthesis of Carboxylic Acid Derivatives (General Procedure B)

To a solution of the respective ester (0.44 mmol) in 1 mL DCM was added TFA (0.44 mmol). After stirring at RT for 1 h, the reaction was quenched with 10% aq. Na$_2$CO$_3$ solution and extracted with DCM. The pH of the aqueous layer was adjusted to pH1-2 and extracted with DCM (3×). The combined organic layers were dried over MgSO$_4$ and concentrated in vacuo to give the desired derivatives.

2-Chloro-4-(trifluoromethyl)phenylacetic acid prepared from 2-chloro-4-(trifluoromethyl)phenylacetic acid tBu-ester;

LC-MS (A): $t_R$=0.73 min; $^1$H NMR ((CD$_3$)$_2$SO) δ: 12.6 (brs, 1H), 7.87 (s, 1H), 7.68 (m, 2H), 3.84 (s, 2H).

2-Chloro-4-cyanophenylacetic acid prepared from 2-chloro-4-cyanophenylacetic acid tBu-ester;

LC-MS (A): $t_R$=0.56 min; $^1$H NMR ((CD$_3$)$_2$SO) δ: 12.6 (brs, 1H), 8.06 (d, 1H), 7.81 (dd, 1H), 7.63 (d, 1H), 3.84 (s, 2H).

3-Chloro-2-(trifluoromethyl)phenylacetic acid prepared from 3-chloro-2-(trifluoromethyl)phenylacetic acid tBu-ester;

LC-MS (A): $t_R$=0.69 min; $^1$H NMR ((CD$_3$)$_2$SO) δ: 12.5 (brs, 1H), 7.62 (m, 2H), 7.44 (d, 1H), 3.90 (m, 2H).

2-(2-Acetoxymethyl)-4,6-dichlorophenylacetic acid prepared from 2-(2-acetoxymethyl)-4,6-dichlorophenylacetic acid tBu-ester;
LC-MS (D): $t_R$=0.55 min; [M−H]−: 275.03.

2-Chloro-3-cyano-4-fluorophenylacetic acid prepared from 2-chloro-3-cyano-4-fluorophenylacetic acid tBu-ester
LC-MS (D): $t_R$=0.49 min; [M−H]−: 212.10.

2-Chloro-3-(trifluoromethoxy)phenylacetic acid prepared from 2-chloro-3-(trifluoromethoxy)phenylacetic acid tBu-ester
LC-MS (D): $t_R$=0.57 min; [M−H]−: 253.12.

3-Acetyl-2-chlorophenylacetic acid prepared from 3-acetyl-2-chlorophenylacetic acid tBu-ester
LC-MS (D): $t_R$=0.41 min; [M−H]−: 211.14.

2,4-Dichloro-3-cyanophenylacetic acid prepared from 2,4-dichloro-3-cyanophenylacetic acid tBu-ester;
LC-MS (C): $t_R$=0.72 min; $^1$H NMR (($CD_3$)$_2$SO) δ: 12.7 (brs, 1H), 7.79 (m, 2H), 3.84 (m, 2H).

3-Cyano-2-(trifluoromethyl)phenylacetic acid prepared from 3-cyano-2-(trifluoromethyl)phenylacetic acid tBu-ester
LC-MS (D): $t_R$=0.31 min; [M−H]−: 228.12.

2-Chloro-3-(difluoromethyl)phenylacetic acid prepared from 2-chloro-3-(difluoromethyl)phenylacetic acid tBu-ester
LC-MS (D): $t_R$=0.43 min; [M−H]−: 219.13.

A.1.19 Synthesis of Carboxylic Acid Derivatives (General Procedure C)

To a solution of diisopropylamine (16.1 mmol) in 15 mL THF were added 6.4 mL n-BuLi (2.5M solution in hexanes) at −30° C. and the mixture was stirred for 30 min at this temperature. After cooling to −78° C., a solution of the respective carboxylic acid (7.3 mmol) in 5 mL THF was slowly added and stirring was continued at −30° C. for 1 h. After cooling to −78° C., the respective alkylating agent (11.0 mmol) was added and stirring was continued for another 2 h. The reaction was quenched with 2M HCl solution and extracted with DCM (3×). The combined organic layers were dried over MgSO$_4$ and concentrated in vacuo. Purification by CC using Hept/EtOAc gives the desired derivatives.

2-(2,4-Dichlorophenyl)propanoic acid prepared from 2,4-dichlorophenylacetic acid and iodomethane;
LC-MS (A): $t_R$=0.75 min; $^1$H NMR (MeOD) δ: 7.48 (brs, 1H), 7.37 (dd, 2H), 4.16 (m, 1H), 1.49 (d, 3H).

2-(2,4-Dichlorophenyl)propanoic acid-(methyl-D3)

prepared from 2,4-dichlorophenylacetic acid and iodomethane-D3;
LC-MS (A): $t_R$=0.76 min; $^1$H NMR (CDCl$_3$) δ: 7.43 (s, 1H), 7.30 (dd, 2H), 4.22 (s, 1H).

2-(2,4-Dichlorophenyl)butanoic acid prepared from 2,4-dichlorophenylacetic acid and iodoethane;
LC-MS (A): $t_R$=0.82 min; $^1$H NMR (CDCl$_3$) δ: 7.43 (brs, 1H), 7.34 (d, 1H), 7.26 (d, 1H), 4.09 (t, 1H), 2.12 (m, 1H), 1.83 (m, 1H), 0.95 (t, 3H).

2-(2-chloro-3-(trifluoromethyl)phenyl)propanoic acid prepared from 2-chloro-3-(trifluoromethyl)phenylacetic acid and iodomethane;
LC-MS (A): $t_R$=0.76 min; $^1$H NMR (CDCl$_3$) δ: 7.67 (d, 1H), 7.58 (d, 1H), 7.40 (t, 1H), 4.42 (m, 1H), 1.59 (d, 3H).

2-(2-chloro-3-(trifluoromethyl)phenyl)propanoic acid-(methyl-D3)

prepared from 2-chloro-3-(trifluoromethyl)phenylacetic acid and iodomethane-D3;
LC-MS (C): $t_R$=0.82 min; $^1$H NMR (CDCl$_3$) δ: 7.66 (d, 1H), 7.58 (d, 1H), 7.40 (t, 1H), 4.39 (s, 1H).

A.1.20 Synthesis of 5,7-dichloro-2,3-dihydro-1H-indene-1-carboxylic acid

A.1.20.1 Synthesis of 5,7-dichloro-2,3-dihydro-1H-indene-1-carbonitrile

To a solution of 5,7-dichloro-1-indanone (2.24 mmol) and TosMIC (6.71 mmol) in 25 mL 1,2-dimethoxyethan and 1 mL EtOH was added tBuOK (6.71 mmol) at 5° C. The cooling bath was removed and the reaction mixture was stirred at RT for 1 h. The reaction was quenched with water and extracted with EtOAc (3×). The combined organic layers were dried over MgSO$_4$ and concentrated in vacuo. Purification by CC using Hept/EtOAc (7/3) gives the desired compound as yellow solid.

LC-MS (C): $t_R$=0.90 min; [M+CH$_3$CN+H]+: 254.01.

A.1.20.2 Synthesis of 5,7-dichloro-2,3-dihydro-1H-indene-1-carboxylic acid

A suspension of 5,7-dichloro-2,3-dihydro-1H-indene-1-carbonitrile (0.77 mmol) in 2 mL 25% HCl solution and 2 mL AcOH was heated to 100° C. for 5 h. At RT, the reaction was quenched with water and extracted with EtOAc (3×). The combined organic layers were dried over MgSO$_4$ and concentrated in vacuo to give the desired compound as brown solid.

LC-MS (C): $t_R$=0.72 min; [M+H]+: 230.08.

A.2 Synthesis of Amines of Formula (II)

A.2.1 Synthesis of 2,3-dihydrofuro[2,3-b]pyridin-3-amine

A.2.1.1 Synthesis of furo[2,3-b]pyridin-3(2H)-one O-methyloxime

To a solution of furo[2,3-b]pyridine-3(2H)-one (78.3 mmol) [J. Heterocyclic Chem., 23, 1465 (1986)] in 500 mL EtOH were added O-methyl-hydroxylamine (157 mmol) and NaOAc (157 mmol). After heating to reflux for 2 h the reaction mixture was concentrated in vacuo to half of its volume. Water and DCM were added and the aqueous phase was extracted 3 times with DCM. The combined organic layers were dried over $MgSO_4$ and concentrated in vacuo. Purification by CC using Hept/EtOAc (5/1 to 1/1) gives the desired product as yellow oil;

LC-MS (A): $t_R$=0.50 min; [M+H]+: 165.23.

A.2.1.2 Synthesis of 2,3-dihydrofuro[2,3-b]pyridin-3-amine

To a solution of furo[2,3-b]pyridin-3(2H)-one O-methyloxime (22.2 mmol) in 25 mL 7N $NH_3$ in MeOH was added Actimet M Raney-Nickel (3 g) and the reaction mixture was stirred under a $H_2$ atmosphere at 5 bar overnight. The mixture was then filtered over Celite, washed with 100 mL MeOH and concentrated in vacuo to give the title compound as brown solid;

LC-MS (A): $t_R$=0.35 min; [M+H]+: 137.16.

A.2.1.3 Synthesis of tBu-(2,3-dihydrofuro[2,3-b]pyridin-3-yl)carbamate

To a solution of 2,3-dihydrofuro[2,3-b]pyridin-3-amine (7.4 mmol) in 15 mL THF, 2 mL DCM and 1.52 mL DIPEA was added di-tBu-carbonate (8.1 mmol) at 0° C. The cooling bath was removed and stirring was continued at RT for 1.5 h. The reaction was quenched with aq. $KHSO_4$ solution and extracted with EtOAc. The organic layer was washed with aq. $KHSO_4$ solution, sat. aq. $NaHCO_3$ solution and brine, dried over $MgSO_4$ and concentrated in vacuo. Purification by CC (KP-SIL™ from Biotage) using Hept/EtOAc (8/2 to 2/8) gives the desired product as white solid;

LC-MS (A): $t_R$=0.57 min; [M+H]+: 237.26.

A.2.1.4 Chiral separation of tBu-(2,3-dihydrofuro[2,3-b]pyridin-3-yl)carbamate tBu-(2,3-Dihydrofuro[2,3-b]pyridin-3-yl)carbamate was separated into the respective enantiomers using prep. chiral HPLC (Daicel, ChiralCel OJ-H, 5 μm, 20×250 mm; Hept/EtOH 60/40, flow 16 mL/min);

Chiral analytic HPLC (ChiralCel OJ-H, 5 μm, 250×4.6 mm ID, Hept/EtOH 60/40, flow 0.8 mL/min);
Enantiomer A: $t_R$=5.50 min;
Enantiomer B: $t_R$=6.81 min.

A.2.1.5 Synthesis of (R)-2,3-dihydrofuro[2,3-b]pyridin-3-amine and (S)-2,3-dihydrofuro[2,3-b]pyridin-3-amine The respective pure enantiomer of tBu-(2,3-dihydrofuro[2,3-b]pyridin-3-yl)carbamate (0.89 mmol) was suspended in 0.5 mL EtOAc and 0.5 mL THF before 0.56 mL HCl (4M solution in dioxane) was added. The mixture was stirred at RT overnight and then at 45° C. for 1 h. Evaporation to dryness gives the desired compound in form of the respective HCl salt as off-white solid.

LC-MS (C): $t_R$=0.19 min; [M+H]+: 137.15.
Chiral analytic HPLC (Chiralpak AY-H, 5 μm, 250×4.6 mm ID, Hept+0.05% DEA/EtOH+0.05% DEA 75/25, flow 0.8 mL/min);
Enantiomer A: $t_R$=9.68 min;
Enantiomer B: $t_R$=13.02 min.

A.2.2 Synthesis of 3,4-dihydro-2H-pyrano[2,3-b]pyridin-4-amine

A.2.2.1 Synthesis of 3,4-dihydro-2H-pyrano[2,3-b]pyridin-4-ol

A mixture of 1-(2-bromopyridin-3-yl)propane-1,3-diol (40.9 mmol) (Bioorg. Med. Chem. Lett., 20(9), 2938-2941, 2010) and tBuOK (123 mmol) in 164 mL tBuOH was stirred for 90 min at 80° C. The reaction mixture was then concentrated in vacuo, taken up in $H_2O$ and extracted with EtOAc and DCM. The combined organic layers were dried over $MgSO_4$ and concentrated in vacuo. Purification by CC (KP-SIL™ from Biotage) using DCM/MeOH (1-5%) gives the desired product as brown oil;

LC-MS (D): $t_R$=0.59 min; [M+H]+: 152.04.

A.2.2.2 Synthesis of 4-azido-3,4-dihydro-2H-pyrano[2,3-b]pyridine

To a mixture of 3,4-dihydro-2H-pyrano[2,3-b]pyridin-4-ol (3.31 mmol) in 16.5 mL toluene were added DPPA (4.96 mmol) followed by DBU (4.96 mmol) at 0° C. The cooling bath was removed after 2 h and the mixture was stirred at RT overnight. The reaction was quenched by adding sat. aq. $NaHCO_3$ solution and extracted with EtOAc. The combined organic layers were dried over $MgSO_4$ and concentrated in vacuo. Purification by CC (KP-SIL™ from Biotage) using Hept/EtOAc (4/1) to EtOAc gives the desired product as colorless oil;

LC-MS (A): $t_R$=0.39 min; [M+H]+: 177.29.

A.2.2.3 Synthesis of 3,4-dihydro-2H-pyrano[2,3-b]pyridin-4-amine

A mixture of 4-azido-3,4-dihydro-2H-pyrano[2,3-b]pyridine (3.0 mmol) and Pd/C (10 mol %) in 12 mL EtOH was stirred under a $H_2$ atmosphere. After 3 h, the mixture was filtered over a pad of Celite, washed with EtOH and concentrated in vacuo to obtain the title compound as colorless oil;

LC-MS (D): $t_R$=0.44 min; [M+H]+: 151.09.

A.2.3 Synthesis of 5,6-dihydrofuro[2,3-c]pyridazin-5-amine

A.2.3.1 Synthesis of 5-hydroxyfuro[2,3-c]pyridazine-6-carboxylic acid ethyl ester To a suspension of NaH (44.7 mmol) in 100 mL 1,2-dimethoxyethane was added ethyl glycolate (43 mmol) under ice cooling and stirring. The ice bath was removed and stirring was continued at RT. After 30 min, a solution of 3-chloropyridazine-4-carboxylic acid ethyl ester (17.2 mmol) in 40 mL 1,2-dimethoxyethane was slowly added and the mixture was heated to 75° C. for 2 h. The solvent was then evaporated off and the residual solid was redissolved in aq. $NaHCO_3$ solution and EtOAc. The aqueous layer was acidified with AcOH and extracted with DCM (3×). The combined organic layers were dried over MgSO$_4$ and concentrated in vacuo. Purification by CC (KP-SIL™ from Biotage) using EtOAc/MeOH (1/1) gives the desired product as brown solid;
LC-MS (C): t$_R$=0.57 min; [M+H]+: 209.22.

A.2.3.2 Synthesis of furo[2,3-c]pyridazin-5(6H)-one

To a solution of 5-hydroxyfuro[2,3-c]pyridazine-6-carboxylic acid ethyl ester (5.39 mmol) in 15 mL THF were added 25 mL of 1M NaOH solution. After stirring at RT overnight, 5 mL 25% HCl solution were carefully added. After stirring for 1 h, the mixture was concentrated in vacuo to give the desired product as black solid in form of the HCl salt;
LC-MS (C): t$_R$=0.37 min; [M+H]+: 137.06.

A.2.3.3 Synthesis of furo[2,3-c]pyridazin-5(6H)-one O-methyl oxime

To a solution of furo[2,3-c]pyridazin-5(6H)-one (4.81 mmol) in 30 mL EtOH were added O-methyl-hydroxylamine (9.62 mmol) and NaOAc (9.62 mmol). After heating to 30° C. for 4.5 h the reaction mixture was concentrated in vacuo to half of its volume. Water and DCM were added and the aqueous phase was extracted with DCM (3×). The combined organic layers were dried over MgSO$_4$ and concentrated in vacuo. Purification by CC (KP-SIL™ from Biotage) using Hept/EtOAc (1/1) gives the desired product as beige solid;
LC-MS (C): t$_R$=0.51 min; [M+H]+: 165.97.

A.2.3.4 Synthesis of 5,6-dihydrofuro[2,3-c]pyridazin-5-amine

To a solution of furo[2,3-c]pyridazin-5(6H)-one O-methyl oxime (1.35 mmol) in 10 mL 7N NH$_3$ in MeOH was added Pd/C (50 mg) and the reaction mixture was stirred under a H$_2$ atmosphere for 1 h. The mixture was then filtered over Celite, washed with 20 mL MeOH and concentrated in vacuo to give the title compound as dark red oil;
LC-MS (C): t$_R$=0.15 min; [M+H]+: 138.08.

A.2.4 Synthesis of 2,3-dihydrofuro[2,3-c]pyridin-3-amine

A.2.4.1 Synthesis of 3-chloroisonicotinic acid ethyl ester

A solution of 3-chloroisonicotinic acid (18.6 mmol) in 120 mL EtOH and 3 mL conc. H$_2$SO$_4$ was heated to reflux overnight. The mixture was concentrated in vacuo, redissolved in aq. NaHCO$_3$ solution and extracted with EtOAc (2×). The combined organic layers were dried over MgSO$_4$ and concentrated in vacuo to give the desired product as yellow oil;
LC-MS (A): t$_R$=0.63 min; [M+H]+: 186.08.

A.2.4.2 Synthesis of 3-hydroxyfuro[2,3-c]pyridine-2-carboxylic acid ethyl ester

This compound was prepared using a method analogous to that of 5-hydroxyfuro[2,3-c]pyridazine-6-carboxylic acid ethyl ester (A.2.3.1), 3-chloroisonicotinic acid ethyl ester replacing 3-chloropyridazine-4-carboxylic acid ethyl ester;
LC-MS (A): t$_R$=0.36 min; [M+H]+: 208.06.

A.2.4.3 Synthesis of furo[2,3-c]pyridin-3(2H)-one

A suspension of 3-hydroxyfuro[2,3-c]pyridine-2-carboxylic acid ethyl ester (10 mmol) in 10 mL 25% HCl solution and 5 mL H$_2$O was heated to reflux overnight. After cooling to RT, the reaction mixture was quenched with sat. aq. NaHCO$_3$ solution and extracted with EtOAc. The combined organic layers were dried over MgSO$_4$ and concentrated in vacuo to give the desired product as brown solid;
LC-MS (A): t$_R$=0.13 min; [M+H]+: 136.26.

A.2.4.4 Synthesis of furo[2,3-c]pyridin-3(2H)-one O-methyl oxime

This compound was prepared using a method analogous to that of furo[2,3-c]pyridazin-5(6H)-one O-methyl oxime (A.2.3.3), furo[2,3-c]pyridin-3(2H)-one replacing furo[2,3-c]pyridazin-5(6H)-one. Purification by CC (KP-SIL™ from Biotage) using Hept/EtOAc (1/1) gives the desired product as brown solid;
LC-MS (A): t$_R$=0.34 min; [M+H]+: 165.13.

A.2.4.5 Synthesis of 2,3-dihydrofuro[2,3-c]pyridin-3-amine

This compound was prepared using a method analogous to that of 2,3-dihydrofuro[2,3-b]pyridin-3-amine (A.2.1.2), furo[2,3-c]pyridin-3(2H)-one O-methyl oxime replacing furo[2,3-b]pyridin-3(2H)-one O-methyl oxime;
LC-MS (D): t$_R$=0.35 min; [M+H]+: 137.10.

A.2.5 Synthesis of 7-methyl-2,3-dihydrofuro[2,3-c]pyridin-3-amine

A.2.5.1 Synthesis of 2,3-dichloroisonicotinic acid ethyl ester

To a solution of 2,3-dichloroisonicotinic acid (5.62 mmol) in 15 mL DMF were added NaH (7.31 mmol) followed by iodoethane (6.75 mmol) at 0° C. The cooling bath was removed and the mixture was stirred at RT overnight. The reaction was quenched with sat. aq. NaHCO$_3$ solution and extracted with EtOAc. The combined organic layers were dried over MgSO$_4$ and concentrated in vacuo. Purification by CC (KP-SIL™ from Biotage) using Hept/EtOAc (6/4) gives the desired product as yellow oil;
LC-MS (A): t$_R$=0.78 min; [M+H]+: 219.95.

A.2.5.2 Synthesis of 3-chloro-2-methylisonicotinic acid ethyl ester

A mixture of 2,3-dichloroisonicotinic acid ethyl ester (3.15 mmol), K$_2$CO$_3$ (4.73 mmol) and trimethylboroxine (3.15 mmol) in 4 mL dioxane was degassed with Ar. Then, tetrakis (triphenylphosphine)palladium (0.31 mmol) was added and the mixture was heated to reflux overnight. At RT, the reaction mixture was poured into water and extracted with DCM. The combined organic layers were dried over K$_2$CO$_3$, filtered over a pad of celite and concentrated in vacuo. Purification by CC (KP-SIL™ from Biotage) using Hept/EtOAc (8/2) gives the desired product as brown oil;
LC-MS (A): t$_R$=0.67 min; [M+H]+: 200.03.

A.2.5.3 Synthesis of 3-hydroxy-7-methylfuro[2,3-c]pyridine-2-carboxylic acid ethyl ester This compound was prepared using a method analogous to that of 5-hydroxyfuro[2,3-c]pyridazine-6-carboxylic acid ethyl ester (A.2.3.1), 3-chloro-2-methylisonicotinic acid ethyl ester replacing 3-chloropyridazine-4-carboxylic acid ethyl ester. Purification by CC (KP-SIL™ from Biotage) using EtOAc/MeOH (8/2) gives the desired product as brown solid;

LC-MS (A): $t_R$=0.37 min; [M+H]+: 222.03.

A.2.5.4 Synthesis of 7-methylfuro[2,3-c]pyridin-3(2H)-one

This compound was prepared using a method analogous to that of furo[2,3-c]pyridin-3(2H)-one (A.2.4.3), 3-hydroxy-7-methylfuro[2,3-c]pyridine-2-carboxylic acid ethyl ester replacing 3-hydroxyfuro[2,3-c]pyridine-2-carboxylic acid ethyl ester;

LC-MS (A): $t_R$=0.21 min; [M+H]+: 150.25.

A.2.5.5 Synthesis of 7-methylfuro[2,3-c]pyridin-3(2H)-one O-methyl oxime

This compound was prepared using a method analogous to that of furo[2,3-c]pyridazin-5(6H)-one O-methyl oxime (A.2.3.3), 7-methylfuro[2,3-c]pyridin-3(2H)-one replacing furo[2,3-c]pyridazin-5(6H)-one;

LC-MS (A): $t_R$=0.35 min; [M+H]+: 179.14.

A.2.5.6 Synthesis of 7-methyl-2,3-dihydrofuro[2,3-c]pyridin-3-amine

This compound was prepared using a method analogous to that of 5,6-dihydrofuro[2,3-c]pyridazin-5-amine (A.2.3.4), 7-methylfuro[2,3-c]pyridin-3(2H)-one O-methyl oxime replacing furo[2,3-c]pyridazin-5(6H)-one O-methyl oxime;

LC-MS (A): $t_R$=0.11 min; [M+H]+: 151.29.

A.2.6 Synthesis of 7-cyclopropyl-2,3-dihydrofuro[2,3-c]pyridin-3-amine

A.2.6.1 Synthesis of 3-chloro-2-cyclopropylisonicotinic acid ethyl ester

This compound was prepared using a method analogous to that of 3-chloro-2-methylisonicotinic acid ethyl ester (A.2.5.2), cyclopropylboronic acid replacing trimethylboroxine. Purification by CC (KP-SIL™ from Biotage) using Hept/EtOAc (9/1) gives the desired product as colorless oil;

LC-MS (A): $t_R$=0.86 min; [M+H]+: 226.02.

A.2.6.2 Synthesis of 3-hydroxy-7-cyclopropylfuro[2,3-c]pyridine-2-carboxylic acid ethyl ester This compound was prepared using a method analogous to that of 5-hydroxyfuro[2,3-c]pyridazine-6-carboxylic acid ethyl ester (A.2.3.1), 3-chloro-2-cyclopropylisonicotinic acid ethyl ester replacing 3-chloropyridazine-4-carboxylic acid ethyl ester. Purification by CC (KP-SIL™ from Biotage) using Hept/EtOAc (7/3) gives the desired product as colorless oil;

LC-MS (A): $t_R$=0.48 min; [M+H]+: 248.00.

A.2.6.3 Synthesis of 7-cyclopropylfuro[2,3-c]pyridin-3(2H)-one

This compound was prepared using a method analogous to that of furo[2,3-c]pyridin-3(2H)-one (A.2.4.3), 3-hydroxy-7-cyclopropylfuro[2,3-c]pyridine-2-carboxylic acid ethyl ester replacing 3-hydroxyfuro[2,3-c]pyridine-2-carboxylic acid ethyl ester;

LC-MS (A): $t_R$=0.32 min; [M+H]+: 176.14.

A.2.6.4 Synthesis of 7-cyclopropylfuro[2,3-c]pyridin-3(2H)-one O-methyl oxime This compound was prepared using a method analogous to that of furo[2,3-c]pyridazin-5(6H)-one O-methyl oxime (A.2.3.3), 7-cyclopropylfuro[2,3-c]pyridin-3(2H)-one replacing furo[2,3-c]pyridazin-5(6H)-one. Purification by CC (KP-SIL™ from Biotage) using Hept/EtOAc (9/1) gives the desired product as brown oil;

LC-MS (A): $t_R$=0.51 min; [M+H]+: 205.41.

A.2.6.5 Synthesis of 7-cyclopropyl-2,3-dihydrofuro[2,3-c]pyridin-3-amine

This compound was prepared using a method analogous to that of 5,6-dihydrofuro[2,3-c]pyridazin-5-amine (A.2.3.4), 7-cyclopropylfuro[2,3-c]pyridin-3(2H)-one O-methyl oxime replacing furo[2,3-c]pyridazin-5(6H)-one O-methyl oxime;

LC-MS (A): $t_R$=0.15 min; [M+H]+: 177.47.

A.2.7 Synthesis of 7-chloro-2,3-dihydrofuro[2,3-c]pyridin-3-amine

A.2.7.1 Synthesis of 3-(methoxyimino)-2,3-dihydrofuro[2,3-c]pyridine 6-oxide To a solution of furo[2,3-c]pyridin-3(2H)-one O-methyl oxime (5.35 mmol) (A.2.4.4) in 15 mL DCM was added 3-chloroperbenzoic acid (16.0 mmol). The mixture was stirred at RT overnight, diluted with 20 mL DCM and extracted with sat. aq. NaHCO$_3$ solution (2×), with sat. aq. Na$_2$S$_2$O$_3$ solution (2×) and brine. The combined organic layers were dried over MgSO$_4$ and concentrated in vacuo to give the desired product as yellow solid;

LC-MS (A): $t_R$=0.34 min; [M+H]+: 181.13.

A.2.7.2 Synthesis of 7-chlorofuro[2,3-c]pyridin-3(2H)-one O-methyl oxime

To a solution of 3-(methoxyimino)-2,3-dihydrofuro[2,3-c]pyridine 6-oxide (5.35 mmol) in 30 mL DCM were added 2.9 mL phosphoryl chloride at 0° C. The mixture was heated to 50° C. for 7 h, concentrated in vacuo, redissolved in DCM and quenched with solid NaHCO$_3$ and then water. The aqueous layer was extracted with DCM (2×). The combined organic layers were dried over MgSO$_4$ and concentrated in vacuo. Purification by CC (KP-SIL™ from Biotage) using Hept/EtOAc (8/2) gives the desired product as beige solid;

LC-MS (A): $t_R$=0.67 min; [M+H]+: 199.36.

A.2.7.3 Synthesis of 7-chloro-2,3-dihydrofuro[2,3-c]pyridin-3-amine

To a solution of 7-chlorofuro[2,3-c]pyridin-3(2H)-one O-methyl oxime (0.045 mmol) in 1 mL THF were added 10 mL of a borane solution (1M solution in THF). The mixture was heated to 60° C. overnight in a closed vessel. At RT, the reaction mixture was quenched with sat. aq. NaHCO$_3$ solution and extracted with EtOAc (3×). The combined organic layers were dried over MgSO$_4$ and concentrated in vacuo to give the desired product as yellow oil;
LC-MS (A): t$_R$=0.44 min; [M+H]+: 171.09.

A.2.8 Synthesis of 7-methoxy-2,3-dihydrofuro[2,3-c]pyridin-3-amine

A.2.8.1 Synthesis of 7-methoxyfuro[2,3-c]pyridin-3(2H)-one O-methyl oxime

To a suspension of 7-chlorofuro[2,3-c]pyridin-3(2H)-one O-methyl oxime (1.01 mmol) (A.2.7.2) in 4 mL MeOH were added 0.56 mL of NaOMe (30% solution in MeOH). The mixture was heated to 90° C. for 12 h in a closed vessel and it was then concentrated in vacuo. Purification by CC (KP-SIL™ from Biotage) using Hept/EtOAc (9/1) gives the desired product as beige solid;
LC-MS (A): t$_R$=0.65 min; [M+H]+: 195.09.

A.2.8.2 Synthesis of 7-methoxy-2,3-dihydrofuro[2,3-c]pyridin-3-amine

This compound was prepared using a method analogous to that of 5,6-dihydrofuro[2,3-c]pyridazin-5-amine (A.2.3.4), 7-methoxyfuro[2,3-c]pyridin-3(2H)-one O-methyl oxime replacing furo[2,3-c]pyridazin-5(6H)-one O-methyl oxime;
LC-MS (A): t$_R$=0.22 min; [M+H]+: 167.19.

A.2.9 Synthesis of 5-chloro-2,3-dihydrofuro[2,3-c]pyridin-3-amine

A.2.9.1 Synthesis of 5-chloro-3-hydroxyfuro[2,3-c]pyridine-2-carboxylic acid ethyl ester This compound was prepared using a method analogous to that of 5-hydroxyfuro[2,3-c]pyridazine-6-carboxylic acid ethyl ester (A.2.3.1), 5-bromo-2-chloroisonicotinic acid ethyl ester replacing 3-chloropyridazine-4-carboxylic acid ethyl ester. Purification by CC (KP-SIL™ from Biotage) using EtOAc/MeOH (9/1) gives the desired product as brown solid;
LC-MS (C): t$_R$=0.75 min; [M+H]+: 241.92.

A.2.9.2 Synthesis of 5-chlorofuro[2,3-c]pyridin-3(2H)-one

This compound was prepared using a method analogous to that of furo[2,3-c]pyridin-3(2H)-one (A.2.4.3), 5-chloro-3-hydroxyfuro[2,3-c]pyridine-2-carboxylic acid ethyl ester replacing 3-hydroxyfuro[2,3-c]pyridine-2-carboxylic acid ethyl ester;
LC-MS (C): t$_R$=0.62 min; [M+H]+: 170.09.

A.2.9.2 Synthesis of 5-chlorofuro[2,3-c]pyridin-3(2H)-one O-methyl oxime

This compound was prepared using a method analogous to that of furo[2,3-c]pyridazin-5(6H)-one O-methyl oxime (A.2.3.3), 5-chlorofuro[2,3-c]pyridin-3(2H)-one replacing furo[2,3-c]pyridazin-5(6H)-one;
LC-MS (C): t$_R$=0.77 min; [M+H]+: 199.07.

A.2.9.3 Synthesis of 5-chloro-2,3-dihydrofuro[2,3-c]pyridin-3-amine

To a solution of 5-chlorofuro[2,3-c]pyridin-3(2H)-one O-methyl oxime (0.71 mmol) in 1 mL THF were added 2.2 mL of a borane solution (1M in THF). The mixture was heated to 40° C. for 1 h in a closed vessel. At RT, the reaction mixture was quenched with MeOH, the pH was adjusted to 9 with 1M NaOH solution and the mixture was extracted with EtOAc. The combined organic layers were dried over MgSO$_4$ and concentrated in vacuo to give the desired product as yellow oil;
LC-MS (C): t$_R$=0.56 min; [M+H]+: 171.11.

A.2.10 Synthesis of 5-methyl-2,3-dihydrofuro[2,3-c]pyridin-3-amine

A.2.10.1 Synthesis of 5-methylfuro[2,3-c]pyridin-3(2H)-one O-methyl oxime

This compound was prepared using a method analogous to that of 3-chloro-2-methylisonicotinic acid ethyl ester (A.2.5.2), 5-chlorofuro[2,3-c]pyridin-3(2H)-one O-methyl oxime replacing 2,3-dichloroisonicotinic acid ethyl ester. Purification by prep HPLC, xbridge very polar method acidic gives the desired product as brown solid;
LC-MS (C): t$_R$=0.45 min; [M+H]+: 179.20.

A.2.10.2 Synthesis of 5-methyl-2,3-dihydrofuro[2,3-c]pyridin-3-amine

This compound was prepared using a method analogous to that of 5,6-dihydrofuro[2,3-c]pyridazin-5-amine (A.2.3.4), 5-methylfuro[2,3-c]pyridin-3(2H)-one O-methyl oxime replacing furo[2,3-c]pyridazin-5(6H)-one O-methyl oxime;
LC-MS (D): t$_R$=0.47 min; [M+H]+: 151.07.

A.2.11 Synthesis of 4-methyl-2,3-dihydrofuro[2,3-c]pyridin-3-amine

A.2.11.1 Synthesis of 3,5-dichloroisonicotinic acid ethyl ester

To a suspension of 3,5-dichloroisonicotinic acid (52 mmol) in 250 mL DCM and 5 mL DMF were added 11.4 mL thionylchloride. The mixture was heated to 40° C. for 2.5 h, cooled to RT before 100 mL EtOH were added. The solution was stirred at RT for 10 min and then concentrated in vacuo. The crude mixture was taken up in EtOAc and quenched with sat. aq. NaHCO$_3$ solution under ice cooling. The aqueous layer was extracted with EtOAc (2×). The combined organic layers were washed with brine, dried over MgSO$_4$ and concentrated in vacuo. Purification by CC using Hept/EtOAc (95/5 to 85/15) gives the desired product as colorless oil;
LC-MS (C): t$_R$=0.84 min; [M+H]+: 220.05.

A.2.11.1 Synthesis of 4-chloro-3-hydroxyfuro[2,3-c]pyridine-2-carboxylic acid ethyl ester This compound was prepared using a method analogous to that of 5-hydroxyfuro[2,3-c]pyridazine-6-carboxylic acid ethyl ester (A.2.3.1), 3,5-chloroisonicotinic acid ethyl ester replacing 3-chloropyridazine-4-carboxylic acid ethyl ester;
LC-MS (C): t$_R$=0.79 min; [M+H]+: 241.90.

A.2.11.2 Synthesis of 4-chlorofuro[2,3-c]pyridin-3(2H)-one

This compound was prepared using a method analogous to that of furo[2,3-c]pyridin-3(2H)-one (A.2.4.3), 4-chloro-3- hydroxyfuro[2,3-c]pyridine-2-carboxylic acid ethyl ester replacing 3-hydroxyfuro[2,3-c]pyridine-2-carboxylic acid ethyl ester;
LC-MS (C): $t_R$=0.50 min; [M+H]+: 169.89.

A.2.11.3 Synthesis of 4-chlorofuro[2,3-c]pyridin-3(2H)-one O-methyl oxime

This compound was prepared using a method analogous to that of furo[2,3-c]pyridazin-5(6H)-one O-methyl oxime (A.2.3.3), 4-chlorofuro[2,3-c]pyridin-3(2H)-one replacing furo[2,3-c]pyridazin-5(6H)-one;
LC-MS (C): $t_R$=0.77 min; [M+H]+: 199.06.

A.2.11.4 Synthesis of 4-methylfuro[2,3-c]pyridin-3(2H)-one O-methyl oxime

This compound was prepared using a method analogous to that of 3-chloro-2-methylisonicotinic acid ethyl ester (A.2.5.2), 4-chlorofuro[2,3-c]pyridin-3(2H)-one O-methyl oxime replacing 2,3-dichloroisonicotinic acid ethyl ester. Purification by CC using Hept/EtOAc (9/1 to 1/1) gives a white solid;
LC-MS (C): $t_R$=0.52 min; [M+H]+: 179.20.

A.2.11.5 Synthesis of 4-methyl-2,3-dihydrofuro[2,3-c]pyridin-3-amine

This compound was prepared using a method analogous to that of 5,6-dihydrofuro[2,3-c]pyridazin-5-amine (A.2.3.4), 4-methylfuro[2,3-c]pyridin-3(2H)-one O-methyl oxime replacing furo[2,3-c]pyridazin-5(6H)-one O-methyl oxime;
LC-MS (C): $t_R$=0.15 min; [M+H]+: 151.32.

A.2.12 Synthesis of 4-cyclopropyl-2,3-dihydrofuro[2,3-c]pyridin-3-amine

A.2.12.1 Synthesis of 4-cyclopropylfuro[2,3-c]pyridin-3(2H)-one O-methyl oxime This compound was prepared using a method analogous to that of 4-methylfuro[2,3-c]pyridin-3(2H)-one O-methyl oxime (A.2.11.4), cyclopropylboronic acid replacing trimethylboroxine. Purification by CC using Hept/EtOAc (9/1 to 8/2) gives the desired product as white solid;
LC-MS (C): $t_R$=0.61 min; [M+H]+: 205.13.

A.2.12.2 Synthesis of 4-cyclopropyl-2,3-dihydrofuro[2,3-c]pyridin-3-amine

This compound was prepared using a method analogous to that of 5,6-dihydrofuro[2,3-c]pyridazin-5-amine (A.2.3.4), 4-cyclopropylfuro[2,3-c]pyridin-3(2H)-one O-methyl oxime replacing furo[2,3-c]pyridazin-5(6H)-one O-methyl oxime;
LC-MS (C): $t_R$=0.19 min; [M+H]+: 177.21.

A.2.13 Synthesis of 6-methyl-2,3-dihydrofuro[2,3-b]pyridin-3-amine

A.2.13.1 Synthesis of 2-chloro-6-methylnicotinic acid ethyl ester

A suspension of 2-chloro-6-methylnicotinic acid (7.23 mmol) and 1.2 mL of thionylchloride in 50 mL EtOH were heated to reflux overnight. The mixture was reduced to half of its volume, quenched with sat. aq. NaHCO$_3$ solution and extracted with DCM (2×). The combined organic layers were dried over MgSO$_4$ and concentrated in vacuo. Purification by (KP-SIL™ from Biotage) using Hept to Hept/EtOAc (1/1) gives the desired product as colorless oil;
LC-MS (C): $t_R$=0.76 min; [M+H]+: 200.25.

A.2.13.2 Synthesis of 3-hydroxy-6-methylfuro[2,3-b]pyridine-2-carboxylic acid ethyl ester This compound was prepared using a method analogous to that of 5-hydroxyfuro[2,3-c]pyridazine-6-carboxylic acid ethyl ester (A.2.3.1), 2-chloro-6-methylnicotinic acid ethyl ester replacing 3-chloropyridazine-4-carboxylic acid ethyl ester;
LC-MS (C): $t_R$=0.70 min; [M+H]+: 221.70.

A.2.13.3 Synthesis of 6-methylfuro[2,3-b]pyridin-3(2H)-one

This compound was prepared using a method analogous to that of furo[2,3-c]pyridin-3(2H)-one (A.2.4.3), 3-hydroxy-6-methylfuro[2,3-b]pyridine-2-carboxylic acid ethyl ester replacing 3-hydroxyfuro[2,3-c]pyridine-2-carboxylic acid ethyl ester;
LC-MS (C): $t_R$=0.51 min; [M+H]+: 150.14.

A.2.13.4 Synthesis of 6-methylfuro[2,3-b]pyridin-3(2H)-one O-methyl oxime

This compound was prepared using a method analogous to that of furo[2,3-c]pyridazin-5(6H)-one O-methyl oxime (A.2.3.3), 6-methylfuro[2,3-b]pyridin-3(2H)-one replacing furo[2,3-c]pyridazin-5(6H)-one. Purification by (KP-SIL™ from Biotage) using Hept to Hept/EtOAc (1/1) gives the desired product as white solid;
LC-MS (C): $t_R$=0.67 min; [M+H]+: 179.20.

A.2.13.5 Synthesis of 6-methyl-2,3-dihydrofuro[2,3-b]pyridin-3-amine

This compound was prepared using a method analogous to that of 5,6-dihydrofuro[2,3-c]pyridazin-5-amine (A.2.3.4), 6-methylfuro[2,3-b]pyridin-3(2H)-one O-methyl oxime replacing furo[2,3-c]pyridazin-5(6H)-one O-methyl oxime;
LC-MS (D): $t_R$=0.50 min; [M+H]+: 151.10.

A.2.14 Synthesis of 6-chloro-2,3-dihydrofuro[2,3-b]pyridin-3-amine

A.2.14.1 Synthesis of 3-hydroxy-6-chlorofuro[2,3-b]pyridine-2-carboxylic acid ethyl ester This compound was prepared using a method analogous to that of 5-hydroxyfuro[2,3-c]pyridazine-6-carboxylic acid ethyl ester (A.2.3.1), 2,6-dichloronicotinic acid methyl ester replacing 3-chloropyridazine-4-carboxylic acid ethyl ester;
LC-MS (C): $t_R$=0.77 min; [M+H]+: 241.97.

A.2.14.2 Synthesis of 6-chlorofuro[2,3-b]pyridin-3(2H)-one

This compound was prepared using a method analogous to that of furo[2,3-c]pyridin-3(2H)-one (A.2.4.3), 3-hydroxy-6- chlorofuro[2,3-b]pyridine-2-carboxylic acid ethyl ester replacing 3-hydroxyfuro[2,3-c]pyridine-2-carboxylic acid ethyl ester;

LC-MS (C): $t_R$=0.58 min; $^1$H NMR (CDCl$_3$) δ: 8.00 (d, 1H), 7.19 (d, 1H), 4.82 (s, 2H).

A.2.14.3 Synthesis of 6-chlorofuro[2,3-b]pyridin-3(2H)-one O-methyl oxime

This compound was prepared using a method analogous to that of furo[2,3-c]pyridazin-5(6H)-one O-methyl oxime (A.2.3.3), 6-chlorofuro[2,3-b]pyridin-3(2H)-one replacing furo[2,3-c]pyridazin-5(6H)-one;

LC-MS (C): $t_R$=0.76 min; [M+H]+: 199.05.

A.2.14.4 Synthesis of 6-chloro-2,3-dihydrofuro[2,3-b]pyridin-3-amine

This compound was prepared using a method analogous to that of 5-chloro-2,3-dihydrofuro[2,3-c]pyridin-3-amine (A.2.9.3), 6-chlorofuro[2,3-b]pyridin-3(2H)-one O-methyl oxime replacing 5-chlorofuro[2,3-c]pyridin-3(2H)-one O-methyl oxime;

LC-MS (D): $t_R$=0.50 min; [M+H]+: 170.96. $^1$H NMR (CDCl$_3$) δ: 7.60 (d, 1H), 6.93 (d, 1H), 4.80 (m, 1H), 4.68 (dd, 1H), 4.28 (dd, 1H).

A.2.15 Synthesis of 4-methyl-2,3-dihydrofuro[2,3-b]pyridin-3-amine

A.2.15.1 Synthesis of 3-hydroxy-4-methylfuro[2,3-b]pyridine-2-carboxylic acid ethyl ester This compound was prepared using a method analogous to that of 5-hydroxyfuro[2,3-c]pyridazine-6-carboxylic acid ethyl ester (A.2.3.1), 2-chloro-4-methylnicotinic acid ethyl ester replacing 3-chloropyridazine-4-carboxylic acid ethyl ester;

LC-MS (C): $t_R$=0.77 min; [M+H]+: 222.11.

A.2.15.2 Synthesis of 4-methylfuro[2,3-b]pyridin-3(2H)-one

This compound was prepared using a method analogous to that of furo[2,3-c]pyridin-3(2H)-one (A.2.4.3), 3-hydroxy-4-methylfuro[2,3-b]pyridine-2-carboxylic acid ethyl ester replacing 3-hydroxyfuro[2,3-c]pyridine-2-carboxylic acid ethyl ester;

LC-MS (C): $t_R$=0.54 min; [M+H]+: 150.20.

A.2.15.3 Synthesis of 4-methylfuro[2,3-b]pyridin-3(2H)-one O-methyl oxime

This compound was prepared using a method analogous to that of furo[2,3-c]pyridazin-5(6H)-one O-methyl oxime (A.2.3.3), 4-methylfuro[2,3-b]pyridin-3(2H)-one replacing furo[2,3-c]pyridazin-5(6H)-one;

LC-MS (C): $t_R$=0.74 min; [M+H]+: 179.20.

A.2.15.4 Synthesis of 4-methyl-2,3-dihydrofuro[2,3-b]pyridin-3-amine

This compound was prepared using a method analogous to that of 5,6-dihydrofuro[2,3-c]pyridazin-5-amine (A.2.3.4), 4-methylfuro[2,3-b]pyridin-3(2H)-one O-methyl oxime replacing furo[2,3-c]pyridazin-5(6H)-one O-methyl oxime;

LC-MS (C): $t_R$=0.24 min; [M+H]+: 151.06.

A.2.16 Synthesis of 4-methoxy-2,3-dihydrofuro[2,3-b]pyridin-3-amine

A.2.16.1 Synthesis of 4-bromo-2-chloronicotinic acid ethyl ester

To a solution of 4-bromo-2-chloropyridine (21.2 mmol) in 60 mL THF was added dropwise 11.7 mL of a solution of LDA (2M in THF) at −78° C. After stirring at −78° C. for 35 min, a solution of ethyl chloroformate (20.7 mmol) in 5 mL THF was added and the mixture was stirred at −78° C. for 2 h. The reaction was quenched with sat. aq. NaHCO$_3$ solution and extracted with EtOAc (3×). The combined organic layers were dried over MgSO$_4$ and concentrated in vacuo. Purification by (KP-SIL™ from Biotage) using Hept to Hept/EtOAc (8/2) gives the desired product as brown oil;

LC-MS (C): $t_R$=0.83 min; [M+H]+: 265.95.

A.2.16.2 Synthesis of 4-methoxy-2-chloronicotinic acid ethyl ester

To a solution of 4-bromo-2-chloronicotinic acid ethyl ester (5.06 mmol) in 15 mL MeOH was added 1.0 mL of a solution of NaOMe (30% in MeOH). The reaction mixture was stirred at 40° C. for 4 h, cooled to RT, diluted with EtOAc and then quenched with sat. aq. NH$_4$Cl solution. The organic layers was dried over MgSO$_4$ and concentrated in vacuo to give the desired compound as brown oil;

LC-MS (C): $t_R$=0.74 min; [M+H]+: 216.06.

A.2.16.3 Synthesis of 3-hydroxy-4-methoxyfuro[2,3-b]pyridine-2-carboxylic acid ethyl ester This compound was prepared using a method analogous to that of 5-hydroxyfuro[2,3-c]pyridazine-6-carboxylic acid ethyl ester (A.2.3.1), 4-methoxy-2-chloronicotinic acid ethyl ester replacing 3-chloropyridazine-4-carboxylic acid ethyl ester;

LC-MS (C): $t_R$=0.69 min; [M+H]+: 238.11.

A.2.16.4 Synthesis of 4-methoxyfuro[2,3-b]pyridin-3(2H)-one

This compound was prepared using a method analogous to that of furo[2,3-c]pyridin-3(2H)-one (A.2.4.3), 3-hydroxy-4-methoxyfuro[2,3-b]pyridine-2-carboxylic acid ethyl ester replacing 3-hydroxyfuro[2,3-c]pyridine-2-carboxylic acid ethyl ester;

LC-MS (C): $t_R$=0.47 min; [M+H]+: 166.13.

A.2.16.4 Synthesis of 4-methoxyfuro[2,3-b]pyridin-3(2H)-one O-methyl oxime

This compound was prepared using a method analogous to that of furo[2,3-c]pyridazin-5(6H)-one O-methyl oxime (A.2.3.3), 4-methoxyfuro[2,3-b]pyridin-3(2H)-one replacing furo[2,3-c]pyridazin-5(6H)-one. Purification by (KP-SIL™ from Biotage) using Hept/EtOAc (1/1) gives the desired product as white solid;

LC-MS (C): $t_R$=0.59 min; [M+H]+: 195.16.

A.2.16.5 Synthesis of 4-methoxy-2,3-dihydrofuro[2,3-b]pyridin-3-amine

This compound was prepared using a method analogous to that of 5,6-dihydrofuro[2,3-c]pyridazin-5-amine (A.2.3.4), 4-methoxyfuro[2,3-b]pyridin-3(2H)-one O-methyl oxime replacing furo[2,3-c]pyridazin-5(6H)-one O-methyl oxime;
LC-MS (C): $t_R$=0.24 min; [M+H]+: 166.99.

A.2.17 Synthesis of 4-ethoxy-6-methyl-2,3-dihydrofuro[2,3-b]pyridin-3-amine

A.2.17.1 Synthesis of 2-chloro-4-ethoxy-6-methylnicotinic acid ethyl ester

To a solution of 2,4-dichloro-6-methylnicotinic acid ethyl ester (2.49 mmol) in 6 mL EtOH was added NaOEt (2.61 mmol). The reaction mixture was heated to 60° C. overnight in a closed vessel. At RT, the mixture was diluted with EtOAc and washed with aq. NH$_4$Cl solution. The organic layer was dried over MgSO$_4$ and concentrated in vacuo. Purification by (KP-SIL™ from Biotage) using Hept/EtOAc (1/1) gives the desired product as beige solid;
LC-MS (C): $t_R$=0.83 min; [M+H]+: 244.13.

A.2.17.2 Synthesis of 3-hydroxy-4-ethoxy-6-methylfuro[2,3-b]pyridine-2-carboxylic acid ethyl ester This compound was prepared using a method analogous to that of 5-hydroxyfuro[2,3-c]pyridazine-6-carboxylic acid ethyl ester (A.2.3.1), 2-chloro-4-ethoxy-6-methylnicotinic acid ethyl ester replacing 3-chloropyridazine-4-carboxylic acid ethyl ester;
LC-MS (C): $t_R$=0.71 min; [M+H]+: 266.16.

A.2.17.3 Synthesis of 4-ethoxy-6-methylfuro[2,3-b]pyridin-3(2H)-one

This compound was prepared using a method analogous to that of furo[2,3-c]pyridin-3(2H)-one (A.2.4.3), 3-hydroxy-4-ethoxy-6-methylfuro[2,3-b]pyridine-2-carboxylic acid ethyl ester replacing 3-hydroxyfuro[2,3-c]pyridine-2-carboxylic acid ethyl ester;
LC-MS (C): $t_R$=0.58 min; [M+H]+: 194.28.

A.2.17.4 Synthesis of 4-ethoxy-6-methylfuro[2,3-b]pyridin-3(2H)-one O-methyl oxime This compound was prepared using a method analogous to that of furo[2,3-c]pyridazin-5(6H)-one O-methyl oxime (A.2.3.3), 4-ethoxy-6-methylfuro[2,3-b]pyridin-3(2H)-one replacing furo[2,3-c]pyridazin-5(6H)-one. Purification by (KP-SIL™ from Biotage) using Hept/EtOAc (1/1) gives the desired product as white solid;
LC-MS (C): $t_R$=0.68 min; [M+H]+: 223.23.

A.2.17.5 Synthesis of 4-ethoxy-6-methyl-2,3-dihydrofuro[2,3-b]pyridin-3-amine This compound was prepared using a method analogous to that of 5,6-dihydrofuro[2,3-c]pyridazin-5-amine (A.2.3.4), 4-ethoxy-6-methylfuro[2,3-b]pyridin-3(2H)-one O-methyl oxime replacing furo[2,3-c]pyridazin-5(6H)-one O-methyl oxime;
LC-MS (C): $t_R$=0.36 min; [M+H]+: 195.33.

A.2.18 Synthesis of 4-methoxy-6-methyl-2,3-dihydrofuro[2,3-b]pyridin-3-amine

A.2.18.1 Synthesis of 2-chloro-4-methoxy-6-methylnicotinic acid ethyl ester This compound was prepared using a method analogous to that of 2-chloro-4-ethoxy-6-methylnicotinic acid ethyl ester (A.2.17.1), NaOMe replacing NaOEt;
LC-MS (C): $t_R$=0.76 min; [M+H]+: 230.12.

A.2.18.2 Synthesis of 3-hydroxy-4-methoxy-6-methylfuro[2,3-b]pyridine-2-carboxylic acid ethyl ester This compound was prepared using a method analogous to that of 5-hydroxyfuro[2,3-c]pyridazine-6-carboxylic acid ethyl ester (A.2.3.1), 2-chloro-4-methoxy-6-methylnicotinic acid ethyl ester replacing 3-chloropyridazine-4-carboxylic acid ethyl ester;
LC-MS (C): $t_R$=0.72 min; [M+H]+: 252.10.

A.2.18.3 Synthesis of 4-methoxy-6-methylfuro[2,3-b]pyridin-3(2H)-one

This compound was prepared using a method analogous to that of furo[2,3-c]pyridin-3(2H)-one (A.2.4.3), 3-hydroxy-4-methoxy-6-methylfuro[2,3-b]pyridine-2-carboxylic acid ethyl ester replacing 3-hydroxyfuro[2,3-c]pyridine-2-carboxylic acid ethyl ester;
LC-MS (C): $t_R$=0.51 min; [M+H]+: 180.30.

A.2.18.4 Synthesis of 4-methoxy-6-methylfuro[2,3-b]pyridin-3(2H)-one O-methyl oxime This compound was prepared using a method analogous to that of furo[2,3-c]pyridazin-5(6H)-one O-methyl oxime (A.2.3.3), 4-methoxy-6-methylfuro[2,3-b]pyridin-3(2H)-one replacing furo[2,3-c]pyridazin-5(6H)-one. Purification by (KP-SIL™ from Biotage) using Hept/EtOAc (1/1) gives the desired product as white solid;
LC-MS (C): $t_R$=0.61 min; [M+H]+: 209.19.

A.2.18.5 Synthesis of 4-methoxy-6-methyl-2,3-dihydrofuro[2,3-b]pyridin-3-amine This compound was prepared using a method analogous to that of 5,6-dihydrofuro[2,3-c]pyridazin-5-amine (A.2.3.4), 4-methoxy-6-methylfuro[2,3-b]pyridin-3(2H)-one O-methyl oxime replacing furo[2,3-c]pyridazin-5(6H)-one O-methyl oxime;
LC-MS (C): $t_R$=0.21 min; [M+H]+: 181.33.

A.2.19 Synthesis of 4-(trifluoromethyl)-2,3-dihydrofuro[2,3-b]pyridin-3-amine

A.2.19.1 Synthesis of 3-hydroxy-4-(trifluoromethyl)furo[2,3-b]pyridine-2-carboxylic acid ethyl ester This compound was prepared using a method analogous to that of 5-hydroxyfuro[2,3-c]pyridazine-6-carboxylic acid ethyl ester (A.2.3.1), 2-chloro-4-(trifluoromethyl)nicotinic acid ethyl ester replacing 3-chloropyridazine-4-carboxylic acid ethyl ester;
LC-MS (C): $t_R$=0.86 min; [M+H]+: 276.09.

A.2.19.2 Synthesis of 4-(trifluoromethyl)furo[2,3-b]pyridin-3(2H)-one

This compound was prepared using a method analogous to that of furo[2,3-c]pyridin-3(2H)-one (A.2.4.3), 3-hydroxy-4-(trifluoromethyl)furo[2,3-b]pyridine-2-carboxylic acid ethyl ester replacing 3-hydroxyfuro[2,3-c]pyridine-2-carboxylic acid ethyl ester;

LC-MS (C): $t_R$=0.66 min; [M+H]+: 203.95.

A.2.19.3 Synthesis of 4-(trifluoromethyl)furo[2,3-b]pyridin-3(2H)-one O-methyl oxime This compound was prepared using a method analogous to that of furo[2,3-c]pyridazin-5(6H)-one O-methyl oxime (A.2.3.3), 4-(trifluoromethyl)furo[2,3-b]pyridin-3(2H)-one replacing furo[2,3-c]pyridazin-5(6H)-one. Purification by (KP-SIL™ from Biotage) using Hept/EtOAc (9/1) gives the desired product as colorless foam;

LC-MS (C): $t_R$=0.84 min; [M+H]+: 233.07.

A.2.19.4 Synthesis of 4-(trifluoromethyl)-2,3-dihydrofuro[2,3-b]pyridin-3-amine This compound was prepared using a method analogous to that of 5,6-dihydrofuro[2,3-c]pyridazin-5-amine (A.2.3.4), 4-(trifluoromethyl)furo[2,3-b]pyridin-3(2H)-one O-methyl oxime replacing furo[2,3-c]pyridazin-5(6H)-one O-methyl oxime;

LC-MS (D): $t_R$=0.59 min; [M+H]+: 205.23.

B. Preparation of Examples

B.1 Synthesis of Compounds of Formula (Ia) (General Procedure)

To a solution of the respective acid (0.975 mmol) in 8 mL DCM were added 0.25 mL DIPEA, HOBT (1.27 mmol) and EDC.HCl (1.27 mmol) followed by the addition of a solution of the respective amine (1.46 mmol), dissolved in 2 mL DCM. The mixture was stirred at RT overnight and then diluted with DCM and extracted with saturated aq NaHCO$_3$ solution and water. The organic layer was dried over MgSO$_4$, concentrated in vacuo and the crude was purified by purification methods listed beforehand to give the desired amides.

B.2 Synthesis of rac-2-(2,4-dichloro-6-(hydroxymethyl)phenyl)-N-(2,3-dihydrofuro[2,3-b]pyridin-3-yl)acetamide A mixture of rac-3,5-dichloro-2-(2-((2,3-dihydrofuro[2,3-b]pyridin-3-yl)amino)-2-oxoethyl)benzyl acetate (0.097 mmol) in 0.5 mL THF and 0.24 mL of 2M NaOH solution was stirred at 30° C. for 3 h. The reaction mixture was diluted with EtOAc and washed with water and brine. The organic layer was dried over MgSO$_4$ and concentrated in vacuo to give the desired compound as white solid.

B.3 Synthesis of Compounds of Formula (Ib) and (Ic) (General Procedure)

To a solution of a compound of formula (Ia) (0.08 mmol) in 1 mL DCM was added 3-chloroperbenzoic acid (0.25 mmol). The mixture was stirred at RT overnight, diluted with DCM and extracted with sat. aq. NaHCO$_3$ solution, with sat. aq. Na$_2$S$_2$O$_3$ solution and brine. The organic layer was dried over MgSO$_4$, concentrated in vacuo and the crude was purified by purification methods listed beforehand to give the desired N-oxides.

B.4 Chiral Separation of Compounds of Formula (I)

Example 1 was separated into the respective enantiomers using prep. chiral HPLC (Daicel, ChiralPak AY-H, 5 μm, 20×250 mm; Hept/EtOH 80/20, flow 16 mL/min), detection: UV 210 nm;

Chiral analytic HPLC (ChiralPak AY-H, 5 μm, 250×4.6 mm ID, Hept/EtOH 80/20, flow 0.8 mL/min), detection: UV 210 nm;

Enantiomer A: $t_R$=10.53 min (example 3);
Enantiomer B: $t_R$=14.33 min (example 4).

Example 5 was separated into the respective enantiomers using prep. chiral HPLC (Daicel, ChiralPak AD-H, 5 μm, 30×250 mm; Hept/EtOH 0.1% DEA 75/25, flow 34 mL/min), detection: UV 283 nm;

Chiral analytic HPLC (ChiralPak AD-H, 5 μm, 250×4.6 mm ID, Hept 0.05% DEA/EtOH 0.05% DEA 75/25, flow 0.8 mL/min), detection: UV 210 nm;

Enantiomer A: $t_R$=8.93 min (example 6);
Enantiomer B: $t_R$=11.43 min (example 7).

Example 8 was separated into the respective enantiomers using prep. chiral HPLC (Daicel, ChiralPak AD-H, 5 μm, 30×250 mm; Hept/EtOH 0.1% DEA 75/25, flow 34 mL/min), detection: UV 210 nm;

Chiral analytic HPLC (ChiralPak AD-H, 5 μm, 250×4.6 mm ID, Hept 0.05% DEA/EtOH 0.05% DEA 75/25, flow 0.8 mL/min), detection: UV 210 nm;

Enantiomer A: $t_R$=11.61 min (example 28);
Enantiomer B: $t_R$=13.97 min (example 29).

Example 9 was separated into the respective enantiomers using prep. chiral HPLC (Daicel, ChiralPak IA, 5 μm, 20×250 mm; Hept/EtOH+0.1% DEA 70/30, flow 16 mL/min), detection: UV 210 nm;

Chiral analytic HPLC (ChiralPak IA, 5 μm, 250×4.6 mm ID, Hept+0.05% DEA/EtOH+0.05% DEA 70/30, flow 0.8 mL/min), detection: UV 210 nm;

Enantiomer A: $t_R$=8.00 min (example 30);
Enantiomer B: $t_R$=10.42 min (example 31).

Example 34 was separated into the respective enantiomers using prep. chiral HPLC (Daicel, ChiralPak AY-H, 5 μm, 20×250 mm; Hept/EtOH 50/50, flow 16 mL/min), detection: UV 210 nm;

Chiral analytic HPLC (ChiralPak AY-H, 5 μm, 250×4.6 mm ID, Hept/EtOH 50/50, flow 0.8 mL/min), detection: UV 210 nm;

Enantiomer A: $t_R$=4.59 min (example 73);
Enantiomer B: $t_R$=6.53 min (example 74).

Example 85, consisting of 4 stereoisomers was separated into the respective isomers using prep. chiral HPLC (Daicel, ChiralPak AD-H, 5 μm, 20×250 mm; Hept/EtOH 85/15+0.1% DEA, flow 16 mL/min), detection: UV 210 nm;

Chiral analytic HPLC (ChiralPak AD-H, 5 μm, 250×4.6 mm ID, Hept+0.05% DEA/EtOH+0.05% DEA 85/15, flow 0.8 mL/min), detection: UV 210 nm;

Isomer A: $t_R$=9.50 min (example 92);
Isomer B: $t_R$=11.58 min (example 93);
Isomer C: $t_R$=13.03 min (example 94);
Isomer D: $t_R$=14.85 min (example 95).

Example 89 was separated into the respective enantiomers using prep. chiral HPLC (Daicel, ChiralPak AD-H, 5 μm, 20×250 mm; Hept/EtOH 40/60, flow 16 mL/min), detection: UV 210 nm;

Chiral analytic HPLC (ChiralPak AD-H, 5 μm, 250×4.6 mm ID, Hept/EtOH 40/60, flow 0.8 mL/min), detection: UV 210 nm;

Enantiomer A: $t_R$=5.31 min (example 101);
Enantiomer B: $t_R$=6.74 min (example 102);

Example 91, consisting of 4 stereoisomers was separated into the respective isomers using prep. chiral HPLC (Daicel, ChiralPak AD-H, 5 μm, 4.6×250 mm; Hept/EtOH 95/5, flow 0.8 mL/min), detection: UV 210 nm;

Chiral analytic HPLC (ChiralPak AD-H, 5 μm, 250×4.6 mm ID, Hept+0.05% DEA/EtOH+0.05% DEA 95/5, flow 0.8 mL/min), detection: UV 210 nm;

Isomer A: $t_R$=18.15 min (example 118);
Isomer B: $t_R$=19.57 min (example 120);
Isomer C: $t_R$=25.86 min (example 122);
Isomer D: $t_R$=45.48 min (example 124).

Example 126, an epimeric mixture synthesized from enantiomer A of A.2.1.5, was separated into the respective isomers using prep. chiral HPLC ((R,R) Whelk-O1, 5 μm, 21×250 mm; Hept/EtOH 10/90, flow 16 mL/min), detection: UV 282 nm;

Chiral analytic HPLC ((R,R) Whelk-O1, 5 μm, 250×4.6 mm ID, Hept/EtOH 10/90, flow 0.8 mL/min), detection: UV 210 nm;

Isomer A: $t_R$=5.34 min (example 119);
Isomer B: $t_R$=7.54 min (example 125);

Example 127, an epimeric mixture synthesized from enantiomer B of A.2.1.5, was separated into the respective isomers using prep. chiral HPLC ((R,R) Whelk-O1, 5 μm, 21×250 mm; Hept/EtOH 10/90, flow 16 mL/min), detection: UV 282 nm;

Chiral analytic HPLC ((R,R) Whelk-O1, 5 μm, 250×4.6 mm ID, Hept/EtOH 10/90, flow 0.8 mL/min), detection: UV 210 nm;

Isomer A: $t_R$=5.14 min (example 121);
Isomer B: $t_R$=7.51 min (example 123);

Example 130, consisting of 4 stereoisomers was separated into the respective isomers using prep. chiral HPLC (Daicel, ChiralPak AD-H, 5 μm, 20×250 mm; Hept/EtOH 60/40, flow 16 mL/min), detection: UV 210 nm;

Chiral analytic HPLC (ChiralPak AD-H, 5 μm, 250×4.6 mm ID, Hept/EtOH 90/10, flow 0.8 mL/min), detection: UV 210 nm;

Isomer A: $t_R$=25.53 min (example 146);
Isomer B: $t_R$=38.66 min;
Isomer C: $t_R$=43.84 min;
Isomer D: $t_R$=55.02 min (example 147).

| Compound | Name | Purification method | LC-MS | $t_R$ [min] | $[M + H]^+$ |
|---|---|---|---|---|---|
| Example 1 | rac-2-(2,4-Dichloro-phenyl)-N-(2,3-dihydro-furo[2,3-b]pyridin-3-yl)-acetamide | G (EtOAc) | E | 0.82 | 323.2 |
| Example 2 | rac-2-(2-Chloro-4-fluoro-phenyl)-N-(2,3-dihydro-furo[2,3-b]pyridin-3-yl)-acetamide | G (EtOAc) | E | 0.74 | 307.2 |
| Example 3 | 2-(2,4-Dichloro-phenyl)-N-(2,3-dihydro-furo[2,3-b]pyridin-3-yl)-acetamide (enantiomer A of example 1) | see B.4 | E | 0.82 | 323.1 |
| Example 4 | 2-(2,4-Dichloro-phenyl)-N-(2,3-dihydro-furo[2,3-b]pyridin-3-yl)-acetamide (enantiomer B of example 1) | see B.4 | E | 0.82 | 323.1 |
| Example 5 | rac-2-(2,4-Dichloro-6-methyl-phenyl)-N-(2,3-dihydro-furo[2,3-b]pyridin-3-yl)-acetamide | N | E | 0.89 | 337.2 |
| Example 6 | 2-(2,4-Dichloro-6-methyl-phenyl)-N-(2,3-dihydro-furo[2,3-b]pyridin-3-yl)-acetamide (enantiomer A of example 5) | see B.4 | E | 0.89 | 337.2 |
| Example 7 | 2-(2,4-Dichloro-6-methyl-phenyl)-N-(2,3-dihydro-furo[2,3-b]pyridin-3-yl)-acetamide (enantiomer B of example 5) | see B.4 | E | 0.89 | 337.2 |
| Example 8 | rac-2-(2,4-Dichloro-6-methyl-phenyl)-N-(3,4-dihydro-2H-pyrano[2,3-b]pyridin-4-yl)-acetamide | P | E | 0.86 | 351.2 |
| Example 9 | rac-2-(2,4-Dichloro-phenyl)-N-(3,4-dihydro-2H-pyrano[2,3-b]pyridin-4-yl)-acetamide | P | E | 0.79 | 337.2 |
| Example 10 | rac-2-(2-Cyano-phenyl)-N-(2,3-dihydro-furo[2,3-b]pyridin-3-yl)-acetamide | I | E | 0.59 | 280.2 |
| Example 11 | rac-N-(2,3-Dihydro-furo[2,3-b]pyridin-3-yl)-2-o-tolyl-acetamide | I | E | 0.7 | 269.2 |
| Example 12 | rac-N-(2,3-Dihydro-furo[2,3-b]pyridin-3-yl)-2-(2-methoxy-phenyl)-acetamide | H | E | 0.66 | 285.2 |
| Example 13 | rac-2-(4-Cyano-phenyl)-N-(2,3-dihydro-furo[2,3-b]pyridin-3-yl)-acetamide | I | E | 0.59 | 280.2 |
| Example 14 | rac-N-(2,3-Dihydro-furo[2,3-b]pyridin-3-yl)-2-p-tolyl-acetamide | H | E | 0.72 | 269.2 |
| Example 15 | rac-2-(4-Chloro-phenyl)-N-(2,3-dihydro-furo[2,3-b]pyridin-3-yl)-acetamide | H | E | 0.75 | 289.2 |
| Example 16 | rac-N-(2,3-Dihydro-furo[2,3-b]pyridin-3-yl)-2-(4-trifluoromethyl-phenyl)-acetamide | H | E | 0.81 | 323.2 |

-continued

| Compound | Name | Purification method | LC-MS | $t_R$ [min] | [M + H]⁺ |
|---|---|---|---|---|---|
| Example 17 | rac-2-(2,4-Difluoro-phenyl)-N-(2,3-dihydro-furo[2,3-b]pyridin-3-yl)-acetamide | H | E | 0.68 | 291.2 |
| Example 18 | rac-N-(2,3-Dihydro-furo[2,3-b]pyridin-3-yl)-2-(4-fluoro-2-trifluoromethyl-phenyl)-acetamide | H | E | 0.80 | 341.2 |
| Example 19 | rac-N-(2,3-Dihydro-furo[2,3-b]pyridin-3-yl)-2-(2,4-dimethoxy-phenyl)-acetamide | H | E | 0.67 | 315.2 |
| Example 20 | rac-N-(2,3-Dihydro-furo[2,3-b]pyridin-3-yl)-2-(2-fluoro-4-methoxy-phenyl)-acetamide | H | E | 0.67 | 303.2 |
| Example 21 | rac-2-(3,4-Dichloro-phenyl)-N-(2,3-dihydro-furo[2,3-b]pyridin-3-yl)-acetamide | I | E | 0.84 | 323.1 |
| Example 22 | rac-N-(2,3-Dihydro-furo[2,3-b]pyridin-3-yl)-2-(2,4,6-trifluoro-phenyl)-acetamide | H | E | 0.7 | 309.2 |
| Example 23 | 2-(4-Chloro-phenyl)-N-(2,3-dihydro-furo[2,3-b]pyridin-3-yl)-propionamide | I | E | 0.83 | 303.2 |
| Example 24 | rac-1-(2,4-Dichloro-phenyl)-cyclopropanecarboxylic acid (2,3-dihydro-furo[2,3-b]pyridin-3-yl)-amide | H | E | 0.93 | 349.2 |
| Example 25 | rac-1-(2-Chloro-4-fluoro-phenyl)-cyclopentanecarboxylic acid (2,3-dihydro-furo[2,3-b]pyridin-3-yl)-amide | H | E | 0.94 | 361.2 |
| Example 26 | rac-2-(4-Chloro-phenyl)-N-(2,3-dihydro-furo[2,3-b]pyridin-3-yl)-isobutyramide | H | E | 0.89 | 317.2 |
| Example 27 | rac-3-(2,4-Dichloro-phenyl)-N-(2,3-dihydro-furo[2,3-b]pyridin-3-yl)-propionamide | I | E | 0.89 | 337.2 |
| Example 28 | 2-(2,4-Dichloro-6-methyl-phenyl)-N-(3,4-dihydro-2H-pyrano[2,3-b]pyridin-4-yl)-acetamide (enantiomer A of example 8) | see B.4 | E | 0.86 | 351.2 |
| Example 29 | 2-(2,4-Dichloro-6-methyl-phenyl)-N-(3,4-dihydro-2H-pyrano[2,3-b]pyridin-4-yl)-acetamide (enantiomer B of example 8) | see B.4 | E | 0.86 | 351.2 |
| Example 30 | 2-(2,4-Dichloro-phenyl)-N-(3,4-dihydro-2H-pyrano[2,3-b]pyridin-4-yl)-acetamide (enantiomer A of example 9) | see B.4 | E | 0.79 | 337.2 |
| Example 31 | 2-(2,4-Dichloro-phenyl)-N-(3,4-dihydro-2H-pyrano[2,3-b]pyridin-4-yl)-acetamide (enantiomer B of example 9) | see B.4 | E | 0.79 | 337.2 |
| Example 32 | rac-2-(2,4-Dichloro-6-ethyl-phenyl)-N-(2,3-dihydro-furo[2,3-b]pyridin-3-yl)-acetamide | L | E | 0.95 | 351.2 |
| Example 33 | rac-2-(2,4-Dichloro-6-trifluoromethyl-phenyl)-N-(2,3-dihydro-furo[2,3-b]pyridin-3-yl)-acetamide | G (DCM/5% MeOH) | E | 0.94 | 391.1 |
| Example 34 | rac-2-(2-Chloro-3-trifluoromethyl-phenyl)-N-(2,3-dihydro-furo[2,3-b]pyridin-3-yl)-acetamide | N | E | 0.84 | 357.2 |
| Example 35 | rac-2-(4-Chloro-2-trifluoromethyl-phenyl)-N-(2,3-dihydro-furo[2,3-b]pyridin-3-yl)-acetamide | L | E | 0.88 | 357.2 |
| Example 36 | rac-N-(2,3-Dihydro-furo[2,3-b]pyridin-3-yl)-2-(4-phenoxy-phenyl)-acetamide | L | E | 0.89 | 347.3 |
| Example 37 | rac-2-(2,4-Dichloro-6-cyano-phenyl)-N-(2,3-dihydro-furo[2,3-b]pyridin-3-yl)-acetamide | G 3:4 Hept/EtOAc | E | 0.79 | 348.1 |
| Example 38 | rac-2-(2-Chloro-4-fluoro-phenyl)-N-(3,4-dihydro-2H-pyrano[2,3-b]pyridin-4-yl)-acetamide | M | E | 0.71 | 321.2 |
| Example 39 | rac-2-(2,4-Dichloro-6-cyclopropyl-phenyl)-N-(2,3-dihydro-furo[2,3-b]pyridin-3-yl)-acetamide | L | E | 0.98 | 363.2 |
| Example 40 | rac-2-(4-Chloro-2-fluoro-3-methyl-6-trifluoromethyl-phenyl)-N-(2,3-dihydro-furo[2,3-b]pyridin-3-yl)-acetamide | L | E | 0.97 | 389.2 |

-continued

| Compound | Name | Purification method | LC-MS | t_R [min] | [M + H]+ |
|---|---|---|---|---|---|
| Example 41 | rac-2-(2,4-Dichloro-5-fluoro-phenyl)-N-(2,3-dihydro-furo[2,3-b]pyridin-3-yl)-acetamide | L | E | 0.85 | 341.2 |
| Example 42 | rac-2-(2-Chloro-6-fluoro-3-methyl-phenyl)-N-(2,3-dihydro-furo[2,3-b]pyridin-3-yl)-acetamide | L | E | 0.81 | 321.2 |
| Example 43 | rac-2-(5-Chloro-2-trifluoromethyl-phenyl)-N-(2,3-dihydro-furo[2,3-b]pyridin-3-yl)-acetamide | L | E | 0.87 | 357.2 |
| Example 44 | rac-2-(2-Chloro-phenyl)-N-(3,4-dihydro-2H-pyrano[2,3-b]pyridin-4-yl)-acetamide | M | E | 0.67 | 303.2 |
| Example 45 | rac-2-(4-Cyano-phenyl)-N-(3,4-dihydro-2H-pyrano[2,3-b]pyridin-4-yl)-acetamide | M | E | 0.55 | 294.3 |
| Example 46 | rac-N-(3,4-Dihydro-2H-pyrano[2,3-b]pyridin-4-yl)-2-(4-trifluoromethyl-phenyl)-acetamide | M | E | 0.79 | 337.0 |
| Example 47 | rac-N-(3,4-Dihydro-2H-pyrano[2,3-b]pyridin-4-yl)-2-(3-trifluoromethyl-phenyl)-acetamide | M | E | 0.78 | 337.0 |
| Example 48 | rac-N-(3,4-Dihydro-2H-pyrano[2,3-b]pyridin-4-yl)-2-(4-phenoxy-phenyl)-acetamide | M | E | 0.87 | 361.3 |
| Example 49 | rac-2-(2-Chloro-3-trifluoromethyl-phenyl)-N-(3,4-dihydro-2H-pyrano[2,3-b]pyridin-4-yl)-acetamide | M | E | 0.82 | 371.3 |
| Example 50 | rac-2-(2-Chloro-6-fluoro-phenyl)-N-(3,4-dihydro-2H-pyrano[2,3-b]pyridin-4-yl)-acetamide | M | E | 0.68 | 321.2 |
| Example 51 | rac-2-(2,4-Difluoro-phenyl)-N-(3,4-dihydro-2H-pyrano[2,3-b]pyridin-4-yl)-acetamide | M | E | 0.65 | 305.2 |
| Example 52 | rac-N-(3,4-Dihydro-2H-pyrano[2,3-b]pyridin-4-yl)-2-(4-fluoro-2-trifluoromethyl-phenyl)-acetamide | M | E | 0.78 | 355.0 |
| Example 53 | rac-2-(4-Chloro-2-trifluoromethyl-phenyl)-N-(3,4-dihydro-2H-pyrano[2,3-b]pyridin-4-yl)-acetamide | M | E | 0.86 | 371.2 |
| Example 54 | rac-2-(2,3-Dichloro-phenyl)-N-(3,4-dihydro-2H-pyrano[2,3-b]pyridin-4-yl)-acetamide | M | E | 0.77 | 337.2 |
| Example 55 | rac-2-(3,4-Dichloro-phenyl)-N-(3,4-dihydro-2H-pyrano[2,3-b]pyridin-4-yl)-acetamide | M | E | 0.82 | 337.2 |
| Example 56 | rac-2-(2,4-Dichloro-6-trifluoromethyl-phenyl)-N-(3,4-dihydro-2H-pyrano[2,3-b]pyridin-4-yl)-acetamide | M | E | 0.92 | 405.2 |
| Example 57 | rac-2-(2,4-Dichloro-5-fluoro-phenyl)-N-(3,4-dihydro-2H-pyrano[2,3-b]pyridin-4-yl)-acetamide | M | E | 0.82 | 355.2 |
| Example 58 | rac-1-(2,4-Dichloro-phenyl)-cyclopropanecarboxylic acid (3,4-dihydro-2H-pyrano[2,3-b]pyridin-4-yl)-amide | M | E | 0.91 | 363.2 |
| Example 59 | rac-1-(2-Chloro-4-fluoro-phenyl)-cyclopentanecarboxylic acid (3,4-dihydro-2H-pyrano[2,3-b]pyridin-4-yl)-amide | M | E | 0.93 | 375.3 |
| Example 60 | rac-2-(2-Chloro-pyridin-3-yl)-N-(3,4-dihydro-2H-pyrano[2,3-b]pyridin-4-yl)-acetamide | M | E | 0.46 | 304.2 |
| Example 61 | rac-N-(3,4-Dihydro-2H-pyrano[2,3-b]pyridin-4-yl)-2-(2,6-dimethyl-pyridin-3-yloxy)-acetamide | M | E | 0.31 | 314.3 |
| Example 62 | rac-N-(3,4-Dihydro-2H-pyrano[2,3-b]pyridin-4-yl)-2-(3-methyl-isoxazol-5-yl)-acetamide | M | E | 0.43 | 274.2 |
| Example 63 | rac-N-(3,4-Dihydro-2H-pyrano[2,3-b]pyridin-4-yl)-2-(5-methyl-pyrazol-1-yl)-acetamide | M | E | 0.43 | 273.2 |
| Example 64 | 2-(4-Chloro-phenyl)-N-(3,4-dihydro-2H-pyrano[2,3-b]pyridin-4-yl)-propionamide | M | E | 0.8 | 317.2 |

-continued

| Compound | Name | Purification method | LC-MS | t_R [min] | [M + H]+ |
|---|---|---|---|---|---|
| Example 65 | rac-3-(2,4-Dichloro-phenyl)-N-(3,4-dihydro-2H-pyrano[2,3-b]pyridin-4-yl)-propionamide | M | E | 0.86 | 351.2 |
| Example 66 | rac-2-(2,3-Dichloro-phenyl)-N-(2,3-dihydro-furo[2,3-b]pyridin-3-yl)-acetamide | G (DCM/5% MeOH) | E | 0.8 | 323.1 |
| Example 67 | rac-2-(2,3-Dichloro-6-fluoro-phenyl)-N-(2,3-dihydro-furo[2,3-b]pyridin-3-yl)-acetamide | G (DCM/5% MeOH) | E | 0.81 | 341.1 |
| Example 68 | rac-N-(2,3-Dihydro-furo[2,3-b]pyridin-3-yl)-2-(2-fluoro-6-trifluoromethyl-phenyl)-acetamide | L | E | 0.78 | 341.2 |
| Example 69 | rac-N-(2,3-Dihydro-furo[2,3-b]pyridin-3-yl)-2-(3-fluoro-4-trifluoromethoxy-phenyl)-acetamide | L | E | 0.88 | 357.2 |
| Example 70 | rac-2-(2,4-Dichloro-6-fluoro-phenyl)-N-(3,4-dihydro-2H-pyrano[2,3-b]pyridin-4-yl)-acetamide | P | E | 0.82 | 355.2 |
| Example 71 | rac-2-(2,3-Dichloro-6-trifluoromethyl-phenyl)-N-(2,3-dihydro-furo[2,3-b]pyridin-3-yl)-acetamide | G (3:4 Hept/EtOAc) | E | 0.91 | 391.2 |
| Example 72 | rac-2-(2,6-Dichloro-3-trifluoromethyl-phenyl)-N-(2,3-dihydro-furo[2,3-b]pyridin-3-yl)-acetamide | G (3:4 Hept/EtOAc) | E | 0.91 | 391.2 |
| Example 73 | 2-(2-Chloro-3-trifluoromethyl-phenyl)-N-(2,3-dihydro-furo[2,3-b]pyridin-3-yl)-acetamide (enantiomer A of example 34) | see B.4 | E | 0.85 | 357.2 |
| Example 74 | 2-(2-Chloro-3-trifluoromethyl-phenyl)-N-(2,3-dihydro-furo[2,3-b]pyridin-3-yl)-acetamide (enantiomer B of example 34) | see B.4 | E | 0.85 | 357.2 |
| Example 75 | rac-2-(2-Chloro-3-cyano-phenyl)-N-(2,3-dihydro-furo[2,3-b]pyridin-3-yl)-acetamide | G (EtOAc) | E | 0.65 | 314.2 |
| Example 76 | rac-2-(2,4-Dichloro-6-fluoro-phenyl)-N-(2,3-dihydro-furo[2,3-b]pyridin-3-yl)-acetamide | G (3:4 Hept/EtOAc) | E | 0.85 | 341.2 |
| Example 77 | rac-2-(3,6-Dichloro-2-fluoro-phenyl)-N-(2,3-dihydro-furo[2,3-b]pyridin-3-yl)-acetamide | G (3:4 Hept/EtOAc) | E | 0.82 | 341.2 |
| Example 78 | rac-2-(2-Chloro-3,6-difluoro-phenyl)-N-(2,3-dihydro-furo[2,3-b]pyridin-3-yl)-acetamide | G (3:4 Hept/EtOAc) | E | 0.73 | 325.2 |
| Example 79 | 2-(2,4-Dichloro-phenyl)-N-2,3-dihydro-furo[2,3-b]pyridin-3-yl-3-hydroxy-propionamide (mixture of 4 stereoisomers) | G (DCM/10% MeOH) | E | 0.76 | 353.2 |
| Example 80 | rac-2-Chloro-3-[(2,3-dihydro-furo[2,3-b]pyridin-3-ylcarbamoyl)-methyl]-benzamide | G (DCM/10% MeOH) | E | 0.42 | 332.2 |
| Example 81 | 2-(2,4-Dichloro-phenyl)-N-2,3-dihydro-furo[2,3-b]pyridin-3-yl-3-pyrrolidin-1-yl-propionamide (mixture of 4 stereoisomers) | G (DCM/10% MeOH) | F | 0.62 | 406.3 |
| Example 82 | rac-N-(2,3-Dihydro-furo[2,3-b]pyridin-3-yl)-4-(4-fluoro-phenyl)-butyramide | G (1:1 Hept/EtOAc) | E | 0.79 | 301.3 |
| Example 83 | rac-2-(2,4-Dichloro-phenyl)-N-(2,3-dihydro-furo[2,3-c]pyridin-3-yl)-acetamide | M | E | 0.63 | 323.2 |
| Example 84 | 2-(2,4-Dichloro-phenyl)-N-2,3-dihydro-furo[2,3-b]pyridin-3-yl-butyramide (mixture of 4 stereoisomers) | G (1:1 Hept/EtOAc) | E | 1 | 351.2 |
| Example 85 | 2-(2,4-Dichloro-phenyl)-N-2,3-dihydro-furo[2,3-b]pyridin-3-yl-propionamide (mixture of 4 stereoisomers) | G (1:1 Hept/EtOAc) | E | 0.91 | 337.2 |
| Example 86 | 2-(2,4-Dichloro-phenyl)-2-trideuteromethyl-N-2,3-dihydro-furo[2,3-b]pyridin-3-yl-acetamide (mixture of 4 stereoisomers) | G (1:1 Hept/EtOAc) | E | 0.91 | 340.2 |
| Example 87 | rac-2-(2-Chloro-3-trifluoromethyl-phenyl)-N-(2,3-dihydro-furo[2,3-c]pyridin-3-yl)-acetamide | G (EtOAc) | E | 0.66 | 357.2 |

-continued

| Compound | Name | Purification method | LC-MS | $t_R$ [min] | $[M + H]^+$ |
|---|---|---|---|---|---|
| Example 88 | rac-2-(2-Chloro-4-trifluoromethyl-phenyl)-N-(2,3-dihydro-furo[2,3-b]pyridin-3-yl)-acetamide | G (3:4 Hept/EtOAc) | E | 0.88 | 357.2 |
| Example 89 | rac-2-(2,4-Dichloro-6-methyl-phenyl)-N-(2,3-dihydro-furo[2,3-c]pyridin-3-yl)-acetamide | G (EtOAc) | E | 0.7 | 337.2 |
| Example 90 | rac-N-(2,3-Dihydro-furo[2,3-b]pyridin-3-yl)-2-(2-fluoro-3-trifluoromethyl-phenyl)-acetamide | G (1:3 Hept/EtOAc) | E | 0.82 | 341.2 |
| Example 91 | 2-(2-Chloro-3-trifluoromethyl-phenyl)-N-2,3-dihydro-furo[2,3-b]pyridin-3-yl-propionamide (mixture of 4 stereoisomers) | G (1:2 Hept/EtOAc) | E | 0.93 | 371.2 |
| Example 92 | 2-(2,4-Dichloro-phenyl)-N-2,3-dihydro-furo[2,3-b]pyridin-3-yl-propionamide (isomer A of example 85) | see B.4 | E | 0.91 | 337.2 |
| Example 93 | 2-(2,4-Dichloro-phenyl)-N-2,3-dihydro-furo[2,3-b]pyridin-3-yl-propionamide (isomer B of example 85) | see B.4 | E | 0.91 | 337.2 |
| Example 94 | 2-(2,4-Dichloro-phenyl)-N-2,3-dihydro-furo[2,3-b]pyridin-3-yl-propionamide (isomer C of example 85) | see B.4 | E | 0.91 | 337.2 |
| Example 95 | 2-(2,4-Dichloro-phenyl)-N-2,3-dihydro-furo[2,3-b]pyridin-3-yl-propionamide (isomer D of example 85) | see B.4 | E | 0.91 | 337.2 |
| Example 96 | rac-2-(2-Chloro-4-cyano-phenyl)-N-(2,3-dihydro-furo[2,3-b]pyridin-3-yl)-acetamide | G (EtOAc) | E | 0.66 | 314.2 |
| Example 97 | rac-2-(3-Chloro-2-trifluoromethyl-phenyl)-N-(2,3-dihydro-furo[2,3-b]pyridin-3-yl)-acetamide | L | E | 0.84 | 357.2 |
| Example 98 | 2-(2-Chloro-3-cyano-phenyl)-N-2,3-dihydro-furo[2,3-b]pyridin-3-yl-acetamide (synthesized from enantiomer A of A.2.1.5) | G (EtOAc) | E | 0.64 | 314.2 |
| Example 99 | 2-(2-Chloro-3-cyano-phenyl)-N-2,3-dihydro-furo[2,3-b]pyridin-3-yl-acetamide (synthesized from enantiomer B of A.2.1.5) | G (EtOAc) | E | 0.64 | 314.2 |
| Example 100 | rac-2-(2,4-Dichloro-phenyl)-N-(7-methyl-2,3-dihydro-furo[2,3-c]pyridin-3-yl)-acetamide | M | E | 0.6 | 337.2 |
| Example 101 | 2-(2,4-Dichloro-6-methyl-phenyl)-N-2,3-dihydro-furo[2,3-c]pyridin-3-yl-acetamide (enantiomer A of example 89) | see B.4 | E | 0.7 | 337.2 |
| Example 102 | 2-(2,4-Dichloro-6-methyl-phenyl)-N-2,3-dihydro-furo[2,3-c]pyridin-3-yl-acetamide (enantiomer B of example 89) | see B.4 | E | 0.7 | 337.2 |
| Example 103 | rac-2-(2,4-Dichloro-6-hydroxymethyl-phenyl)-N-(2,3-dihydro-furo[2,3-b]pyridin-3-yl)-acetamide | none | E | 0.73 | 353.2 |
| Example 104 | rac-N-(7-Cyclopropyl-2,3-dihydro-furo[2,3-c]pyridin-3-yl)-2-(2,4-dichloro-phenyl)-acetamide | G (8:2 Hept/EtOAc) | E | 0.77 | 363.2 |
| Example 105 | rac-2-(2,4-Dichloro-phenyl)-N-(7-methoxy-2,3-dihydro-furo[2,3-c]pyridin-3-yl)-acetamide | G (8:2 Hept/EtOAc) | E | 0.92 | 353.2 |
| Example 106 | rac-N-(7-Chloro-2,3-dihydro-furo[2,3-c]pyridin-3-yl)-2-(2,4-dichloro-phenyl)-acetamide | K | E | 0.94 | 357.2 |
| Example 107 | rac-2-(2-Chloro-3-cyano-4-fluoro-phenyl)-N-(2,3-dihydro-furo[2,3-b]pyridin-3-yl)-acetamide | G (DCM/10% MeOH) | E | 0.7 | 332.2 |
| Example 108 | rac-2-(2-Chloro-3-trifluoromethoxy-phenyl)-N-(2,3-dihydro-furo[2,3-b]pyridin-3-yl)-acetamide | G (DCM/5% MeOH) | E | 0.89 | 373.2 |
| Example 109 | rac-2-(2-Chloro-3-trifluoromethyl-phenyl)-N-(5,6-dihydro-furo[2,3-c]pyridazin-5-yl)-acetamide | G (9:1 EtOAc/MeOH) | E | 0.74 | 358.2 |
| Example 110 | rac-2-(2,4-Dichloro-6-methyl-phenyl)-N-(5,6-dihydro-furo[2,3-c]pyridazin-5-yl)-acetamide | G (EtOAc) | E | 0.78 | 338.2 |

-continued

| Compound | Name | Purification method | LC-MS | $t_R$ [min] | $[M + H]^+$ |
|---|---|---|---|---|---|
| Example 111 | rac-2-(3-Acetyl-2-chloro-phenyl)-N-(2,3-dihydro-furo[2,3-b]pyridin-3-yl)-acetamide | G (EtOAc) | E | 0.63 | 331.2 |
| Example 112 | rac-2-(2,4-Dichloro-3-cyano-phenyl)-N-(2,3-dihydro-furo[2,3-b]pyridin-3-yl)-acetamide | G (DCM/MeOH) | E | 0.76 | 348.2 |
| Example 113 | rac-2-(3-Cyano-2-trifluoromethyl-phenyl)-N-(2,3-dihydro-furo[2,3-b]pyridin-3-yl)-acetamide | G (EtOAc) | E | 0.7 | 348.2 |
| Example 114 | rac-2-(2-Chloro-3-difluoromethyl-phenyl)-N-(2,3-dihydro-furo[2,3-b]pyridin-3-yl)-acetamide | G (EtOAc) | E | 0.77 | 339.2 |
| Example 115 | rac-N-(5-Chloro-2,3-dihydro-furo[2,3-c]pyridin-3-yl)-2-(2-chloro-3-trifluoromethyl-phenyl)-acetamide | L | E | 0.96 | 391.2 |
| Example 116 | rac-N-(5-Chloro-2,3-dihydro-furo[2,3-c]pyridin-3-yl)-2-(2,4-dichloro-phenyl)-acetamide | L | E | 0.95 | 357.2 |
| Example 117 | rac-2-(2-Chloro-3-trifluoromethyl-phenyl)-N-(5-methyl-2,3-dihydro-furo[2,3-c]pyridin-3-yl)-acetamide | M | E | 0.62 | 371.2 |
| Example 118 | 2-(2-Chloro-3-trifluoromethyl-phenyl)-N-2,3-dihydro-furo[2,3-b]pyridin-3-yl-propionamide (isomer A of example 91) | see B.4 | E | 0.93 | 371.2 |
| Example 119 | 2-(2-Chloro-3-trifluoromethyl-phenyl)-2-trideuteromethyl-N-2,3-dihydro-furo[2,3-b]pyridin-3-yl-acetamide (isomer A of example 126) | see B.4 | E | 0.92 | 374.3 |
| Example 120 | 2-(2-Chloro-3-trifluoromethyl-phenyl)-N-2,3-dihydro-furo[2,3-b]pyridin-3-yl-propionamide (isomer B of example 91) | see B.4 | E | 0.93 | 371.2 |
| Example 121 | 2-(2-Chloro-3-trifluoromethyl-phenyl)-2-trideuteromethyl-N-2,3-dihydro-furo[2,3-b]pyridin-3-yl-acetamide (isomer A of example 127) | see B.4 | E | 0.92 | 374.3 |
| Example 122 | 2-(2-Chloro-3-trifluoromethyl-phenyl)-N-2,3-dihydro-furo[2,3-b]pyridin-3-yl-propionamide (isomer C of example 91) | see B.4 | E | 0.93 | 371.2 |
| Example 123 | 2-(2-Chloro-3-trifluoromethyl-phenyl)-2-trideuteromethyl-N-2,3-dihydro-furo[2,3-b]pyridin-3-yl-acetamide (isomer B of example 127) | see B.4 | E | 0.92 | 374.3 |
| Example 124 | 2-(2-Chloro-3-trifluoromethyl-phenyl)-N-2,3-dihydro-furo[2,3-b]pyridin-3-yl-propionamide (isomer D of example 91) | see B.4 | E | 0.93 | 371.2 |
| Example 125 | 2-(2-Chloro-3-trifluoromethyl-phenyl)-2-trideuteromethyl-N-2,3-dihydro-furo[2,3-b]pyridin-3-yl-acetamide (isomer B of example 126) | see B.4 | E | 0.92 | 374.3 |
| Example 126 | 2-(2-Chloro-3-trifluoromethyl-phenyl)-2-trideuteromethyl-N-2,3-dihydro-furo[2,3-b]pyridin-3-yl-acetamide (epimeric mixture synthesized from enantiomer A of A.2.1.5) | G (1:1 Hept/EtOAc) | E | 0.92 | 374.2 |
| Example 127 | 2-(2-Chloro-3-trifluoromethyl-phenyl)-2-trideuteromethyl-N-2,3-dihydro-furo[2,3-b]pyridin-3-yl-acetamide (epimeric mixture synthesized from enantiomer B of A.2.1.5) | G (1:1 Hept/EtOAc) | E | 0.92 | 374.2 |
| Example 128 | rac-2-(2-Chloro-3-trifluoromethyl-phenyl)-N-(4-methyl-2,3-dihydro-furo[2,3-c]pyridin-3-yl)-acetamide | M | E | 0.71 | 371.3 |
| Example 129 | rac-2-(2-Chloro-3-trifluoromethyl-phenyl)-N-(7-oxy-2,3-dihydro-furo[2,3-b]pyridin-3-yl)-acetamide | P | E | 0.68 | 373.2 |
| Example 130 | 5,7-dichloro-N-(2,3-dihydrofuro[2,3-b]pyridin-3-yl)-2,3-dihydro-1H-indene-1-carboxamide (mixture of 4 stereoisomers) | L | E | 0.89 | 349.2 |

-continued

| Compound | Name | Purification method | LC-MS | $t_R$ [min] | $[M + H]^+$ |
|---|---|---|---|---|---|
| Example 131 | rac-2-(2,4-Dichloro-6-methyl-phenyl)-N-(4-methyl-2,3-dihydro-furo[2,3-c]pyridin-3-yl)-acetamide | M | E | 0.7 | 351.2 |
| Example 132 | rac-2-(2-Chloro-3-trifluoromethyl-phenyl)-N-(4-cyclopropyl-2,3-dihydro-furo[2,3-c]pyridin-3-yl)-acetamide | M | E | 0.73 | 397.2 |
| Example 133 | rac-2-(2,4-Dichloro-6-methyl-phenyl)-N-(6-methyl-2,3-dihydro-furo[2,3-b]pyridin-3-yl)-acetamide | G (EtOAc) | E | 0.94 | 351.2 |
| Example 134 | rac-2-(2-Chloro-3-trifluoromethyl-phenyl)-N-(6-methyl-2,3-dihydro-furo[2,3-b]pyridin-3-yl)-acetamide | G (EtOAc) | E | 0.89 | 371.2 |
| Example 135 | rac-2-(2-Chloro-3-trifluoromethyl-phenyl)-N-(4-methoxy-6-methyl-2,3-dihydro-furo[2,3-b]pyridin-3-yl)-acetamide | G (EtOAc) | E | 0.82 | 401.2 |
| Example 136 | rac-2-(2-Chloro-3-trifluoromethyl-phenyl)-N-(4-ethoxy-6-methyl-2,3-dihydro-furo[2,3-b]pyridin-3-yl)-acetamide | G (EtOAc) | E | 0.88 | 415.3 |
| Example 137 | rac-2-(2-Chloro-3-trifluoromethyl-phenyl)-N-(4-methyl-2,3-dihydro-furo[2,3-b]pyridin-3-yl)-acetamide | L | E | 0.88 | 371.2 |
| Example 138 | rac-2-(2,4-Dichloro-6-methyl-phenyl)-N-(4-methyl-2,3-dihydro-furo[2,3-b]pyridin-3-yl)-acetamide | L | E | 0.93 | 351.2 |
| Example 139 | rac-2-(2-Chloro-3-trifluoromethyl-phenyl)-N-(4-methoxy-2,3-dihydro-furo[2,3-b]pyridin-3-yl)-acetamide | L | E | 0.82 | 387.2 |
| Example 140 | rac-2-(2,4-Dichloro-phenoxy)-N-(2,3-dihydro-furo[2,3-b]pyridin-3-yl)-acetamide | M | E | 0.88 | 339.2 |
| Example 141 | rac-2-(3,4-Dichloro-phenoxy)-N-(2,3-dihydro-furo[2,3-b]pyridin-3-yl)-acetamide | M | E | 0.88 | 339.2 |
| Example 142 | rac-N-(2,3-Dihydro-furo[2,3-b]pyridin-3-yl)-2-(2,4-dimethyl-phenoxy)-acetamide | M | E | 0.86 | 299.3 |
| Example 143 | rac-N-(6-Chloro-2,3-dihydro-furo[2,3-b]pyridin-3-yl)-2-(2-chloro-3-trifluoromethyl-phenyl)-acetamide | L | E | 1.04 | 391.2 |
| Example 144 | rac-N-(6-Chloro-2,3-dihydro-furo[2,3-b]pyridin-3-yl)-2-(2,4-dichloro-6-methyl-phenyl)-acetamide | L | E | 1.09 | 371.2 |
| Example 145 | 5-chloro-N-(2,3-dihydrofuro[2,3-b]pyridin-3-yl)-2,3-dihydro-1H-indene-1-carboxamide (mixture of 4 stereoisomers) | G (1:1 Hept/EtOAc) | E | 0.9 | 315.3 |
| Example 146 | 5,7-dichloro-N-(2,3-dihydrofuro[2,3-b]pyridin-3-yl)-2,3-dihydro-1H-indene-1-carboxamide (isomer A of example 130) | see B.4 | E | 0.95 | 349.2 |
| Example 147 | 5,7-dichloro-N-(2,3-dihydrofuro[2,3-b]pyridin-3-yl)-2,3-dihydro-1H-indene-1-carboxamide (isomer D of example 130) | see B.4 | E | 0.96 | 349.2 |
| Example 148 | rac-2-(2-Chloro-3-trifluoromethyl-phenyl)-N-(6-oxy-2,3-dihydro-furo[2,3-c]pyridin-3-yl)-acetamide | L | E | 0.75 | 373.2 |
| Example 149 | 5-chloro-N-(2,3-dihydrofuro[2,3-b]pyridin-3-yl)-2,3-dihydro-1H-indene-2-carboxamide (epimeric mixture synthesized from enantiomer A of A.2.1.5) | G (EtOAc) | E | 0.92 | 315.3 |
| Example 150 | 5-chloro-N-(2,3-dihydrofuro[2,3-b]pyridin-3-yl)-2,3-dihydro-1H-indene-2-carboxamide (epimeric mixture synthesized from enantiomer B of A.2.1.5) | G (EtOAc) | E | 0.92 | 315.3 |
| Example 151 | rac-2-(2,4-Dichloro-6-methyl-phenyl)-N-(4-trifluoromethyl-2,3-dihydro-furo[2,3-b]pyridin-3-yl)-acetamide | L | E | 1.1 | 405.3 |

-continued

| Compound | Name | Purification method | LC-MS | | |
|---|---|---|---|---|---|
| | | | LC-MS | $t_R$ [min] | $[M+H]^+$ |
| Example 152 | rac-2-(2-Chloro-3-trifluoromethyl-phenyl)-N-(4-trifluoromethyl-2,3-dihydro-furo[2,3-b]pyridin-3-yl)-acetamide | J | E | 1.04 | 425.3 |

II. Biological Assays
In Vitro Assay

The P2X$_7$ receptor antagonistic activity of the compounds of formula (I) is determined in accordance with the following experimental method.

Experimental Method:
Cell Line Generation and YO-PRO Assay

Cell line generation was performed in general according to established molecular cloning protocols. Specifically, RNA was extracted from human whole blood using the Qiagen RNeasy kit (Qiagen, CH) according to the manufacturer's instructions. Subsequently cDNA was made (Superscript II, Invitrogen AG, CH) and the human P2X7 gene (genbank ref. BC011913) was amplified with the following primers: ATCGCGGCCGCTCAGTAAGGACTCTTGAAGCCACT and CGCCGCTAGCACCACCATGCCGGCCT-GCTGCAGCTGCA. The amplified sequence was subsequently ligated into a pcDNA3.1 (+) NotI, NheI digested plasmid. Human embryonic kidney (HEK) cells (ATCC CRL-1573, Manassas, Va., USA) were transfected with the pcDNA3.1 (+).hP2X7 plasmid using lipofectamine 2000 (Invitrogen AG, CH) according to the manufacturer's instructions. Following a 24 h exposure to DNA, cells were trypsinized and re-seeded at low density in the presence of 250 µg Geneticin. Geneticin resistant cells were then selected during two consecutive rounds of cloning by serial limiting dilution with visual inspection. Individual clones were screened for P2X7 expression by applying ATP and recording the resultant uptake of YO-PRO1. Specific cell clones were chosen based on RNA and protein expression. HEK cells stably expressing P2X7 were used to screen drugs using the YO-PRO1 assay. Cells were grown to confluency in adherent culture at 37° C. in a humidified 5% $CO_2$ incubator (split 1/5 every 3-4 days with DMEM, 10% FCS, 1% Penicillin/Streptomycin, 250 µg/ml Geneticin). Adherent cells were detached by incubation with Trypsine (1 ml per 165 cm$^2$ dish) for 2 minutes, then washed off with 10 ml PBS (without $Mg^{2+}$ and $Ca^{2+}$), and resuspended in DMEM, 10% FCS, 1% Penicillin/Streptomycin, no Geneticin. 10,000 cells per well (48 hours before the assay) or 25,000 cells per well (Vi-cell XR (Beckman Coulter) (24 hours before the assay) in 50 µl full medium were seeded on 384-well black-wall, clear bottom plates, that were coated before with 10 µl per well Poly-L-Lysine, incubated for 30-60 minutes at 37° C. and washed once with PBS. Medium was removed from cells and 50 µl of assay buffer containing 0.5 µM YO-PRO-1 was added into the wells. Solutions of antagonist compounds were prepared by serial dilutions of a 10 mM DMSO solution of the antagonist into PBS using a BioMek (Beckman Coulter). Each concentration was performed in duplicate. For IC$_{50}$ measurements 10 concentration points were measured (10 µM being the highest concentration followed by 9 serial dilution steps 1/3). The cells were incubated with the antagonists of the present invention together with ATP at a final concentration of 250 µM for 90 minutes. During this time period, four time points were taken. Each time point comprised the average of several measurements made within a few seconds. Fluorescence was measured in the FLIPR tetra (Molecular Devices) using the filters appropriate for YO-PRO-1 fluorescence (excitation 485/20, emission 530/25). The FLIPR tetra was equipped with Molecular Devices Screen Works system control software to define and run experimental protocols. For antagonist activity measurements, the maximal intensity was expressed as a percentage of that induced by the EC$_{50}$ value for agonist activation (0.25 mM ATP for HEK-293 cells expressing human recombinant P2X7 receptor). For IC50 measurements the maximum intensity is plotted against the concentration of compound to determine IC50 values.

Antagonistic activities with respect to the P2X$_7$ receptor (IC$_{50}$ values) of exemplified compounds are displayed in Table 1.

TABLE 1

| Compound | IC$_{50}$ [nM] | Compound | IC$_{50}$ [nM] | Compound | IC$_{50}$ [nM] |
|---|---|---|---|---|---|
| Example 1 | 33 | Example 2 | 103 | Example 3 | 42 |
| Example 4 | 40 | Example 5 | 12 | Example 6 | 16 |
| Example 7 | 3.5 | Example 8 | 43 | Example 9 | 144 |
| Example 10 | 2975 | Example 11 | 1310 | Example 12 | >5995 |
| Example 13 | >5417 | Example 14 | >5433 | Example 15 | 1415 |
| Example 16 | 1170 | Example 17 | 522 | Example 18 | 393 |
| Example 19 | >6660 | Example 20 | 578 | Example 21 | 473 |
| Example 22 | 884 | Example 23 | 828 | Example 24 | 133 |
| Example 25 | 151 | Example 26 | 2775 | Example 27 | 3460 |
| Example 28 | 29 | Example 29 | 172 | Example 30 | 177 |
| Example 31 | 184 | Example 32 | 23 | Example 33 | 242 |
| Example 34 | 7.4 | Example 35 | 193 | Example 36 | 1485 |
| Example 37 | 324 | Example 38 | 496 | Example 39 | 54 |
| Example 40 | 1580 | Example 41 | 332 | Example 42 | 641 |
| Example 43 | 8045 | Example 44 | 2005 | Example 45 | >6465 |
| Example 46 | 1353 | Example 47 | 1375 | Example 48 | 3305 |
| Example 49 | 17 | Example 50 | 2630 | Example 51 | 1695 |
| Example 52 | 1870 | Example 53 | 1315 | Example 54 | 67 |
| Example 55 | 1265 | Example 56 | 489 | Example 57 | 1465 |
| Example 58 | 294 | Example 59 | 390 | Example 60 | 780 |
| Example 61 | 814 | Example 62 | 2080 | Example 63 | >5720 |
| Example 64 | 1515 | Example 65 | 3015 | Example 66 | 20 |
| Example 67 | 210 | Example 68 | 1835 | Example 69 | 2445 |
| Example 70 | 386 | Example 71 | 3225 | Example 72 | 1015 |
| Example 73 | 9.9 | Example 74 | 4.7 | Example 75 | 22 |
| Example 76 | 90 | Example 77 | 2480 | Example 78 | 665 |
| Example 79 | 21 | Example 80 | 1241 | Example 81 | 1968 |
| Example 82 | 2027 | Example 83 | 15 | Example 84 | 55 |
| Example 85 | 15 | Example 86 | 33 | Example 87 | 4.6 |
| Example 88 | 72 | Example 89 | 3.2 | Example 90 | 92 |
| Example 91 | 42 | Example 92 | 9.0 | Example 93 | 137 |
| Example 94 | 11 | Example 95 | 104 | Example 96 | 123 |
| Example 97 | 15 | Example 98 | 29 | Example 99 | 40 |
| Example 100 | 52 | Example 101 | 598 | Example 102 | 2.2 |
| Example 103 | 16 | Example 104 | 71 | Example 105 | 248 |
| Example 106 | 52 | Example 107 | 31 | Example 108 | 71 |
| Example 109 | 9.0 | Example 110 | 6.7 | Example 111 | 416 |
| Example 112 | 219 | Example 113 | 28 | Example 114 | 7.6 |
| Example 115 | 81 | Example 116 | 350 | Example 117 | 63 |
| Example 118 | 24 | Example 119 | 156 | Example 120 | 50 |
| Example 121 | 432 | Example 122 | 571 | Example 123 | 23 |

TABLE 1-continued

| Compound | IC$_{50}$ [nM] | Compound | IC$_{50}$ [nM] | Compound | IC$_{50}$ [nM] |
|---|---|---|---|---|---|
| Example 124 | 308 | Example 125 | 41 | Example 126 | 45 |
| Example 127 | 52 | Example 128 | 5.6 | Example 129 | 123 |
| Example 130 | 137 | Example 131 | 14 | Example 132 | 506 |
| Example 133 | 43 | Example 134 | 21 | Example 135 | >4779 |
| Example 136 | >10000 | Example 137 | 37 | Example 138 | 99 |
| Example 139 | 272 | Example 140 | >8410 | Example 141 | >8630 |
| Example 142 | >9955 | Example 143 | 65 | Example 144 | 50 |
| Example 145 | 2325 | Example 146 | 160 | Example 147 | 40 |
| Example 148 | 165 | Example 149 | 4693 | Example 150 | 5373 |
| Example 151 | 6693 | Example 152 | 861 | | |

The invention claimed is:

1. A compound of the formula (I), wherein
n represents 1 or 2;
one of X and Y represents —N— or —N(O)— and the other one represents —N— or —C($R^6$)—;
$R^1$ represents hydrogen or methyl and $R^2$ represents hydrogen, ($C_1$-$C_2$)alkyl, ($C_1$-$C_2$)deuteroalkyl, hydroxy-methyl or heterocyclyl-methyl; or
$R^1$ and $R^2$ form, together with the carbon atom to which they are attached, a saturated carbocyclic ring of 3 to 6 members; and $R^3$ represents an aryl, an aryloxy, an aryl-($C_1$-$C_2$)alkyl, a heteroaryl or a heteroaryloxy group wherein the aromatic moiety of the groups is independently mono-, di-, tri- or tetra-substituted, wherein the substituents are independently selected from the group consisting of ($C_1$-$C_3$)alkyl, ($C_3$-$C_6$)cycloalkyl, ($C_1$-$C_3$)alkoxy, hydroxy-($C_1$-$C_2$)alkyl, ($C_1$-$C_3$)fluoroalkyl, ($C_1$-$C_3$)fluoroalkoxy, ($C_1$-$C_2$)alkylcarbonyl, cyano, —CONH$_2$, halogen and phenoxy;
or
$R^1$ represents hydrogen and $R^2$ and $R^3$ form, together with the carbon atom to which they are attached, an indanyl or a tetrahydronaphthyl group wherein the aromatic moiety of the groups is independently mono-, di- or tri-substituted, wherein the substituents are independently selected from the group consisting of ($C_1$-$C_3$)alkyl, ($C_1$-$C_3$)fluoroalkyl and halogen; and
$R^4$, $R^5$ and $R^6$ represent independently from each other hydrogen, ($C_1$-$C_3$)alkyl, ($C_3$-$C_6$)cycloalkyl, ($C_1$-$C_3$)alkoxy, ($C_1$-$C_3$)fluoroalkyl or halogen;
or a salt of such a compound.

2. A compound of formula (I) according to claim 1, wherein
n represents 1 or 2;
one of X and Y represents —N— or —N(O)— and the other one represents —N— or —C($R^6$)—;
$R^1$ represents hydrogen and $R^2$ represents hydrogen, ($C_1$-$C_2$)alkyl, ($C_1$-$C_2$)deuteroalkyl or hydroxy-methyl; or
$R^1$ and $R^2$ form, together with the carbon atom to which they are attached, a saturated carbocyclic ring of 3 to 6 members; and
$R^3$ represents an aryl group which is di- or tri-substituted, wherein the substituents are independently selected from the group consisting of ($C_1$-$C_3$)alkyl, ($C_3$-$C_6$)cycloalkyl, hydroxy-($C_1$-$C_2$)alkyl, ($C_1$-$C_3$)fluoroalkyl, ($C_1$-$C_3$)fluoroalkoxy, ($C_1$-$C_2$)alkylcarbonyl, cyano,

87

—CONH$_2$ and halogen; or an aryl-(C$_1$-C$_2$)alkyl group wherein the aromatic moiety of the groups is mono- or di-substituted with halogen;
or
R$^1$ represents hydrogen and R$^2$ and R$^3$ form, together with the carbon atom to which they are attached, an indanyl group which is in the aromatic moiety mono- or di-substituted with halogen; and
R$^4$, R$^5$ and R$^6$ represent independently from each other hydrogen, (C$_1$-C$_3$)alkyl, (C$_3$-C$_6$)cycloalkyl, methoxy, trifluoromethyl or halogen;
or a salt of such a compound.

3. A compound of formula (I) according to claim 1, wherein
n represents 1;
or a salt of such a compound.

4. A compound of formula (I) according to claim 1, wherein
n represents 2;
or a salt of such a compound.

5. A compound of formula (I) according to claim 1, wherein
X represents —N— and Y represents —C(R$^6$)— or —N—;
or a salt of such a compound.

6. A compound of formula (I) according to claim 1, wherein
R$^1$ represents hydrogen or methyl and R$^2$ represents hydrogen, (C$_1$-C$_2$)alkyl, (C$_1$-C$_2$)deuteroalkyl, hydroxy-methyl or heterocyclyl-methyl; or
R$^1$ and R$^2$ form, together with the carbon atom to which they are attached, a saturated carbocyclic ring of 3 to 5 members; and
R$^3$ represents an aryl, an aryl-(C$_1$-C$_2$)alkyl, a heteroaryl or a heteroaryloxy group wherein the aromatic moiety of the groups is independently di-, tri- or tetra-substituted, wherein the substituents are independently selected from the group consisting of (C$_1$-C$_3$)alkyl, (C$_3$-C$_6$)cycloalkyl, (C$_1$-C$_3$)alkoxy, hydroxy-(C$_1$-C$_2$)alkyl, (C$_1$-C$_3$)fluoroalkyl, (C$_1$-C$_3$)fluoro-alkoxy, (C$_1$-C$_2$)alkylcarbonyl, cyano, —CONH$_2$ and halogen;
or a salt of such a compound.

7. A compound of formula (I) according to claim 1, wherein
R$^1$ represents hydrogen and R$^2$ and R$^3$ form, together with the carbon atom to which they are attached, an indanyl or a tetrahydronaphthyl group wherein the aromatic moiety of the groups is independently mono-, di- or tri-substituted, wherein the substituents are independently selected from the group consisting of (C$_1$-C$_3$)alkyl, (C$_1$-C$_3$)fluoroalkyl and halogen;
or a salt of such a compound.

8. A compound of formula (I) according to claim 1, wherein
R$^1$ and R$^2$ represent hydrogen;
or a salt of such a compound.

9. A compound of formula (I) according to claim 1, wherein
R$^1$ and R$^2$ form, together with the carbon atom to which they are attached, a saturated carbocyclic ring of 3 to 5 members;
or a salt of such a compound.

10. A compound of formula (I) according to claim 1, wherein
R$^3$ represents a phenyl group which is di-, tri- or tetra-substituted, wherein the substituents are independently selected from the group consisting of (C$_1$-C$_3$)alkyl, (C$_3$-C$_6$)cycloalkyl, (C$_1$-C$_3$)alkoxy, hydroxy-(C$_1$-C$_2$)alkyl, (C$_1$-C$_3$)fluoroalkyl, (C$_1$-C$_3$)fluoroalkoxy, (C$_1$-C$_2$)alkylcarbonyl, cyano, —CONH$_2$ and halogen; a phenyl-methyl or phenyl-ethyl group wherein the aromatic moiety of the groups is independently mono- or di-substituted with halogen; a heteroaryl group which is mono- or di-substituted, wherein the substituents are independently selected from the group consisting of (C$_1$-C$_3$) alkyl and halogen; or a heteroaryloxy group which is mono- or di-substituted with (C$_1$-C$_3$)alkyl;
or a salt of such a compound.

11. A compound of formula (I) according to claim 1, selected from the group consisting of:
2-(2,4-Dichloro-phenyl)-N-(2,3-dihydro-furo[2,3-b]pyridin-3-yl)-acetamide;
2-(2-Chloro-4-fluoro-phenyl)-N-(2,3-dihydro-furo[2,3-b]pyridin-3-yl)-acetamide;
2-(2,4-Dichloro-phenyl)-N—(S)-(2,3-dihydro-furo[2,3-b]pyridin-3-yl)-acetamide;
2-(2,4-Dichloro-phenyl)-N—(R)-(2,3-dihydro-furo[2,3-b]pyridin-3-yl)-acetamide;
2-(2,4-Dichloro-6-methyl-phenyl)-N-(2,3-dihydro-furo[2,3-b]pyridin-3-yl)-acetamide;
2-(2,4-Dichloro-6-methyl-phenyl)-N—(S)-(2,3-dihydro-furo[2,3-b]pyridin-3-yl)-acetamide;
2-(2,4-Dichloro-6-methyl-phenyl)-N—(R)-(2,3-dihydro-furo[2,3-b]pyridin-3-yl)-acetamide;
2-(2,4-Dichloro-6-methyl-phenyl)-N-(3,4-dihydro-2H-pyrano[2,3-b]pyridin-4-yl)-acetamide;
2-(2,4-Dichloro-phenyl)-N-(3,4-dihydro-2H-pyrano[2,3-b]pyridin-4-yl)-acetamide;
2-(2-Cyano-phenyl)-N-(2,3-dihydro-furo[2,3-b]pyridin-3-yl)-acetamide;
N-(2,3-Dihydro-furo[2,3-b]pyridin-3-yl)-2-o-tolyl-acetamide;
N-(2,3-Dihydro-furo[2,3-b]pyridin-3-yl)-2-(2-methoxyphenyl)-acetamide;
2-(4-Cyano-phenyl)-N-(2,3-dihydro-furo[2,3-b]pyridin-3-yl)-acetamide;
N-(2,3-Dihydro-furo[2,3-b]pyridin-3-yl)-2-p-tolyl-acetamide;
2-(4-Chloro-phenyl)-N-(2,3-dihydro-furo[2,3-b]pyridin-3-yl)-acetamide;
N-(2,3-Dihydro-furo[2,3-b]pyridin-3-yl)-2-(4-trifluoromethyl-phenyl)-acetamide;
2-(2,4-Difluoro-phenyl)-N-(2,3-dihydro-furo[2,3-b]pyridin-3-yl)-acetamide;
N-(2,3-Dihydro-furo[2,3-b]pyridin-3-yl)-2-(4-fluoro-2-trifluoromethyl-phenyl)-acetamide;
N-(2,3-Dihydro-furo[2,3-b]pyridin-3-yl)-2-(2,4-dimethoxy-phenyl)-acetamide;
N-(2,3-Dihydro-furo[2,3-b]pyridin-3-yl)-2-(2-fluoro-4-methoxy-phenyl)-acetamide;
2-(3,4-Dichloro-phenyl)-N-(2,3-dihydro-furo[2,3-b]pyridin-3-yl)-acetamide;
N-(2,3-Dihydro-furo[2,3-b]pyridin-3-yl)-2-(2,4,6-trifluoro-phenyl)-acetamide;
2-(4-Chloro-phenyl)-N-(2,3-dihydro-furo[2,3-b]pyridin-3-yl)-propionamide;
1-(2,4-Dichloro-phenyl)-cyclopropanecarboxylic acid (2,3-dihydro-furo[2,3-b]pyridin-3-yl)-amide;
1-(2-Chloro-4-fluoro-phenyl)-cyclopentanecarboxylic acid (2,3-dihydro-furo[2,3-b]pyridin-3-yl)-amide;
2-(4-Chloro-phenyl)-N-(2,3-dihydro-furo[2,3-b]pyridin-3-yl)-isobutyramide;
3-(2,4-Dichloro-phenyl)-N-(2,3-dihydro-furo[2,3-b]pyridin-3-yl)-propionamide;

2-(2,4-Dichloro-6-methyl-phenyl)-N—(S)-(3,4-dihydro-2H-pyrano[2,3-b]pyridin-4-yl)-acetamide;
2-(2,4-Dichloro-6-methyl-phenyl)-N—(R)-(3,4-dihydro-2H-pyrano[2,3-b]pyridin-4-yl)-acetamide;
2-(2,4-Dichloro-phenyl)-N—(S)-(3,4-dihydro-2H-pyrano[2,3-b]pyridin-4-yl)-acetamide;
2-(2,4-Dichloro-phenyl)-N—(R)-(3,4-dihydro-2H-pyrano[2,3-b]pyridin-4-yl)-acetamide;
2-(2,4-Dichloro-6-ethyl-phenyl)-N-(2,3-dihydro-furo[2,3-b]pyridin-3-yl)-acetamide;
2-(2,4-Dichloro-6-trifluoromethyl-phenyl)-N-(2,3-dihydro-furo[2,3-b]pyridin-3-yl)-acetamide;
2-(2-Chloro-3-trifluoromethyl-phenyl)-N-(2,3-dihydro-furo[2,3-b]pyridin-3-yl)-acetamide;
2-(4-Chloro-2-trifluoromethyl-phenyl)-N-(2,3-dihydro-furo[2,3-b]pyridin-3-yl)-acetamide;
N-(2,3-Dihydro-furo[2,3-b]pyridin-3-yl)-2-(4-phenoxy-phenyl)-acetamide;
2-(2,4-Dichloro-6-cyano-phenyl)-N-(2,3-dihydro-furo[2,3-b]pyridin-3-yl)-acetamide;
2-(2-Chloro-4-fluoro-phenyl)-N-(3,4-dihydro-2H-pyrano[2,3-b]pyridin-4-yl)-acetamide;
2-(2,4-Dichloro-6-cyclopropyl-phenyl)-N-(2,3-dihydro-furo[2,3-b]pyridin-3-yl)-acetamide;
2-(4-Chloro-2-fluoro-3-methyl-6-trifluoromethyl-phenyl)-N-(2,3-dihydro-furo[2,3-b]pyridin-3-yl)-acetamide;
2-(2,4-Dichloro-5-fluoro-phenyl)-N-(2,3-dihydro-furo[2,3-b]pyridin-3-yl)-acetamide;
2-(2-Chloro-6-fluoro-3-methyl-phenyl)-N-(2,3-dihydro-furo[2,3-b]pyridin-3-yl)-acetamide;
2-(5-Chloro-2-trifluoromethyl-phenyl)-N-(2,3-dihydro-furo[2,3-b]pyridin-3-yl)-acetamide;
2-(2-Chloro-phenyl)-N-(3,4-dihydro-2H-pyrano[2,3-b]pyridin-4-yl)-acetamide;
2-(4-Cyano-phenyl)-N-(3,4-dihydro-2H-pyrano[2,3-b]pyridin-4-yl)-acetamide;
N-(3,4-Dihydro-2H-pyrano[2,3-b]pyridin-4-yl)-2-(4-trifluoromethyl-phenyl)-acetamide;
N-(3,4-Dihydro-2H-pyrano[2,3-b]pyridin-4-yl)-2-(3-trifluoromethyl-phenyl)-acetamide;
N-(3,4-Dihydro-2H-pyrano[2,3-b]pyridin-4-yl)-2-(4-phenoxy-phenyl)-acetamide;
2-(2-Chloro-3-trifluoromethyl-phenyl)-N-(3,4-dihydro-2H-pyrano[2,3-b]pyridin-4-yl)-acetamide;
2-(2-Chloro-6-fluoro-phenyl)-N-(3,4-dihydro-2H-pyrano[2,3-b]pyridin-4-yl)-acetamide;
2-(2,4-Difluoro-phenyl)-N-(3,4-dihydro-2H-pyrano[2,3-b]pyridin-4-yl)-acetamide;
N-(3,4-Dihydro-2H-pyrano[2,3-b]pyridin-4-yl)-2-(4-fluoro-2-trifluoromethyl-phenyl)-acetamide;
2-(4-Chloro-2-trifluoromethyl-phenyl)-N-(3,4-dihydro-2H-pyrano[2,3-b]pyridin-4-yl)-acetamide;
2-(2,3-Dichloro-phenyl)-N-(3,4-dihydro-2H-pyrano[2,3-b]pyridin-4-yl)-acetamide;
2-(3,4-Dichloro-phenyl)-N-(3,4-dihydro-2H-pyrano[2,3-b]pyridin-4-yl)-acetamide;
2-(2,4-Dichloro-6-trifluoromethyl-phenyl)-N-(3,4-dihydro-2H-pyrano[2,3-b]pyridin-4-yl)-acetamide;
2-(2,4-Dichloro-5-fluoro-phenyl)-N-(3,4-dihydro-2H-pyrano[2,3-b]pyridin-4-yl)-acetamide;
1-(2,4-Dichloro-phenyl)-cyclopropanecarboxylic acid (3,4-dihydro-2H-pyrano[2,3-b]pyridin-4-yl)-amide;
1-(2-Chloro-4-fluoro-phenyl)-cyclopentanecarboxylic acid (3,4-dihydro-2H-pyrano[2,3-b]pyridin-4-yl)-amide;
2-(2-Chloro-pyridin-3-yl)-N-(3,4-dihydro-2H-pyrano[2,3-b]pyridin-4-yl)-acetamide;
N-(3,4-Dihydro-2H-pyrano[2,3-b]pyridin-4-yl)-2-(2,6-dimethyl-pyridin-3-yloxy)-acetamide;
N-(3,4-Dihydro-2H-pyrano[2,3-b]pyridin-4-yl)-2-(3-methyl-isoxazol-5-yl)-acetamide;
N-(3,4-Dihydro-2H-pyrano[2,3-b]pyridin-4-yl)-2-(5-methyl-pyrazol-1-yl)-acetamide;
2-(4-Chloro-phenyl)-N-(3,4-dihydro-2H-pyrano[2,3-b]pyridin-4-yl)-propionamide;
3-(2,4-Dichloro-phenyl)-N-(3,4-dihydro-2H-pyrano[2,3-b]pyridin-4-yl)-propionamide;
2-(2,3-Dichloro-phenyl)-N-(2,3-dihydro-furo[2,3-b]pyridin-3-yl)-acetamide;
2-(2,3-Dichloro-6-fluoro-phenyl)-N-(2,3-dihydro-furo[2,3-b]pyridin-3-yl)-acetamide;
N-(2,3-Dihydro-furo[2,3-b]pyridin-3-yl)-2-(2-fluoro-6-trifluoromethyl-phenyl)-acetamide;
N-(2,3-Dihydro-furo[2,3-b]pyridin-3-yl)-2-(3-fluoro-4-trifluoromethoxy-phenyl)-acetamide;
2-(2,4-Dichloro-6-fluoro-phenyl)-N-(3,4-dihydro-2H-pyrano[2,3-b]pyridin-4-yl)-acetamide;
2-(2,3-Dichloro-6-trifluoromethyl-phenyl)-N-(2,3-dihydro-furo[2,3-b]pyridin-3-yl)-acetamide;
2-(2,6-Dichloro-3-trifluoromethyl-phenyl)-N-(2,3-dihydro-furo[2,3-b]pyridin-3-yl)-acetamide;
2-(2-Chloro-3-trifluoromethyl-phenyl)-N—(S)-(2,3-dihydro-furo[2,3-b]pyridin-3-yl)-acetamide;
2-(2-Chloro-3-trifluoromethyl-phenyl)-N—(R)-(2,3-dihydro-furo[2,3-b]pyridin-3-yl)-acetamide; and
2-(2-Chloro-3-cyano-phenyl)-N-(2,3-dihydro-furo[2,3-b]pyridin-3-yl)-acetamide;
or a salt of such a compound.

12. A compound of formula (I) according to claim 1, selected from the group consisting of:
2-(2,4-Dichloro-6-fluoro-phenyl)-N-(2,3-dihydro-furo[2,3-b]pyridin-3-yl)-acetamide;
2-(3,6-Dichloro-2-fluoro-phenyl)-N-(2,3-dihydro-furo[2,3-b]pyridin-3-yl)-acetamide;
2-(2-Chloro-3,6-difluoro-phenyl)-N-(2,3-dihydro-furo[2,3-b]pyridin-3-yl)-acetamide;
2-(2,4-Dichloro-phenyl)-N-2,3-dihydro-furo[2,3-b]pyridin-3-yl-3-hydroxy-propionamide;
2-Chloro-3-[(2,3-dihydro-furo[2,3-b]pyridin-3-ylcarbamoyl)-methyl]-benzamide;
2-(2,4-Dichloro-phenyl)-N-2,3-dihydro-furo[2,3-b]pyridin-3-yl-3-pyrrolidin-1-yl-propionamide;
N-(2,3-Dihydro-furo[2,3-b]pyridin-3-yl)-4-(4-fluoro-phenyl)-butyramide;
2-(2,4-Dichloro-phenyl)-N-(2,3-dihydro-furo[2,3-c]pyridin-3-yl)-acetamide;
2-(2,4-Dichloro-phenyl)-N-2,3-dihydro-furo[2,3-b]pyridin-3-yl-butyramide;
2-(2,4-Dichloro-phenyl)-N-2,3-dihydro-furo[2,3-b]pyridin-3-yl-propionamide;
2-(2,4-Dichloro-phenyl)-2-trideuteromethyl-N-2,3-dihydro-furo[2,3-b]pyridin-3-yl-acetamide;
2-(2-Chloro-3-trifluoromethyl-phenyl)-N-(2,3-dihydro-furo[2,3-c]pyridin-3-yl)-acetamide;
2-(2-Chloro-4-trifluoromethyl-phenyl)-N-(2,3-dihydro-furo[2,3-b]pyridin-3-yl)-acetamide;
2-(2,4-Dichloro-6-methyl-phenyl)-N-(2,3-dihydro-furo[2,3-c]pyridin-3-yl)-acetamide;
N-(2,3-Dihydro-furo[2,3-b]pyridin-3-yl)-2-(2-fluoro-3-trifluoromethyl-phenyl)-acetamide;
2-(2-Chloro-3-trifluoromethyl-phenyl)-N-2,3-dihydro-furo[2,3-b]pyridin-3-yl-propionamide;

(S)-2-(2,4-Dichloro-phenyl)-N—((S)-2,3-dihydro-furo[2,3-b]pyridin-3-yl)-propionamide;
(S)-2-(2,4-Dichloro-phenyl)-N—((R)-2,3-dihydro-furo[2,3-b]pyridin-3-yl)-propionamide;
(R)-2-(2,4-Dichloro-phenyl)-N—((S)-2,3-dihydro-furo[2,3-b]pyridin-3-yl)-propionamide;
(R)-2-(2,4-Dichloro-phenyl)-N—((R)-2,3-dihydro-furo[2,3-b]pyridin-3-yl)-propionamide;
2-(2-Chloro-4-cyano-phenyl)-N-(2,3-dihydro-furo[2,3-b]pyridin-3-yl)-acetamide;
2-(3-Chloro-2-trifluoromethyl-phenyl)-N-(2,3-dihydro-furo[2,3-b]pyridin-3-yl)-acetamide;
2-(2-Chloro-3-cyano-phenyl)-N—((R)-2,3-dihydro-furo[2,3-b]pyridin-3-yl)-acetamide;
2-(2-Chloro-3-cyano-phenyl)-N—((S)-2,3-dihydro-furo[2,3-b]pyridin-3-yl)-acetamide;
2-(2,4-Dichloro-phenyl)-N-(7-methyl-2,3-dihydro-furo[2,3-c]pyridin-3-yl)-acetamide;
2-(2,4-Dichloro-6-methyl-phenyl)-N—((R)-2,3-dihydro-furo[2,3-c]pyridin-3-yl)-acetamide;
2-(2,4-Dichloro-6-methyl-phenyl)-N—((S)-2,3-dihydro-furo[2,3-c]pyridin-3-yl)-acetamide;
2-(2,4-Dichloro-6-hydroxymethyl-phenyl)-N-(2,3-dihydro-furo[2,3-b]pyridin-3-yl)-acetamide;
N-(7-Cyclopropyl-2,3-dihydro-furo[2,3-c]pyridin-3-yl)-2-(2,4-dichloro-phenyl)-acetamide;
2-(2,4-Dichloro-phenyl)-N-(7-methoxy-2,3-dihydro-furo[2,3-c]pyridin-3-yl)-acetamide;
N-(7-Chloro-2,3-dihydro-furo[2,3-c]pyridin-3-yl)-2-(2,4-dichloro-phenyl)-acetamide;
2-(2-Chloro-3-cyano-4-fluoro-phenyl)-N-(2,3-dihydro-furo[2,3-b]pyridin-3-yl)-acetamide;
2-(2-Chloro-3-trifluoromethoxy-phenyl)-N-(2,3-dihydro-furo[2,3-b]pyridin-3-yl)-acetamide;
2-(2-Chloro-3-trifluoromethyl-phenyl)-N-(5,6-dihydro-furo[2,3-c]pyridazin-5-yl)-acetamide;
2-(2,4-Dichloro-6-methyl-phenyl)-N-(5,6-dihydro-furo[2,3-c]pyridazin-5-yl)-acetamide;
2-(3-Acetyl-2-chloro-phenyl)-N-(2,3-dihydro-furo[2,3-b]pyridin-3-yl)-acetamide;
2-(2,4-Dichloro-3-cyano-phenyl)-N-(2,3-dihydro-furo[2,3-b]pyridin-3-yl)-acetamide;
2-(3-Cyano-2-trifluoromethyl-phenyl)-N-(2,3-dihydro-furo[2,3-b]pyridin-3-yl)-acetamide;
2-(2-Chloro-3-difluoromethyl-phenyl)-N-(2,3-dihydro-furo[2,3-b]pyridin-3-yl)-acetamide;
N-(5-Chloro-2,3-dihydro-furo[2,3-c]pyridin-3-yl)-2-(2-chloro-3-trifluoromethyl-phenyl)-acetamide;
N-(5-Chloro-2,3-dihydro-furo[2,3-c]pyridin-3-yl)-2-(2,4-dichloro-phenyl)-acetamide;
2-(2-Chloro-3-trifluoromethyl-phenyl)-N-(5-methyl-2,3-dihydro-furo[2,3-c]pyridin-3-yl)-acetamide;
(S)-2-(2-Chloro-3-trifluoromethyl-phenyl)-N—((S)-2,3-dihydro-furo[2,3-b]pyridin-3-yl)-propionamide;
(S)-2-(2-Chloro-3-trifluoromethyl-phenyl)-2-trideuteromethyl-N—((S)-2,3-dihydro-furo[2,3-b]pyridin-3-yl)-acetamide;
(S)-2-(2-Chloro-3-trifluoromethyl-phenyl)-N—((R)-2,3-dihydro-furo[2,3-b]pyridin-3-yl)-propionamide;
(S)-2-(2-Chloro-3-trifluoromethyl-phenyl)-2-trideuteromethyl-N—((R)-2,3-dihydro-furo[2,3-b]pyridin-3-yl)-acetamide;
(R)-2-(2-Chloro-3-trifluoromethyl-phenyl)-N—((S)-2,3-dihydro-furo[2,3-b]pyridin-3-yl)-propionamide;
(R)-2-(2-Chloro-3-trifluoromethyl-phenyl)-2-trideuteromethyl-N—((S)-2,3-dihydro-furo[2,3-b]pyridin-3-yl)-acetamide;
(R)-2-(2-Chloro-3-trifluoromethyl-phenyl)-N—((R)-2,3-dihydro-furo[2,3-b]pyridin-3-yl)-propionamide;
(R)-2-(2-Chloro-3-trifluoromethyl-phenyl)-2-trideuteromethyl-N—((R)-2,3-dihydro-furo[2,3-b]pyridin-3-yl)-acetamide;
2-(2-Chloro-3-trifluoromethyl-phenyl)-2-trideuteromethyl-N—((R)-2,3-dihydro-furo[2,3-b]pyridin-3-yl)-acetamide;
2-(2-Chloro-3-trifluoromethyl-phenyl)-2-trideuteromethyl-N—((S)-2,3-dihydro-furo[2,3-b]pyridin-3-yl)-acetamide;
2-(2-Chloro-3-trifluoromethyl-phenyl)-N-(4-methyl-2,3-dihydro-furo[2,3-c]pyridin-3-yl)-acetamide;
2-(2-Chloro-3-trifluoromethyl-phenyl)-N-(7-oxy-2,3-dihydro-furo[2,3-b]pyridin-3-yl)-acetamide;
5,7-dichloro-N-(2,3-dihydrofuro[2,3-b]pyridin-3-yl)-2,3-dihydro-1H-indene-1-carboxamide;
2-(2,4-Dichloro-6-methyl-phenyl)-N-(4-methyl-2,3-dihydro-furo[2,3-c]pyridin-3-yl)-acetamide;
2-(2-Chloro-3-trifluoromethyl-phenyl)-N-(4-cyclopropyl-2,3-dihydro-furo[2,3-c]pyridin-3-yl)-acetamide;
2-(2,4-Dichloro-6-methyl-phenyl)-N-(6-methyl-2,3-dihydro-furo[2,3-b]pyridin-3-yl)-acetamide;
2-(2-Chloro-3-trifluoromethyl-phenyl)-N-(6-methyl-2,3-dihydro-furo[2,3-b]pyridin-3-yl)-acetamide;
2-(2-Chloro-3-trifluoromethyl-phenyl)-N-(4-methoxy-6-methyl-2,3-dihydro-furo[2,3-b]pyridin-3-yl)-acetamide;
2-(2-Chloro-3-trifluoromethyl-phenyl)-N-(4-ethoxy-6-methyl-2,3-dihydro-furo[2,3-b]pyridin-3-yl)-acetamide;
2-(2-Chloro-3-trifluoromethyl-phenyl)-N-(4-methyl-2,3-dihydro-furo[2,3-b]pyridin-3-yl)-acetamide;
2-(2,4-Dichloro-6-methyl-phenyl)-N-(4-methyl-2,3-dihydro-furo[2,3-b]pyridin-3-yl)-acetamide;
2-(2-Chloro-3-trifluoromethyl-phenyl)-N-(4-methoxy-2,3-dihydro-furo[2,3-b]pyridin-3-yl)-acetamide;
2-(2,4-Dichloro-phenoxy)-N-(2,3-dihydro-furo[2,3-b]pyridin-3-yl)-acetamide;
2-(3,4-Dichloro-phenoxy)-N-(2,3-dihydro-furo[2,3-b]pyridin-3-yl)-acetamide;
N-(2,3-Dihydro-furo[2,3-b]pyridin-3-yl)-2-(2,4-dimethyl-phenoxy)-acetamide;
N-(6-Chloro-2,3-dihydro-furo[2,3-b]pyridin-3-yl)-2-(2-chloro-3-trifluoromethyl-phenyl)-acetamide;
N-(6-Chloro-2,3-dihydro-furo[2,3-b]pyridin-3-yl)-2-(2,4-dichloro-6-methyl-phenyl)-acetamide;
5-chloro-N-(2,3-dihydrofuro[2,3-b]pyridin-3-yl)-2,3-dihydro-1H-indene-1-carboxamide;
2-(2-Chloro-3-trifluoromethyl-phenyl)-N-(6-oxy-2,3-dihydro-furo[2,3-c]pyridin-3-yl)-acetamide;
5-chloro-N—((R)-2,3-dihydrofuro[2,3-b]pyridin-3-yl)-2,3-dihydro-1H-indene-2-carboxamide;
5-chloro-N—((S)-2,3-dihydrofuro[2,3-b]pyridin-3-yl)-2,3-dihydro-1H-indene-2-carboxamide;
2-(2,4-Dichloro-6-methyl-phenyl)-N-(4-trifluoromethyl-2,3-dihydro-furo[2,3-b]pyridin-3-yl)-acetamide; and
2-(2-Chloro-3-trifluoromethyl-phenyl)-N-(4-trifluoromethyl-2,3-dihydro-furo[2,3-b]pyridin-3-yl)-acetamide;
or a salt of such a compound.

13. A pharmaceutical composition containing, as active principle, a compound of formula (I) according to claim 1, or a pharmaceutically acceptable salt thereof, and at least one therapeutically inert excipient.

14. The method for treatment of a disease, which is associated with the activation of the $P2X_7$ comprising the administration of an effective amount of a compound of formula (I)

according to claim 1, wherein the disease is selected from the group consisting of: pain; rheumatoid arthritis, osteoarthritis, irritable bowel disease, and chronic obstructive pulmonary disease (COPD).

* * * * *

SEQUENCE LISTING

```
<160> NUMBER OF SEQ ID NOS: 2

<210> SEQ ID NO 1
<211> LENGTH: 35
<212> TYPE: DNA
<213> ORGANISM: Homo sapiens
<220> FEATURE:
<221> NAME/KEY: source
<222> LOCATION: 1..35
<223> OTHER INFORMATION: /mol_type="DNA"
      /organism="Homo sapiens"

<400> SEQUENCE: 1
atcgcggccg ctcagtaagg actcttgaag ccact          35

<210> SEQ ID NO 2
<211> LENGTH: 38
<212> TYPE: DNA
<213> ORGANISM: Homo sapiens
<220> FEATURE:
<221> NAME/KEY: source
<222> LOCATION: 1..38
<223> OTHER INFORMATION: /mol_type="DNA"
      /organism="Homo sapiens"

<400> SEQUENCE: 2
cgccgctagc accaccatgc cggcctgctg cagctgca       38
```